(12) United States Patent
Williams et al.

(10) Patent No.: US 7,820,680 B2
(45) Date of Patent: Oct. 26, 2010

(54) HIV INTEGRASE INHIBITORS

(75) Inventors: Peter D. Williams, Harleysville, PA (US); John S. Wai, Harleysville, PA (US); Mark W. Embrey, Harleysville, PA (US); Donnette D. Staas, Harleysville, PA (US); Linghang Zhuang, Chalfont, PA (US)

(73) Assignee: Merck & Co., Inc., Rahway, NJ (US)

( * ) Notice: Subject to any disclaimer, the term of this patent is extended or adjusted under 35 U.S.C. 154(b) by 1079 days.

(21) Appl. No.: 10/592,222

(22) PCT Filed: Mar. 4, 2005

(86) PCT No.: PCT/US2005/006916
§ 371 (c)(1),
(2), (4) Date: Sep. 8, 2006

(87) PCT Pub. No.: WO2005/092099
PCT Pub. Date: Oct. 6, 2005

(65) Prior Publication Data
US 2008/0009490 A1    Jan. 10, 2008

Related U.S. Application Data

(60) Provisional application No. 60/551,602, filed on Mar. 9, 2004.

(51) Int. Cl.
*A61K 31/519* (2006.01)
(52) U.S. Cl. ............... 514/259.1; 544/256; 544/350
(58) Field of Classification Search .......... 544/256, 544/350
See application file for complete search history.

(56) References Cited

U.S. PATENT DOCUMENTS

| | | | |
|---|---|---|---|
| 6,262,055 B1 | 7/2001 | Young et al. | |
| 6,306,891 B1 | 10/2001 | Selnick et al. | |
| 6,380,249 B1 | 4/2002 | Young et al. | |
| 6,841,558 B2 | 1/2005 | Anthony et al. | |
| 6,919,351 B2 | 7/2005 | Anthony et al. | |
| 6,921,759 B2 | 7/2005 | Anthony et al. | |
| 7,109,186 B2 | 9/2006 | Walker et al. | |
| 7,169,780 B2 | 1/2007 | Crescenzi et al. | |
| 7,211,572 B2 | 5/2007 | Miyazaki et al. | |
| 7,217,713 B2 | 5/2007 | Crescenzi et al. | |
| 7,232,819 B2 | 6/2007 | Di Francesco et al. | |
| 7,279,487 B2 | 10/2007 | Egbertson et al. | |
| 7,435,734 B2 | 10/2008 | Crescenzi et al. | |
| 7,459,452 B2 | 12/2008 | Di Francesco et al. | |
| 7,598,264 B2 | 10/2009 | Han et al. | |
| 7,619,086 B2 | 11/2009 | Morrissette et al. | |
| 2003/0055071 A1 | 3/2003 | Anthony et al. | |
| 2003/0229079 A1 | 12/2003 | Payne et al. | |
| 2004/0229909 A1 | 11/2004 | Kiyama et al. | |
| 2005/0010048 A1 | 1/2005 | Zhuang et al. | |
| 2007/0161639 A1 | 7/2007 | Jones et al. | |
| 2008/0275004 A1 | 11/2008 | Crescenzi et al. | |
| 2009/0054399 A1 | 2/2009 | Vacca et al. | |
| 2009/0099168 A1 | 4/2009 | Donghi et al. | |

FOREIGN PATENT DOCUMENTS

| | | |
|---|---|---|
| EP | 1422218 A1 | 5/2004 |
| WO | WO 01/00578 A1 | 1/2001 |
| WO | WO 02/30426 A1 | 4/2002 |
| WO | WO 02/036734 A2 | 5/2002 |
| WO | WO 02/055079 A2 | 7/2002 |
| WO | WO 03/035076 A1 | 5/2003 |
| WO | WO 03/035077 A1 | 5/2003 |
| WO | WO 03/062204 A1 | 7/2003 |
| WO | WO 2004/004657 A2 | 1/2004 |

OTHER PUBLICATIONS

Ratner, L., et al., "Complete Nucleotide Sequence of the AIDS Virus, HTLV-III", Nature, vol. 313, pp. 277-284, (1985).
Toh, H., et al., "Close Structural Resemblance Between Putative Polymerase of a Drosphila Transposable Genetic Element 17.6 and Pol Gene Product of Moloney Murine Leukemia Virus", EMBO Journal, vol. 4, No. 5, pp. 1267-1272, (1985).

(Continued)

*Primary Examiner*—James O Wilson
*Assistant Examiner*—Brian McDowell
(74) *Attorney, Agent, or Firm*—Kenneth R. Walton; Sheldon O. Heber

(57) ABSTRACT

Bicyclic uracils and related compounds are inhibitors of HIV integrase and inhibitors of HIV replication. In one embodiment, the compounds are of Formula I:

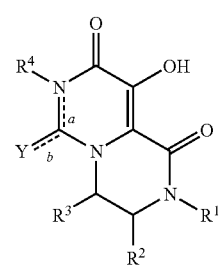

wherein a, b, Y, $R^1$, $R^2$, $R^3$ and $R^4$ are defined herein. The compounds are useful in the prevention and treatment of infection by HIV and in the prevention, delay in the onset, and treatment of AIDS. The compounds are employed against HIV infection and AIDS as compounds per se or in the form of pharmaceutically acceptable salts. The compounds and their salts can be employed as ingredients in pharmaceutical compositions, optionally in combination with other antivirals, immunomodulators, antibiotics or vaccines.

12 Claims, No Drawings

OTHER PUBLICATIONS

Power, M.D., et al., "Nucleotide Sequence of SRV-1, a Type D Simian Acquired Immune Deficiency Syndrome Retrovirus", Science, vol. 231, pp. 1567-1572, (1986).

Pearl, L.H., et al., "A Structural Model for the Retroviral Proteases", Nature, vol. 329, pp. 351-354, (1987).

Neamati, N., "Patented Small Molecule Inhibitors of HIV-1 Integrase : a 10-Year Saga", Expert Opinion on Therapeutic Patents, vol. 12, No. 5, pp. 709-724 (2002).

Machon, et al., "Synthesis of Perhydropyrazino[1,2-c]Pyrimidine Derivatives", Farmaco Edizione Scientifica vol. 40, No. 9, pp. 695-700 (1985).

Selected papers from Interference No. 105,655 between U.S. Appl. No. 10/587,601 (Merck) and US 7,211,572 (Japan Tobacco)—Merck Amended Miscellaneous Motion 1 dated Nov. 10, 2008; Interlocutory Order dated Nov. 18, 2008, Granting Merck's Unopposed Revised Miscellaneous Motion 1; Redeclaration of Interference dated Nov. 18, 2008; Judgement dated Dec. 5, 2008.

Amendment and Response to Restriction Requirement filed Jul. 2, 2009 in U.S. Appl. No. 11/920,032.

HIV INTEGRASE INHIBITORS

This application is the National Stage of International Application No. PCT/US2005/006916, filed on Mar. 4, 2005, which claims the benefit of U.S. Provisional Application No. 60/551,602, filed Mar. 9, 2004, the disclosure of which is hereby incorporated by reference in its entirety.

FIELD OF THE INVENTION

The present invention is directed to bicyclic uracils and related compounds and pharmaceutically acceptable salts thereof, their synthesis, and their use as inhibitors of the HIV integrase enzyme. The compounds and pharmaceutically acceptable salts thereof of the present invention are useful for preventing or treating infection by HIV and for preventing or treating or delaying the onset of AIDS.

BACKGROUND OF THE INVENTION

A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is the insertion by virally-encoded integrase of proviral DNA into the host cell genome, a required step in HIV replication in human T-lymphoid and monocytoid cells. Integration is believed to be mediated by integrase in three steps: assembly of a stable nucleoprotein complex with viral DNA sequences; cleavage of two nucleotides from the 3' termini of the linear proviral DNA; covalent joining of the recessed 3' OH termini of the proviral DNA at a staggered cut made at the host target site. The fourth step in the process, repair synthesis of the resultant gap, may be accomplished by cellular enzymes.

Nucleotide sequencing of HIV shows the presence of a pol gene in one open reading frame [Ratner, L. et al., Nature, 313, 277 (1985)]. Amino acid sequence homology provides evidence that the pol sequence encodes reverse transcriptase, integrase and an HIV protease [Toh, H. et al., EMBO J. 4, 1267 (1985); Power, M. D. et al., Science, 231, 1567 (1986); Pearl, L. H. et al., Nature, 329, 351 (1987)]. All three enzymes have been shown to be essential for the replication of HIV.

It is known that some antiviral compounds which act as inhibitors of HIV replication are effective agents in the treatment of AIDS and similar diseases, including reverse transcriptase inhibitors such as azidothymidine (AZT) and efavirenz and protease inhibitors such as indinavir and nelfinavir. The compounds of this invention are inhibitors of HIV integrase and inhibitors of HIV replication. The inhibition of integrase in vitro and HIV replication in cells is a direct result of inhibiting the strand transfer reaction catalyzed by the recombinant integrase in vitro in HIV infected cells. The particular advantage of the present invention is highly specific inhibition of HIV integrase and HIV replication.

The following references are of interest as background:

U.S. Pat. Nos. 6,380,249, 6,306,891, and 6,262,055 disclose 2,4-dioxobutyric acids and acid esters useful as HIV integrase inhibitors.

WO 01/00578 discloses 1-(aromatic- or heteroaromatic-substituted)-3-(heteroaromatic substituted)-1,3-propanediones useful as HIV integrase inhibitors.

US 2003/0055071 (corresponding to WO 02/30930), WO 02/30426, and WO 02/55079 each disclose certain 8-hydroxy-1,6-naphthyridine-7-carboxamides as HIV integrase inhibitors.

WO 02/036734 discloses certain aza- and polyaza-naphthalenyl ketones to be HIV integrase inhibitors.

WO 03/016275 discloses certain compounds having integrase inhibitory activity.

WO 03/35076 discloses certain 5,6-dihydroxypyrimidine-4-carboxamides as HIV integrase inhibitors, and WO 03/35077 discloses certain N-substituted 5-hydroxy-6-oxo-1,6-dihydropyrimidine-4-carboxamides as HIV integrase inhibitors.

WO 03/062204 discloses certain hydroxynaphthyridinone carboxamides that are useful as HIV integrase inhibitors.

WO 04/004657 discloses certain hydroxypyrrole derivatives that are HIV integrase inhibitors.

SUMMARY OF THE INVENTION

The present invention is directed to bicyclic uracil compounds and compounds related thereto. These compounds are useful in the inhibition of HIV integrase, the prevention of infection by HIV, the treatment of infection by HIV and in the prevention, treatment, and delay in the onset of AIDS and/or ARC, either as compounds or their pharmaceutically acceptable salts or hydrates (when appropriate), or as pharmaceutical composition ingredients, whether or not in combination with other HIV/AIDS antivirals, anti-infectives, immunomodulators, antibiotics or vaccines. More particularly, the present invention includes compounds of Formula I, and pharmaceutically acceptable salts thereof:

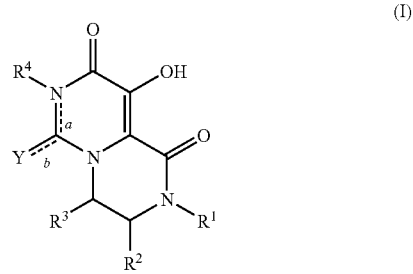

(I)

wherein:
bond "a" is a single bond or a double bond;
bond "b" is a double bond when bond "a" is a single bond; and
bond "b" is a single bond when bond "a" is a double bond;
Y is O, S, or $NR^5$, when bond "a" is a single bond;
Y is $N(R^6)R^7$, when bond "a" is a double bond;
$R^1$ is $C_{1-6}$ alkyl substituted with T, wherein T is:
  (A) aryl which is:
    (i) optionally substituted with from 1 to 5 substituents each of which is independently:
      (1) —$C_{1-6}$ alkyl optionally substituted with —OH, —O—$C_{1-6}$ alkyl, —O—$C_{1-6}$ haloalkyl, —CN, —$NO_2$, —$N(R^A)R^B$, —$C(O)N(R^A)R^B$, —$C(O)R^A$, —$CO_2R^A$, —$SR^A$, —$S(O)R^A$, —$SO_2R^A$, —$SO_2N(R^A)R^B$, —$N(R^A)C(O)R^B$, —$N(R^A)CO_2R^B$, —$N(R^A)SO_2R^B$, —$N(R^A)SO_2N(R^A)R^B$, —$OC(O)N(R^A)R^B$, or —$N(R^A)C(O)N(R^A)R^B$,
      (2) —O—$C_{1-6}$ alkyl,
      (3) —$C_{1-6}$ haloalkyl,
      (4) —O—$C_{1-6}$ haloalkyl,
      (5) —OH,
      (6) halo,
      (7) —CN,
      (8) —$NO_2$, (9) —N(R$^A$)R$^B$,
(10) —C(O)N(R$^A$)R$^B$,
(11) —C(O)R$^A$,
(12) —CO$_2$R$^A$,
(13) —SR$^A$,
(14) —S(O)R$^A$,
(15) —SO$_2$R$^A$,
(16) —SO$_2$N(R$^A$)R$^B$,
(17) —N(R$^A$)SO$_2$R$^B$,
(18) —N(R$^A$)SO$_2$N(R$^A$)R$^B$,
(19) —N(R$^A$)C(O)R$^B$,
(20) —N(R$^A$)C(O)—C(O)N(R$^A$)R$^B$, or
(21) —N(R$^A$)CO$_2$R$^B$, and (ii) optionally substituted with from 1 to 3 substituents each of which is independently:
(1) -HetA,
(2) -HetB,
(3) phenyl,
(4) benzyl, or
(5) —C(O)-HetA, or (B) heteroaryl which is:
(i) optionally substituted with from 1 to 4 substituents each of which is independently halogen, —C$_{1-6}$ alkyl, —C$_{1-6}$ haloalkyl, —O—C$_{1-6}$ alkyl, —O—C$_{1-6}$ haloalkyl, or —OH; and
(ii) optionally substituted with 1 or 2 substituents each of which is independently aryl or —C$_{1-6}$ alkyl substituted with aryl;

R$^2$ is:
(1) H,
(2) C$_{1-6}$ alkyl, or
(3) C$_{1-6}$ alkyl substituted with —CO$_2$R$^A$ or —C(O)N(R$^C$)R$^D$;

or alternatively R$^1$ and R$^2$ together with the atom to which each is attached form a saturated 5- or 6-membered ring containing the nitrogen to which R$^1$ is attached, optionally a second nitrogen atom and a balance of carbon atoms; wherein the saturated 5- or 6-membered ring is substituted with T as defined above;

R$^3$ is:
(1) H,
(2) C$_{1-6}$ alkyl, or
(3) C$_{1-6}$ alkyl substituted with:
(a) —OH,
(b) —O—C$_{1-6}$ alkyl,
(c) —N(R$^E$)$_2$,
(d) —N(R$^E$)R$^F$,
(e) aryl, which is optionally substituted with from 1 to 5 substituents each of which is independently halo, —C$_{1-6}$ alkyl, —O—C$_{1-6}$ alkyl, —C$_{1-6}$ haloalkyl, or —OH,
(f) —O—C$_{1-6}$ alkylene-aryl, in which the aryl is optionally substituted with from 1 to 5 substituents each of which is independently halo, —C$_{1-6}$ alkyl, —O—C$_{1-6}$ alkyl, —C$_{1-6}$ haloalkyl, or —OH,
(g) heteroaryl, which is optionally substituted with from 1 to 4 substituents each of which is independently halogen, —C$_{1-6}$ alkyl, —C$_{1-6}$ haloalkyl, —O—C$_{1-6}$ alkyl, —O—C$_{1-6}$ haloalkyl, or —OH, or
(h) heteromonocycle, which is optionally substituted with from 1 to 6 substituents each of which is independently halogen, —C$_{1-6}$ alkyl, —C$_{1-6}$ haloalkyl, —O—C$_{1-6}$ alkyl, —O—C$_{1-6}$ haloalkyl, or oxo;

R$^4$ is absent when bond "a" is a double bond;
R$^4$ is as follows when bond "a" is a single bond:
(1) H,
(2) C$_{1-6}$ alkyl,
(3) C$_{1-6}$ alkyl substituted with 1 or 2 substituents each of which is independently:
(a) —OH,
(b) —O—C$_{1-6}$ alkyl,
(c) —C$_{1-6}$ haloalkyl,
(d) —CO$_2$R$^A$,
(e) —C(O)N(R$^C$)R$^D$,
(f) —C(O)C(O)N(R$^A$)R$^B$,
(g) —S—C$_{1-6}$ alkyl,
(h) —S-aryl,
(i) —S(O)—C$_{1-6}$ alkyl,
(j) —S(O)-aryl,
(k) —SO$_2$—C$_{1-6}$ alkyl,
(l) —SO$_2$-aryl,
(m) —N(R$^E$)$_2$,
(n) —N(R$^E$)R$^F$,
(o) —C$_{3-8}$ cycloalkyl, which is
(i) optionally substituted with from 1 to 6 substituents each of which is independently —C$_{1-6}$ alkyl, —OH, —O—C$_{1-6}$ alkyl, or —C$_{1-6}$ haloalkyl, and
(ii) optionally substituted with (a) aryl, (b) —C$_{1-6}$ alkylene-aryl, (c) heteroaryl optionally substituted with from 1 to 3 substituents each of which is independently a —C$_{1-6}$ alkyl, or (d) heteromonocycle optionally substituted with from 1 to 4 substituents each of which is independently —C$_{1-6}$ alkyl, —C$_{1-6}$ alkylene-aryl, or oxo,
(p) aryl, which is:
(i) optionally substituted with from 1 to 5 substituents each of which is independently halo, —C$_{1-6}$ alkyl, —O—C$_{1-6}$ alkyl, —C$_{1-6}$ haloalkyl, or —OH, and
(ii) optionally substituted with (a) heteroaryl optionally substituted with from 1 to 3 substituents each of which is independently a —C$_{1-6}$ alkyl, or (b) heteromonocycle optionally substituted with from 1 to 4 substituents each of which is independently —C$_{1-6}$ alkyl, —C$_{1-6}$ alkylene-aryl, or oxo,
(q) bicyclic or tricyclic carbocycle, which is optionally substituted with from 1 to 7 substituents each of which is independently halogen, —C$_{1-6}$ alkyl, —C$_{1-6}$ haloalkyl, OH, —O—C$_{1-6}$ alkyl, or —O—C$_{1-6}$ haloalkyl,
(r) heteroaryl, which is:
(i) optionally substituted with from 1 to 4 substituents each of which is independently halogen, —C$_{1-6}$ alkyl, —C$_{1-6}$ haloalkyl, —O—C$_{1-6}$ alkyl, —O—C$_{1-6}$ haloalkyl, or —OH, and
(ii) optionally substituted with (a) aryl, (b) —C$_{1-6}$ alkylene-aryl or (c) heteromonocycle optionally substituted with from 1 to 4 substituents each of which is independently —C$_{1-6}$ alkyl, —C$_{1-6}$ alkylene-aryl, or oxo,
(s) heteromonocycle, which is:
(i) optionally substituted with from 1 to 6 substituents each of which is independently halogen, —C$_{1-6}$ alkyl, —C$_{1-6}$ haloalkyl, —O—C$_{1-6}$ alkyl, —O—C$_{1-6}$ haloalkyl, —C(O)—C$_{1-6}$ alkyl, —C(O)C(O)N(R$^A$)R$^B$, or oxo, and
(ii) optionally substituted with:
(a) —C$_{1-6}$ alkylene-C$_{3-8}$ cycloalkyl,
(b) aryl,
(c) —C$_{1-6}$ alkylene-aryl,
(d) heteroaryl optionally substituted with from 1 to 3 substituents each of which is independently a —C$_{1-6}$ alkyl, (e) heteromonocycle optionally substituted with from 1 to 4 substituents each of which is independently —$C_{1-6}$ alkyl, —$C_{1-6}$ alkylene-aryl, or oxo, or
(f) —C(O)—$C_{1-6}$ alkylene-heteromonocycle wherein the heteromonocycle is optionally substituted with from 1 to 4 substituents each of which is independently —$C_{1-6}$ alkyl, —$C_{1-6}$ alkylene-aryl, or oxo, or
(s) bicyclic or tricyclic heterocycle, which is optionally substituted with from 1 to 7 substituents each of which is independently halogen, —$C_{1-6}$ alkyl, —$C_{1-6}$ haloalkyl, —O—$C_{1-6}$ alkyl, —O—$C_{1-6}$ haloalkyl, —C(O)—$C_{1-6}$ alkyl, or oxo;

(4) $C_{2-6}$ alkenyl,
(5) $C_{3-8}$ cycloalkyl which is:
  (a) optionally substituted with from 1 to 6 substituents each of which is independently —$C_{1-6}$ alkyl, —OH, —O—$C_{1-6}$ alkyl, or —$C_{1-6}$ haloalkyl, and
  (b) optionally substituted with:
    (i) aryl, which is optionally substituted with from 1 to 5 substituents each of which is independently halo, —$C_{1-6}$ alkyl, —O—$C_{1-6}$ alkyl, —$C_{1-6}$ haloalkyl, or —OH,
    (ii) heteroaryl, which is optionally substituted with from 1 to 4 substituents each of which is independently halogen, —$C_{1-6}$ alkyl, —$C_{1-6}$ haloalkyl, —O—$C_{1-6}$ alkyl, —O—$C_{1-6}$ haloalkyl, or —OH,
    (iii) heteromonocycle, which is
      (i) optionally substituted with from 1 to 6 substituents each of which is independently halogen, —$C_{1-6}$ alkyl, —$C_{1-6}$ haloalkyl, —O—$C_{1-6}$ alkyl, —O—$C_{1-6}$ haloalkyl, —C(O)—$C_{1-6}$ alkyl, or oxo, and
      (ii) optionally substituted with —$C_{1-6}$ alkylene-aryl, or
    (iv) N($R^A$)$R^B$,
(6) aryl, which is:
  (a) optionally substituted with from 1 to 5 substituents each of which is independently halo, —$C_{1-6}$ alkyl, —O—$C_{1-6}$ alkyl, —$C_{1-6}$ haloalkyl, or —OH, and
  (b) optionally substituted with (i) heteroaryl optionally substituted with from 1 to 3 substituents each of which is independently a —$C_{1-6}$ alkyl, or (ii) heteromonocycle optionally substituted with from 1 to 4 substituents each of which is independently —$C_{1-6}$ alkyl, —$C_{1-6}$ alkylene-aryl, or oxo,
(7) bicyclic or tricyclic carbocycle, which is optionally substituted with from 1 to 7 substituents each of which is independently halogen, —$C_{1-6}$ alkyl, —$C_{1-6}$ haloalkyl, OH, —O—$C_{1-6}$ alkyl, or —O—$C_{1-6}$ haloalkyl,
(8) heteroaryl, which is
  (a) optionally substituted with from 1 to 4 substituents each of which is independently halogen, —$C_{1-6}$ alkyl, —$C_{1-6}$ haloalkyl, —O—$C_{1-6}$ alkyl, —O—$C_{1-6}$ haloalkyl, or —OH, and
  (b) optionally substituted with (i) aryl or (ii) heteromonocycle optionally substituted with from 1 to 4 substituents each of which is independently —$C_{1-6}$ alkyl, —$C_{1-6}$ alkylene-aryl, or oxo,
(9) heteromonocycle, which is
  (a) optionally substituted with from 1 to 6 substituents each of which is independently halogen, —$C_{1-6}$ alkyl, —$C_{1-6}$ haloalkyl, —O—$C_{1-6}$ alkyl, —O—$C_{1-6}$ haloalkyl, —C(O)—$C_{1-6}$ alkyl, —C(O)C(O)N($R^A$)$R^B$, or oxo, and
  (b) optionally substituted with:
    (i) —$C_{1-6}$ alkylene-$C_{3-8}$ cycloalkyl,
    (ii) aryl,
    (iii) —$C_{1-6}$ alkylene-aryl,
    (iv) heteroaryl optionally substituted with from 1 to 3 substituents each of which is independently a —$C_{1-6}$ alkyl,
    (v) heteromonocycle optionally substituted with from 1 to 4 substituents each of which is independently —$C_{1-6}$ alkyl, —$C_{1-6}$ alkylene-aryl, or oxo, or
    (vi) —C(O)—$C_{1-6}$ alkylene-heteromonocycle wherein the heteromonocycle is optionally substituted with from 1 to 4 substituents each of which is independently —$C_{1-6}$ alkyl, —$C_{1-6}$ alkylene-aryl, or oxo, or
(10) bicyclic or tricyclic heterocycle, which is optionally substituted with from 1 to 7 substituents each of which is independently halogen, —$C_{1-6}$ alkyl, —$C_{1-6}$ haloalkyl, —O—$C_{1-6}$ alkyl, —O—$C_{1-6}$ haloalkyl, —C(O)—$C_{1-6}$ alkyl, or oxo;

$R^5$ is:
(1) H,
(2) $C_{1-6}$ alkyl,
(3) $C_{1-6}$ alkyl substituted with:
  (a) $C_{3-8}$ cycloalkyl, which is optionally substituted with from 1 to 5 substituents each of which is independently $C_{1-6}$ alkyl, halo, or —O—$C_{1-6}$ alkyl,
  (b) aryl, which is optionally substituted with from 1 to 5 substituents each of which is independently any one of substituents (1) to (21) as defined above in Part A of the definition of T,
  (c) HetB,
  (d) —N($R^A$)$R^B$,
  (e) —N($R^A$)—C(O)—$R^B$,
  (f) —N($R^A$)—SO$_2R^B$, or
  (g) —N($R^A$)—C(O)—C(O)—N($R^A$)$R^B$,
(4) C(O)$R^U$, or
(5) SO$_2R^V$;

$R^6$ is $C_{1-6}$ alkyl;
$R^7$ is $C_{1-6}$ alkyl, C(O)$R^U$, or SO$_2R^V$;

or alternatively $R^6$ and $R^7$ together with the nitrogen atom to which they are attached form a ring selected from the group consisting of:

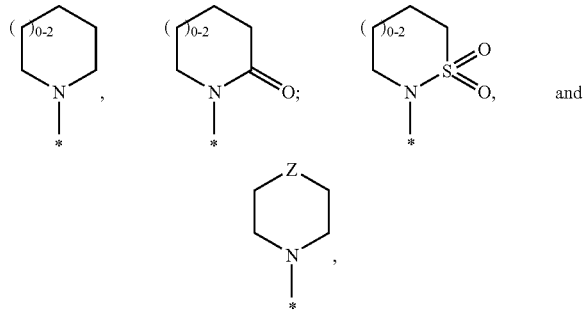

wherein the asterisk * denotes the point of attachment of the ring to the rest of the compound; and Z is O, S, S(O), S(O)$_2$, or N—$R^W$;

each HetA is independently a $C_{4-7}$ azacycloalkyl or a $C_{3-6}$ diazacycloalkyl, either of which is optionally substituted with from 1 to 4 substituents each of which is independently $C_{1-6}$ alkyl or oxo;

each HetB is independently a 5- or 6-membered heteroaromatic ring containing from 1 to 4 heteroatoms independently selected from N, O and S, wherein the heteroaromatic ring is optionally substituted with from 1 to 4 substituents each of which is independently halo, —$C_{1-6}$ alkyl, —$C_{1-6}$ haloalkyl, —O—$C_{1-6}$ alkyl, —O—$C_{1-6}$ haloalkyl, or —OH;

each aryl is independently phenyl, indenyl, indanyl, naphthyl, or tetrahydronaphthyl;

each bicyclic carbocycle is independently a bridged or fused two-ring system containing from 7 to 11 carbons, in which each ring is either saturated or unsaturated, but neither ring is aromatic;

each tricyclic carbocycle is independently a bridged or fused or bridged and fused three-ring system containing from 8 to 12 carbons, in which each ring is either saturated or unsaturated, but no ring is aromatic;

each heteroaryl is independently (i) a 5- or 6-membered heteroaromatic ring containing from 1 to 4 heteroatoms independently selected from N, O and S or (ii) a 8- or 12-membered bicyclic, fused ring system containing from 1 to 4 heteroatoms independently selected from N, O and S, wherein one or both of the rings in the ring system contain at least one heteroatom, at least one ring is aromatic, and any S atom in a ring which is not aromatic is optionally present in the form of a monoxide or dioxide;

each heteromonocycle is independently a 4- to 7-membered saturated or mono-unsaturated heterocyclic ring containing at least one carbon atom and from 1 to 4 heteroatoms independently selected from N, O and S;

each bicyclic heterocycle is independently a 7- to 11-membered bridged or fused two-ring system containing from 1 to 4 heteroatoms independently selected from N, O and S, in which each ring is either saturated or unsaturated, but neither ring is aromatic, and one or both rings in the ring system contain at least one heteroatom;

each tricyclic heterocycle is independently an 8- to 12-membered bridged or fused or bridged and fused three-ring system containing from 1 to 4 heteroatoms independently selected from N, O and S, in which each ring is either saturated or unsaturated, but no ring is an aromatic, and one or two or all three of the rings contain at least one heteroatom;

each $R^A$ is independently H or $C_{1-6}$ alkyl;

each $R^B$ is independently H or $C_{1-6}$ alkyl;

each $R^C$ is independently H, $C_{1-6}$ alkyl, or $C_{1-6}$ alkyl substituted with aryl or OH;

each $R^D$ is independently H, $C_{1-6}$ alkyl, or $C_{1-6}$ alkyl substituted with aryl or OH;

each $R^E$ is independently H, $C_{1-6}$ alkyl, or $C_{1-6}$ alkyl substituted with aryl;

each $R^F$ is independently O—$C_{1-6}$ alkyl, $SO_2$—$C_{1-6}$ alkyl, $SO_2$-aryl, $SO_2$—N($R^C$)$R^D$, C(O)—$C_{1-6}$ alkyl, C(O)-aryl, C(O)—N($R^C$)$R^D$, C(S)—$C_{1-6}$ alkyl, C(S)-aryl, or C(S)—N($R^C$)$R^D$;

$R^U$ is $C_{1-6}$ alkyl, O—$C_{1-6}$ alkyl, $C_{3-8}$ cycloalkyl, $C_{1-6}$ alkyl substituted with $C_{3-8}$ cycloalkyl, N($R^A$)$R^B$, or C(O)—N($R^A$)$R^B$;

$R^V$ is $C_{1-6}$ alkyl, $C_{3-8}$ cycloalkyl, $C_{1-6}$ alkyl substituted with $C_{3-8}$ cycloalkyl, or N($R^A$)$R^B$; and $R^W$ is H, $C_{1-6}$ alkyl, $C_{3-8}$ cycloalkyl, $C_{1-6}$ alkyl substituted with $C_{3-8}$ cycloalkyl, C(O)$R^U$, or $SO_2R^V$.

The present invention also includes pharmaceutical compositions containing a compound of the present invention and methods of preparing such pharmaceutical compositions. The present invention further includes methods of treating AIDS, methods of delaying the onset of AIDS, methods of preventing AIDS, methods of preventing infection by HIV, and methods of treating infection by HIV.

Other embodiments, aspects and features of the present invention are either further described in or will be apparent from the ensuing description, examples and appended claims.

DETAILED DESCRIPTION OF THE INVENTION

The present invention includes compounds of Formula I above, and pharmaceutically acceptable salts thereof. These compounds and pharmaceutically acceptable salts thereof are HIV integrase inhibitors.

A first embodiment of the present invention is a compound of Formula I, or a pharmaceutically acceptable salt thereof, wherein $R^1$ is $CH_2$-T; and all other variables are as originally defined (i.e., as defined in the Summary of the Invention).

A second embodiment of the present invention is a compound of Formula I, or a pharmaceutically acceptable salt thereof, wherein $R^1$ is $CH_2$-T; T is:

(1) phenyl, which is (i) optionally substituted with from 1 to 4 substituents each of which is independently halo, —$C_{1-4}$ alkyl, —O—$C_{1-4}$ alkyl, —$C_{1-4}$ fluoroalkyl, CN, —$SO_2$—$C_{1-4}$ alkyl, —C(=O)—NH(—$C_{1-4}$ alkyl), or —C(=O)—N(—$C_{1-4}$ alkyl)$_2$, and (ii) optionally substituted with from 1 to 3 HetB;

(3) naphthyl, which is optionally substituted with from 1 to 4 substituents each of which is independently halo, —$C_{1-4}$ alkyl, —O—$C_{1-4}$ alkyl, or —$C_{1-4}$ fluoroalkyl, (3) pyridyl, which is optionally substituted with from 1 to 3 substituents each of which is independently halogen, —$C_{1-4}$ alkyl, —$C_{1-4}$ haloalkyl, —O—$C_{1-4}$ alkyl, —O—$C_{1-4}$ haloalkyl, or —OH, or (4) quinolinyl or isoquinolinyl, which is optionally substituted with from 1 to 3 substituents each of which is independently halogen, —$C_{1-4}$ alkyl, —$C_{1-4}$ haloalkyl, —O—$C_{1-4}$ alkyl, —O—$C_{1-4}$ haloalkyl, or —OH;

and all other variables are as originally defined.

A third embodiment of the present invention is a compound of Formula I, or a pharmaceutically acceptable salt thereof, wherein $R^1$ is $CH_2$-T; T is:

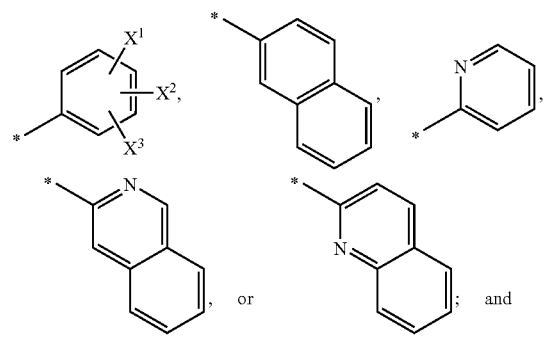

wherein the asterisk * denotes the point of attachment to the rest of the compound;

$X^1$, $X^2$ and $X^3$ are each independently selected from the group consisting of —H, halo, —$C_{1-4}$ alkyl, —O—$C_{1-4}$ alkyl, —$C_{1-4}$ fluoroalkyl, CN, —$SO_2$—$C_{1-4}$ alkyl, —C(=O)—NH(—$C_{1-4}$ alkyl), —C(=O)—N(—$C_{1-4}$ alkyl)$_2$, and HetB;

and all other variables are as originally defined.

In an aspect of the second and third embodiments, each HetB is independently a 5- or 6-membered heteroaromatic ring containing from 1 to 4 heteroatoms independently selected from N, O and S, wherein the heteroaromatic ring is optionally substituted with from 1 to 4 substituents each of which is independently halo, —$C_{1-4}$ alkyl, —$C_{1-4}$ haloalkyl, —O—$C_{1-4}$ alkyl, —O—$C_{1-4}$ haloalkyl, or —OH.

A fourth embodiment of the present invention is a compound of Formula I, or a pharmaceutically acceptable salt thereof, wherein $R^1$ is $CH_2$-T; T is:

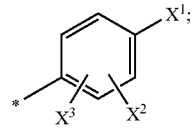

$X^1$ is fluoro, chloro, methyl, trifluoromethyl, or methoxy;
$X^2$ and $X^3$ are each independently selected from the group consisting of —H, fluoro, chloro, methyl, trifluoromethyl, methoxy, —$SO_2CH_3$, —C(=O)—NH($CH_3$), —C(=O)—N($CH_3$)$_2$, and oxadiazolyl;

and all other variables are as originally defined.

A fifth embodiment of the present invention is a compound of Formula I, or a pharmaceutically acceptable salt thereof, wherein $R^1$ is $CH_2$-T; T is 4-fluorophenyl; and all other variables are as originally defined.

A sixth embodiment of the present invention is a compound of Formula I, or a pharmaceutically acceptable salt thereof, wherein $R^2$ is:
(1) H,
(2) $C_{1-5}$ alkyl, or
(3) $C_{1-3}$ alkyl substituted with —$CO_2R^A$ or —C(O)N($R^C$)$R^D$;

and all other variables are as originally defined or as defined in any one of the preceding embodiments.

A seventh embodiment of the present invention is a compound of Formula I, or a pharmaceutically acceptable salt thereof, wherein $R^2$ is:
(1) H,
(2) $C_{1-3}$ alkyl,
(3) ($CH_2$)$_{1-2}$—$CO_2R^A$, or
(4) ($CH_2$)$_{1-2}$—C(O)N($R^C$)$R^D$;

and all other variables are as originally defined or as defined in any one of the preceding embodiments.

An eighth embodiment of the present invention is a compound of Formula I, or a pharmaceutically acceptable salt thereof, wherein $R^2$ is: (1) H, (2) $CH_2$—C(O)NH($CH_3$), or (3) $CH_2$—C(O)N($CH_3$)$_2$; and all other variables are as originally defined or as defined in any one of the preceding embodiments.

A ninth embodiment of the present invention is a compound of Formula I, or a pharmaceutically acceptable salt thereof, wherein $R^2$ is H; and all other variables are as originally defined or as defined in any one of the preceding embodiments.

A tenth embodiment of the present invention is a compound of Formula I, or a pharmaceutically acceptable salt thereof, wherein $R^3$ is:
(1) H,
(2) $C_{1-5}$ alkyl, or
(3) $C_{1-3}$ alkyl substituted with:
 (a) —OH,
 (b) —O—$C_{1-4}$ alkyl,
 (c) —$NH_2$,
 (d) —NH($C_{1-4}$ alkyl),
 (e) —N($C_{1-4}$ alkyl)$_2$,
 (f) —N(O—$C_{1-4}$ alkyl)-$C_{1-4}$ alkyl,
 (g) —NH—$CH_2$-phenyl,
 (h) —N($C_{1-4}$ alkyl)-$CH_2$-phenyl,
 (i) —NH—C(O)—$C_{1-4}$ alkyl,
 (j) —N($C_{1-4}$ alkyl)-C(O)—$C_{1-4}$ alkyl,
 (k) —NH—C(O)-phenyl,
 (l) —N($C_{1-4}$ alkyl)-C(O)-phenyl,
 (m) —NH—C(O)N($C_{1-4}$ alkyl)$_2$,
 (n) —N($C_{1-4}$ alkyl)-C(O)NH($C_{1-4}$ alkyl),
 (o) —N($C_{1-4}$ alkyl)-C(O)N($C_{1-4}$ alkyl)$_2$,
 (p) —NH—C(S)N($C_{1-4}$ alkyl)$_2$,
 (q) —N($C_{1-4}$ alkyl)-C(S)NH($C_{1-4}$ alkyl),
 (r) —N($C_{1-4}$ alkyl)-C(S)N($C_{1-4}$ alkyl)$_2$,
 (s) —NH—$SO_2$—$C_{1-4}$ alkyl,
 (t) —N($C_{1-4}$ alkyl)-$SO_2$—$C_{1-4}$ alkyl,
 (u) phenyl, which is optionally substituted with from 1 to 4 substituents each of which is independently halo, —$C_{1-4}$ alkyl, —O—$C_{1-4}$ alkyl, or —$C_{1-4}$ fluoroalkyl,
 (v) —O—$C_{1-3}$ alkylene-phenyl, in which the phenyl is optionally substituted with from 1 to 4 substituents each of which is independently halo, —$C_{1-4}$ alkyl, —O—$C_{1-4}$ alkyl, or —$C_{1-4}$ fluoroalkyl,
 (w) HetC, which is a 5- or 6-membered heteroaromatic ring containing from 1 to 4 heteroatoms independently selected from N, O and S, which is optionally substituted with from 1 to 4 substituents each of which is independently halogen, —$C_{1-4}$ alkyl, —$C_{1-4}$ fluoroalkyl, —O—$C_{1-4}$ alkyl, —O—$C_{1-4}$ fluoroalkyl, or —OH,
 (x) HetD, which is a 4- to 7-membered saturated heterocyclic ring containing at least one carbon atom and from 1 to 4 heteroatoms independently selected from N, O and S, which is optionally substituted with from 1 to 6 substituents each of which is independently halogen, —$C_{1-4}$ alkyl, —$C_{1-4}$ fluoroalkyl, —O—$C_{1-4}$ alkyl, —O—$C_{1-6}$ fluoroalkyl, or oxo, or
 (y) HetE, which is a 4- to 7-membered saturated heterocyclic ring fused to a benzene ring, wherein the saturated heterocyclic ring contains at least one carbon atom and from 1 to 3 heteroatoms independently selected from N, O and S, wherein the benzo heterocyclic ring system is optionally substituted with from 1 to 6 substituents each of which is independently halogen, —$C_{1-4}$ alkyl, —$C_{1-4}$ fluoroalkyl, —O—$C_{1-4}$ alkyl, —O—$C_{1-6}$ fluoroalkyl, or oxo;

and all other variables are as originally defined or as defined in any one of the preceding embodiments.

An eleventh embodiment of the present invention is a compound of Formula I, or a pharmaceutically acceptable salt thereof, wherein $R^3$ is:
(1) H,
(2) $C_{1-5}$ alkyl,
(3) ($CH_2$)$_{1-2}$—OH,
(4) ($CH_2$)$_{1-2}$—O—$C_{1-4}$ alkyl,
(5) ($CH_2$)$_{1-2}$—$NH_2$,
(6) ($CH_2$)$_{1-2}$—NH($C_{1-4}$ alkyl),
(7) ($CH_2$)$_{1-2}$—N($C_{1-4}$ alkyl)$_2$,
(8) ($CH_2$)$_{1-2}$—N(O—$C_{1-4}$ alkyl)-$C_{1-4}$ alkyl,
(9) ($CH_2$)$_{1-2}$—NH—$CH_2$-phenyl,
(10) ($CH_2$)$_{1-2}$—N($CH_3$)—$CH_2$-phenyl,
(11) ($CH_2$)$_{1-2}$—NH—C(O)—$C_{1-4}$ alkyl,
(12) ($CH_2$)$_{1-2}$—N($CH_3$)—C(O)—$C_{1-4}$ alkyl,
(13) ($CH_2$)$_{1-2}$—NH—C(O)-phenyl,

(14) (CH$_2$)$_{1-2}$—N(CH$_3$)—C(O)-phenyl,
(15) (CH$_2$)$_{1-2}$—NH—C(O)N(C$_{1-4}$ alkyl)$_2$,
(16) (CH$_2$)$_{1-2}$—N(CH$_3$)—C(O)NH(C$_{1-4}$ alkyl),
(17) (CH$_2$)$_{1-2}$—N(CH$_3$)—C(O)N(C$_{1-4}$ alkyl)$_2$,
(18) (CH$_2$)$_{1-2}$—NH—C(S)N(C$_{1-4}$ alkyl)$_2$,
(19) (CH$_2$)$_{1-2}$—N(CH$_3$)—C(S)NH(C$_{1-4}$ alkyl),
(20) (CH$_2$)$_{1-2}$—N(CH$_3$)—C(S)N(C$_{1-4}$ alkyl)$_2$,
(21) (CH$_2$)$_{1-2}$—NH—SO$_2$—C$_{1-4}$ alkyl,
(22) (CH$_2$)$_{1-2}$—N(CH$_3$)—SO$_2$—C$_{1-4}$ alkyl,
(23) (CH$_2$)$_{1-2}$-phenyl,
(24) (CH$_2$)$_{1-2}$—OCH$_2$-phenyl,
(25) (CH$_2$)$_{1-2}$-HetC, where HetC is a heteroaromatic ring selected from the group consisting of pyridyl, pyrrolyl, pyrazinyl, pyrimidinyl, pyridazinyl, triazinyl, thienyl, furanyl, imidazolyl, pyrazolyl, triazolyl, tetrazolyl, oxazolyl, isooxazolyl, oxadiazolyl, oxatriazolyl, thiazolyl, isothiazolyl, and thiadiazolyl, wherein the heteroaromatic ring is optionally substituted with 1 or 2 substituents each of which is independently halo or a C$_{1-4}$ alkyl,
(26) (CH$_2$)$_{1-2}$-HetD, where HetD is a saturated heterocyclic ring selected from the group consisting of piperidinyl, morpholinyl, thiomorpholinyl, thiazolidinyl, isothiazolidinyl, oxazolidinyl, isoxazolidinyl, pyrrolidinyl, imidazolidinyl, piperazinyl, tetrahydrofuranyl, tetrahydrothienyl, pyrazolidinyl, hexahydropyrimidinyl, thiazinanyl, thiazepanyl, thiadiazepanyl, dithiazepanyl, azepanyl, diazepanyl, thiadiazinanyl, tetrahydropyranyl, tetrahydrothiopyranyl, and dioxanyl; wherein the saturated heterocyclic ring is optionally substituted with from 1 to 4 substituents each of which is independently oxo or a C$_{1-4}$ alkyl, or
(27) (CH$_2$)$_{1-2}$-HetE, where HetE is benzopiperidinyl; and all other variables are as originally defined or as defined in any one of the preceding embodiments.

In an aspect of the tenth and eleventh embodiments, HetD and HetE are each independently as defined therein, with the further proviso that any ring nitrogen in HetD or HetE forms a tertiary amine formed by direct attachment of the nitrogen to the carbon in the alkyl moiety or by substitution of the alkyl group on the nitrogen, and any ring S is optionally in the form of a monoxide or a dioxide (i.e., S(O) or S(O)$_2$). Thus, for example, in this aspect of the eleventh embodiment, when R$^3$ is (CH$_2$)$_{1-2}$-HetD and HetD is piperidinyl mono-substituted with alkyl, R$^3$ is:

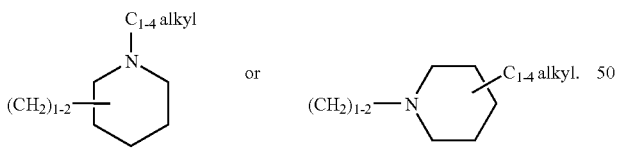

A twelfth embodiment of the present invention is a compound of Formula I, or a pharmaceutically acceptable salt thereof, wherein R$^3$ is H; and all other variables are as originally defined or as defined in any one of the preceding embodiments.

A thirteenth embodiment of the present invention is a compound of Formula I, or a pharmaceutically acceptable salt thereof, wherein Y is O, S, or NR$^5$ when bond "a" is a single bond; R$^5$ is: (1) H, (2) C$_{1-5}$ alkyl, or (3) (CH$_2$)$_{1-3}$-phenyl, where the phenyl is optionally substituted with from 1 to 4 substituents each of which is independently halo, —C$_{1-4}$ alkyl, —O—C$_{1-4}$ alkyl, —C$_{1-4}$ fluoroalkyl, —SO$_2$—C$_{1-4}$ alkyl, —C(=O)—NH(—C$_{1-4}$ alkyl), or —C(=O)—N(—C$_{1-4}$ alkyl)$_2$; and all other variables are as originally defined or as defined in any one of the preceding embodiments.

A fourteenth embodiment of the present invention is a compound of Formula I, or a pharmaceutically acceptable salt thereof, wherein Y is O, S, or NR$^5$ when bond "a" is a single bond; R$^5$ is H, C$_{1-5}$ alkyl, or benzyl; and all other variables are as originally defined or as defined in any one of the preceding embodiments.

A fifteenth embodiment of the present invention is a compound of Formula I, or a pharmaceutically acceptable salt thereof, wherein Y is O when bond "a" is a single bond; and all other variables are as originally defined or as defined in any one of the preceding embodiments.

A sixteenth embodiment of the present invention is a compound of Formula I, or a pharmaceutically acceptable salt thereof, wherein R$^4$ is as follows when bond "a" is a single bond:
(1) H,
(2) C$_{1-5}$ alkyl,
(3) C$_{1-5}$ alkyl substituted with 1 or 2 substituents each of which is independently:
 (a) —OH,
 (b) —O—C$_{1-4}$ alkyl,
 (c) —C$_{1-4}$ fluoroalkyl containing at least one CF$_3$ group,
 (d) —CO$_2$—C$_{1-4}$ alkyl,
 (e) —C(O)NH$_2$,
 (f) —C(O)NH(C$_{1-4}$ alkyl),
 (g) —C(O)N(C$_{1-4}$ alkyl)$_2$,
 (h) —C(O)C(O)N(C$_{1-4}$ alkyl)$_2$,
 (i) —S—C$_{1-4}$ alkyl,
 (j) —S-phenyl,
 (k) —S(O)—C$_{1-4}$ alkyl,
 (l) —SO$_2$—C$_{1-4}$ alkyl,
 (m) —NH$_2$,
 (n) —NH(C$_{1-4}$ alkyl),
 (o) —N(C$_{1-4}$ alkyl)$_2$,
 (p) —NH(CH$_2$-phenyl),
 (q) —N(C$_{1-4}$ alkyl)-CH$_2$-phenyl,
 (r) —NH—C(O)—C$_{1-4}$ alkyl,
 (s) —N(C$_{1-4}$ alkyl)-C(O)—C$_{1-4}$ alkyl,
 (t) —NH—C(O)N(C$_{1-4}$ alkyl)$_2$,
 (u) —N(C$_{1-4}$ alkyl)-C(O)N(C$_{1-4}$ alkyl)$_2$,
 (v) —NH—SO$_2$—C$_{1-4}$ alkyl,
 (w) —N(C$_{1-4}$ alkyl)-SO$_2$—C$_{1-4}$ alkyl,
 (x) —C$_{3-6}$ cycloalkyl, which is:
  (i) optionally substituted with from 1 to 4 substituents each of which is independently —C$_{1-4}$ alkyl, —OH, —O—C$_{1-4}$ alkyl, or —C$_{1-4}$ fluoroalkyl containing at least one CF$_3$ group, and
  (ii) optionally substituted with phenyl, benzyl, HetF, or HetG,
 (y) aryl selected from the group consisting of phenyl and napthyl, wherein the aryl is:
  (i) optionally substituted with from 1 to 4 substituents each of which is independently halo, —C$_{1-4}$ alkyl, —O—C$_{1-4}$ alkyl, —C$_{1-4}$ fluoroalkyl containing at least one CF$_3$, or —OH, and
  (ii) optionally substituted with HetF or HetG,
 (z) a bridged carbocycle which is bicyclo[2.2.1]heptyl, bicyclo[2.2.2]octyl, or adamantyl, wherein the bridged carbocycle is optionally substituted with from 1 to 4 substituents each of which is independently a —C$_{1-4}$ alkyl or OH,
 (aa) a 5- or 6-membered heteroaromatic ring containing from 1 to 4 heteroatoms independently selected from N, O and S, which is:

(i) optionally substituted with from 1 to 3 substituents each of which is independently a halo, —$C_{1-4}$ alkyl, —O—$C_{1-4}$ alkyl, or —$CF_3$, and (ii) optionally substituted with phenyl, benzyl, or HetG, (bb) a 9- or 10-membered fused heterobicyclic aromatic ring system containing from 1 to 4 nitrogen atoms in which one or both rings in the ring system contains at least one nitrogen atom and at least one ring is aromatic, wherein the ring system is optionally substituted with from 1 to 3 substituents each of which is independently a —$C_{1-4}$ alkyl group, or (cc) a 4- to 7-membered saturated heterocyclic ring containing at least one carbon atom and from 1 to 4 heteroatoms independently selected from N, O and S, which is:

(i) optionally substituted with from 1 to 4 substituents each of which is independently halogen, —$C_{1-4}$ alkyl, —$CF_3$, —C(O)—$C_{1-4}$ alkyl, —C(O)C(O)N($C_{1-4}$ alkyl)$_2$, or oxo, and (ii) optionally substituted with $CH_2$—$C_{3-6}$ cycloalkyl, phenyl, benzyl, HetF, HetG, or —C(O)$CH_2$-HetG, or (dd) a fused or bridged heterocycle, which is 1-azabicyclo[2.2.2]octyl, 1-azabicyclo[2.2.1]heptyl, or 1-azabicyclo[4.4.0]decyl, where the fused or bridged heterocycle is optionally substituted with from 1 to 7 substituents each of which is independently a —$C_{1-4}$ alkyl, (4) $C_{2-4}$ alkenyl, (5) $C_{3-7}$ cycloalkyl which is:

(a) optionally substituted with from 1 to 4 substituents each of which is independently —$C_{1-4}$ alkyl, —OH, —O—$C_{1-4}$ alkyl, or —$C_{1-4}$ fluoroalkyl containing at least one $CF_3$, and (b) optionally substituted with:

(i) phenyl, which is optionally substituted with from 1 to 4 substituents each of which is independently halo, —$C_{1-4}$ alkyl, —O—$C_{1-4}$ alkyl, —$C_{1-4}$ fluoroalkyl containing at least one $CF_3$ group, or —OH, (ii) a 5- or 6-membered heteroaromatic ring containing from 1 to 4 heteroatoms independently selected from N, O and S, which is optionally substituted with from 1 to 3 substituents each of which is independently a halo, —$C_{1-4}$ alkyl, —O—$C_{1-4}$ alkyl, or —$CF_3$, or (iii) a 4- to 7-membered saturated heterocyclic ring containing at least one carbon atom and from 1 to 4 heteroatoms independently selected from N, O and S, which is:

(i) optionally substituted with from 1 to 4 substituents each of which is independently halogen, —$C_{1-4}$ alkyl, —$CF_3$, —C(O)—$C_{1-4}$ alkyl, or oxo, and (ii) optionally substituted with benzyl, (iv)) NH($C_{1-4}$ alkyl), or (v) N($C_{1-4}$ alkyl)$_2$, (6) aryl selected from the group consisting of phenyl, naphthyl and indanyl, where the phenyl is (i) optionally substituted with from 1 to 4 substituents each of which is independently halo, —$C_{1-4}$ alkyl, —O—$C_{1-4}$ alkyl, —$C_{1-4}$ fluoroalkyl containing at least one $CF_3$ group, or —OH, and (ii) optionally substituted with HetF or HetG, (7) a bridged carbocycle which is bicyclo[2.2.1]heptyl, bicyclo[2.2.2]octyl, or adamantyl, wherein the bridged carbocycle is optionally substituted with from 1 to 4 substituents each of which is independently a —$C_{1-4}$ alkyl or OH, (8) heteroaryl which is (i) a 5- or 6-membered heteroaromatic ring containing from 1 to 4 heteroatoms independently selected from N, O and S, which is (a) optionally substituted with from 1 to 3 substituents each of which is independently a halo, —$C_{1-4}$ alkyl, —O—$C_{1-4}$ alkyl, —$C_{1-4}$ fluoroalkyl containing at least one $CF_3$ group and (b) optionally substituted with phenyl or HetG, or (ii) a 4- to 7-membered saturated heterocyclic ring fused to a benzene ring, wherein the heterocyclic ring contains at least one carbon atom and from 1 to 3 heteroatoms independently selected from N, O and S, wherein any S atom in the ring is optionally in the form of a monoxide or dioxide, and wherein the benzo-heterocyclic ring is optionally substituted with from 1 to 4 substituents each of which is independently halogen, —$C_{1-4}$ alkyl, —$CF_3$, (9) heteromonocycle, which is a 4- to 7-membered saturated heterocyclic ring containing at least one carbon atom and from 1 to 4 heteroatoms independently selected from N, O and S, which is (i) optionally substituted with from 1 to 6 substituents each of which is independently halogen, —$C_{1-4}$ alkyl, —$CF_3$, —C(O)—$C_{1-4}$ alkyl, —C(O)C(O)N($C_{1-4}$ alkyl)$_2$, or oxo, and (b) optionally substituted with $CH_2$—$C_{3-6}$ cycloalkyl, phenyl, benzyl, HetF, HetG, or —C(O)$CH_2$-HetG, or

(10) a fused or bridged heterocycle, which is 1-azabicyclo[2.2.2]octyl, 1-azabicyclo[2.2.1]heptyl, or 1-azabicyclo[4.4.0]decyl, where the fused or bridged heterocycle is optionally substituted with from 1 to 7 substituents each of which is independently a —$C_{1-4}$ alkyl;

HetF is a 5- or 6-membered heteroaromatic ring containing from 1 to 4 heteroatoms independently selected from N, O and S, which is optionally substituted with from 1 to 3 substituents each of which is independently a —$C_{1-4}$ alkyl;

HetG is a 4- to 7-membered saturated heterocyclic ring containing at least one carbon atom and from 1 to 4 heteroatoms independently selected from N, O and S, which is optionally substituted with from 1 to 4 substituents each of which is independently —$C_{1-4}$ alkyl, —$CH_2$-phenyl, or oxo;

and all other variables are as originally defined or as defined in any one of the preceding embodiments.

A seventeenth embodiment of the present invention is a compound of Formula I, or a pharmaceutically acceptable salt thereof, wherein each $R^A$ and $R^B$ is independently H or $C_{1-3}$ alkyl; and all other variables are as originally defined or as defined in any one of the preceding embodiments.

An eighteenth embodiment of the present invention is a compound of Formula I, or a pharmaceutically acceptable salt thereof, wherein each $R^A$ and $R^B$ is independently H or methyl; and all other variables are as originally defined or as defined in any one of the preceding embodiments.

A nineteenth embodiment of the present invention is a compound of Formula I, or a pharmaceutically acceptable salt thereof, wherein each $R^C$ and $R^D$ is independently H, $C_{1-5}$ alkyl, or $C_{1-4}$ alkyl substituted with phenyl or OH; and all other variables are as originally defined or as defined in any one of the preceding embodiments.

A twentieth embodiment of the present invention is a compound of Formula I, or a pharmaceutically acceptable salt thereof, wherein each $R^C$ and $R^D$ is independently H, $C_{1-3}$ alkyl, $C_{1-3}$ alkylene-OH, or benzyl; and all other variables are as originally defined or as defined in any one of the preceding embodiments.

A twenty-first embodiment of the present invention is a compound of Formula I, or a pharmaceutically acceptable salt thereof, wherein each $R^E$ is independently H, $C_{1-5}$ alkyl, or $C_{1-4}$ alkyl substituted with phenyl; and all other variables are as originally defined or as defined in any one of the preceding embodiments.

A twenty-second embodiment of the present invention is a compound of Formula I, or a pharmaceutically acceptable salt thereof, wherein each $R^E$ is independently H, $C_{1-3}$ alkyl, or benzyl; and all other variables are as originally defined or as defined in any one of the preceding embodiments.

A twenty-third embodiment of the present invention is a compound of Formula I, or a pharmaceutically acceptable salt thereof, wherein each $R^F$ is independently O—$C_{1-3}$ alkyl, $SO_2$—$C_{1-3}$ alkyl, $SO_2$-phenyl, $SO_2$—$N(R^C)R^D$, $C(O)$—$C_{1-3}$ alkyl, $C(O)$-phenyl, $C(O)$—$N(R^C)R^D$, $C(S)$—$C_{1-3}$ alkyl, $C(S)$-phenyl, or $C(S)$—$N(R^C)R^D$; and all other variables are as originally defined or as defined in any one of the preceding embodiments. In an aspect of this embodiment, $R^C$ and $R^D$ are as defined in the nineteenth embodiment.

A twenty-fourth embodiment of the present invention is a compound of Formula I, or a pharmaceutically acceptable salt thereof, wherein each $R^F$ is independently $OCH_3$, $SO_2CH_3$, $SO_2$-phenyl, $SO_2$—$N(R^C)R^D$, $C(O)CH_3$, $C(O)$-phenyl, $C(O)$—$N(R^C)R^D$, $C(S)CH_3$, $C(S)$-phenyl, or $C(S)$—$N(R^C)R^D$; and all other variables are as originally defined or as defined in any one of the preceding embodiments. In an aspect of this embodiment, $R^C$ and $R^D$ are as defined in the twentieth embodiment.

A twenty-fifth embodiment of the present invention is a compound of Formula I, or a pharmaceutically acceptable salt thereof, wherein $R^U$ is $C_{1-3}$ alkyl, O—$C_{1-3}$ alkyl, $C_{3-6}$ cycloalkyl, $C_{1-3}$ alkyl substituted with $C_{3-6}$ cycloalkyl, $N(R^A)R^B$, or $C(O)$—$N(R^A)R^B$; and all other variables are as originally defined or as defined in any one of the preceding embodiments. In an aspect of this embodiment, $R^A$ and $R^B$ are as defined in the seventeenth embodiment.

A twenty-sixth embodiment of the present invention is a compound of Formula I, or a pharmaceutically acceptable salt thereof, wherein $R^U$ is methyl, ethyl, $OCH_3$, cyclopropyl, $CH_2$-cyclopropyl, $N(R^A)R^B$, or $C(O)$—$N(R^A)R^B$; and all other variables are as originally defined or as defined in any one of the preceding embodiments. In an aspect of this embodiment, $R^A$ and $R^B$ are as defined in the eighteenth embodiment.

A twenty-seventh embodiment of the present invention is a compound of Formula I, or a pharmaceutically acceptable salt thereof, wherein $R^V$ is $C_{1-3}$ alkyl, $C_{3-6}$ cycloalkyl, $C_{1-3}$ alkyl substituted with $C_{3-6}$ cycloalkyl, or $N(R^A)R^B$; and all other variables are as originally defined or as defined in any one of the preceding embodiments. In an aspect of this embodiment, $R^A$ and $R^B$ are as defined in the seventeenth embodiment.

A twenty-eighth embodiment of the present invention is a compound of Formula I, or a pharmaceutically acceptable salt thereof, wherein $R^V$ is methyl, ethyl, cyclopropyl, $CH_2$-cyclopropyl, or $N(R^A)R^B$; and all other variables are as originally defined or as defined in any one of the preceding embodiments. In an aspect of this embodiment, $R^A$ and $R^B$ are as defined in the eighteenth embodiment.

A twenty-ninth embodiment of the present invention is a compound of Formula I, or a pharmaceutically acceptable salt thereof, wherein $R^W$ is H, $C_{1-3}$ alkyl, $C_{3-6}$ cycloalkyl, $C_{1-3}$ alkyl substituted with $C_{3-6}$ cycloalkyl, $C(O)R^U$, or $SO_2R^V$; and all other variables are as originally defined or as defined in any one of the preceding embodiments. In an aspect of this embodiment, $R^U$ and $R^V$ are as defined in the twenty fifth and twenty seventh embodiments respectively.

A thirtieth embodiment of the present invention is a compound of Formula I, or a pharmaceutically acceptable salt thereof, wherein $R^W$ is H, methyl, ethyl, cyclopropyl, $CH_2$-cyclopropyl, $C(O)R^U$, or $SO_2R^V$; and all other variables are as originally defined or as defined in any one of the preceding embodiments. In an aspect of this embodiment, $R^U$ and $R^V$ are as defined in the twenty sixth and twenty eighth embodiments respectively.

A thirty-first embodiment of the present invention is a compound of Formula I, or a pharmaceutically acceptable salt thereof, which is a compound of Formula II:

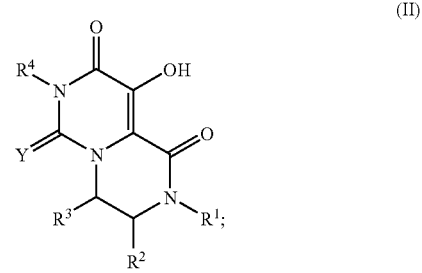

(II)

wherein all of the variables are as originally defined or as defined in any one of the preceding embodiments.

A thirty-first embodiment of the present invention is a compound of Formula I, or a pharmaceutically acceptable salt thereof, which is a compound of Formula III:

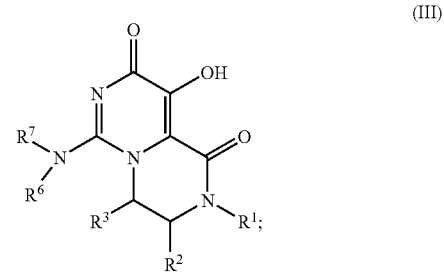

(III)

wherein all of the variables are as originally defined or as defined in any one of the preceding embodiments.

A first class of the present invention includes compounds of Formula II, and pharmaceutically acceptable salts thereof, wherein:

Y is O, S or $NR^5$;

$R^1$ is $CH_2T$, wherein T is:
(1) phenyl which is optionally substituted with from 1 to 3 substituents each of which is independently fluoro, chloro, methyl, trifluoromethyl, methoxy, CN, —$SO_2CH_3$, —$C(=O)NH(CH_3)$, or —$C(=O)N(CH_3)_2$,
(2) naphthyl,
(3) pyridyl,
(4) isoquinolinyl, or
(5) quinolinyl;

$R^2$ is H, $C_{1-3}$ alkyl, $(CH_2)_{1-2}$—$CO_2CH_3$, $(CH_2)_{1-2}$—$C(O)NH$—$CH_3$, or $(CH_2)_{1-2}$—$C(O)N(CH_3)_2$;

or alternatively R¹ and R² together with the nitrogen ring atom and carbon ring atom to which each is respectively attached form a ring of formula:

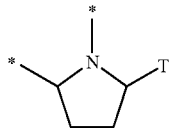

wherein T is as defined above and the asterisks * denote the points of attachment of the ring to the rest of the compound;
R³ is
  (1) H,
  (2) $C_{1-3}$ alkyl,
  (3) $(CH_2)_{1-2}$—OH,
  (4) $(CH_2)_{1-2}$—OCH$_3$,
  (5) $(CH_2)_{1-2}$—NH$_2$,
  (6) $(CH_2)_{1-2}$—NH(CH$_3$),
  (7) $(CH_2)_{1-2}$—N(CH$_3$)$_2$,
  (8) $(CH_2)_{1-2}$—N(OCH$_3$)CH$_3$,
  (9) $(CH_2)_{1-2}$—NH—CH$_2$-phenyl,
  (10) $(CH_2)_{1-2}$—N(CH$_3$)—CH$_2$-phenyl,
  (11) $(CH_2)_{1-2}$—NH—C(O)CH$_3$,
  (12) $(CH_2)_{1-2}$—N(CH$_3$)—C(O)CH$_3$,
  (13) $(CH_2)_{1-2}$—NH—C(O)C(CH$_3$)$_3$,
  (14) $(CH_2)_{1-2}$—N(CH$_3$)—C(O)C(CH$_3$)$_3$,
  (15) $(CH_2)_{1-2}$—NH—C(O)-phenyl,
  (16) $(CH_2)_{1-2}$—N(CH$_3$)—C(O)-phenyl,
  (17) $(CH_2)_{1-2}$—NH—C(O)N(CH$_3$)$_2$,
  (18) $(CH_2)_{1-2}$—N(CH$_3$)—C(O)N(CH$_3$)$_2$,
  (19) $(CH_2)_{1-2}$—NH—C(S)N(CH$_3$)$_2$,
  (20) $(CH_2)_{1-2}$—N(CH$_3$)—C(S)N(CH$_3$)$_2$,
  (21) $(CH_2)_{1-2}$—NH—SO$_2$CH$_3$,
  (22) $(CH_2)_{1-2}$—N(CH$_3$)SO$_2$CH$_3$,
  (23) $(CH_2)_{1-2}$-phenyl,
  (24) $(CH_2)_{1-2}$—OCH$_2$-phenyl,
  (25) $(CH_2)_{1-2}$-HetC, wherein HetC is a heteroaromatic ring selected from the group consisting of pyridyl, pyrrolyl, pyrazinyl, pyrimidinyl, pyridazinyl, thienyl, furanyl, imidazolyl, pyrazolyl, triazolyl, tetrazolyl, oxazolyl, isooxazolyl, thiazolyl, and isothiazolyl,
  (26) $(CH_2)_{1-2}$-HetD, wherein HetD is a saturated heterocyclic ring selected from the group consisting of piperidinyl, piperazinyl, morpholinyl, thiomorpholinyl, thiazolidinyl, isothiazolidinyl, oxazolidinyl, isoxazolidinyl, pyrrolidinyl, imidazolidinyl, tetrahydrofuranyl, tetrahydrothienyl, tetrahydropyranyl, tetrahydrothiopyranyl, and dioxanyl, wherein the saturated heterocyclic ring is optionally substituted with 1 or 2 oxo groups and is optionally substituted with 1 or 2 methyl groups, or
  (27) $(CH_2)_{1-2}$-HetD, wherein HetD is benzopiperidinyl;
R⁴ is
  (1) H,
  (2) $C_{1-4}$ alkyl,
  (3) $C_{1-5}$ alkyl substituted with:
    (a) —OCH$_3$,
    (b) —CF$_3$,
    (c) —CO$_2$—$C_{1-4}$ alkyl,
    (d) —NH($C_{1-4}$ alkyl),
    (e) —N($C_{1-4}$ alkyl)$_2$,
    (f) —SCH$_3$,
    (g) —SCH$_2$CH$_3$,
    (h) —$C_{3-6}$ cycloalkyl, which is optionally substituted with —$C_{1-4}$ alkyl, —OCH$_3$, —CF$_3$, —OH, phenyl, morpholinyl optionally substituted with CH$_3$, piperidinyl optionally substituted with CH$_3$, or piperazinyl optionally substituted with CH$_3$,
    (i) aryl selected from the group consisting of phenyl and naphthyl, wherein the aryl is optionally substituted with 1 or 2 substituents each of which is independently halo, —CH$_3$, —OCH$_3$, —CF$_3$, or —OH,
    (j) a heteroaryl selected from the group consisting of pyridyl, pyrimidinyl, oxazolyl, isoxazolyl, thiazolyl, isothiazolyl, pyrrolyl, pyrazolyl, imidazolyl, thienyl, furanyl, quinolinyl, isoquinolinyl, cinnolinyl, quinazolinyl, and imidazo[1,2-a]pyridinyl,
    (k) a saturated heterocyclic ring selected from the group consisting of piperidinyl, morpholinyl, thiomorpholinyl, piperazinyl, and dioxanyl, where the saturated heterocyclic ring is optionally substituted with methyl, —C(O)CH$_3$, —C(O)C(O)N(CH$_3$)$_2$, or oxo and optionally substituted with —CH$_2$-cyclopropyl, benzyl or a heteroaryl selected from the group consisting of pyridyl, pyrimidinyl, and pyrazinyl, or
    (l) 1-azabicyclo[4.4.0]decyl,
  (4) $C_{1-3}$ alkyl substituted with —CO$_2$—$C_{1-4}$ alkyl and with —SCH$_3$ or —SCH$_2$CH$_3$,
  (5) $C_{1-3}$ alkyl substituted with a saturated heterocyclic ring and either a $C_{3-6}$ cycloalkyl or a heteroaryl,
    wherein the saturated heterocyclic ring is selected from the group consisting of piperidinyl, morpholinyl, thiomorpholinyl, and piperazinyl, wherein the saturated ring is optionally substituted with 1 or 2 methyl groups, and
    wherein the heteroaryl is selected from the group consisting of pyridyl, pyrimidinyl, oxazolyl, isoxazolyl, thiazolyl, isothiazolyl, pyrrolyl, pyrazolyl, imidazolyl, thienyl, and furanyl,
  (6) $C_{1-3}$ alkyl substituted with two $C_{3-6}$ cycloalkyl groups that are the same or different,
  (7) $(CH_2)_{1-2}CH=CH_2$,
  (8) $C_{3-7}$ cycloalkyl optionally substituted with —$C_{1-4}$ alkyl, —OH, —OCH$_3$, —CF$_3$, phenyl, or a saturated heterocyclic ring selected from the group consisting of piperidinyl, piperazinyl, and morpholinyl, where the saturated heterocyclic ring is optionally substituted with 1 or 2 methyl groups,
  (9) aryl selected from the group consisting of phenyl, naphthyl and indanyl, where the phenyl is optionally substituted with —$C_{1-4}$ alkyl, —OCH$_3$, —CF$_3$, or a saturated heterocyclic ring selected from the group consisting of piperidinyl, piperazinyl, and morpholinyl, where the saturated heterocyclic ring is optionally substituted with 1 or 2 methyl groups,
  (10) adamantyl which is optionally substituted with methyl or OH,
  (11) heteroaryl selected from the group consisting of pyridyl, pyrimidinyl, pyrazinyl, and thiochromanyl in which the S atom is optionally in the form of a monoxide or dioxide, where the heteroaryl is optionally substituted with 1 or 2 substituents each of which is independently a —CH$_3$, —OCH$_3$, or a saturated heterocyclic ring selected from the group consisting of piperidinyl, piperazinyl, and morpholinyl, where the saturated heterocyclic ring is optionally substituted with 1 or 2 methyl groups,
  (12) a saturated heterocyclic ring selected from the group consisting of piperidinyl, morpholinyl, thiomorpholinyl, thiazolidinyl, isothiazolidinyl, oxazolidinyl, isoxazolidinyl, pyrrolidinyl, imidazolidinyl, piperazinyl, tetrahydrofuranyl, tetrahydrothienyl, pyrazolidinyl, hexahydropyrimidinyl, thiazinanyl, thiazepanyl, thiadiazepanyl, dithiazepanyl, azepanyl, diazepanyl, thiadiazinanyl, tetrahydropyranyl, tetrahydrothiopyranyl, and dioxanyl, wherein the saturated heterocyclic ring is optionally substituted (i) with from 1 to 6 methyls, (ii) with 1 or 2 substituents each of which is independently —$CF_3$, —$C(O)CH_3$, —$C(O)C(O)N(CH_3)_2$, or oxo and (iii) with —$CH_2$-cyclopropyl, benzyl, —$C(O)CH_2$-morpholinyl, or —$C(O)CH_2$-piperidinyl, or

(13) 1-azabicyclo[2.2.2]octyl or 1-azabicyclo[4.4.0]decyl; and $R^5$ is H, $CH_3$, or $CH_2$-phenyl.

A sub-class of the first class includes compounds of Formula II, and pharmaceutically acceptable salts thereof, wherein each of the variables is as defined above in the first class, and wherein any ring nitrogen in any saturated heterocyclic ring contained in $R^3$ and $R^4$ is a tertiary amine per se or is a tertiary amine formed by attachment of the ring nitrogen to the rest of the molecule via a carbon atom or by attachment of a substituent group on the ring nitrogen via a carbon atom in the substituent. An example of a saturated heterocyclic ring containing tertiary amine per se is 1-azabicyclo[2.2.2]octyl. As another example, in this sub-class, when $R^4$ is $C_{1-5}$ alkyl substituted with a piperazine which in turn is mono-substituted with acetyl, $R^4$ is:

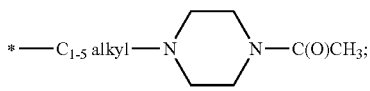

wherein the asterisk * is the point of attachment of R4 to the rest of the molecule.

A second class of the present invention includes compounds of Formula IV, and pharmaceutically acceptable salts thereof:

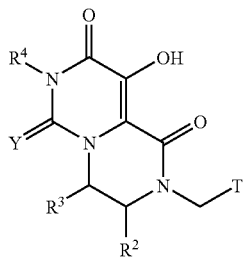

wherein:

Y is O or N—$CH_2$-phenyl;

T is:
(1) phenyl which is optionally substituted with from 1 to 3 substituents each of which is independently fluoro, chloro, methyl, trifluoromethyl, methoxy, CN, —$SO_2CH_3$, —C(=O)NH($CH_3$), or —C(=O)N($CH_3$)$_2$,
(2) naphthyl,
(3) pyridyl,
(4) isoquinolinyl, or
(5) quinolinyl;

$R^2$ is:
(1) H,
(2) $CH_2$—C(O)NH($C_{1-4}$ alkyl), or
(3) $CH_2$—C(O)N($C_{1-4}$ alkyl)$_2$;

$R^3$ is:
(1) H,
(2) $C_{1-5}$ alkyl,
(3) $(CH_2)_{1-2}$—OH,
(4) $(CH_2)_{1-2}$—O—$C_{1-4}$ alkyl,
(5) $(CH_2)_{1-2}$—$NH_2$,
(6) $(CH_2)_{1-2}$—NH($C_{1-4}$ alkyl),
(7) $(CH_2)_{1-2}$—N($C_{1-4}$ alkyl)$_2$,
(8) $(CH_2)_{1-2}$—N(O—$C_{1-4}$ alkyl)-$C_{1-4}$ alkyl,
(9) $(CH_2)_{1-2}$—NH—$CH_2$-phenyl,
(10) $(CH_2)_{1-2}$—N($CH_3$)—$CH_2$-phenyl,
(11) $(CH_2)_{1-2}$—NH—C(O)—$C_{1-4}$ alkyl,
(12) $(CH_2)_{1-2}$—N($CH_3$)—C(O)—$C_{1-4}$ alkyl,
(13) $(CH_2)_{1-2}$—NH—C(O)-phenyl,
(14) $(CH_2)_{1-2}$—N($CH_3$)—C(O)-phenyl,
(15) $(CH_2)_{1-2}$—NH—C(O)N($C_{1-4}$ alkyl)$_2$,
(16) $(CH_2)_{1-2}$—N($CH_3$)—C(O)NH($C_{1-4}$ alkyl),
(17) $(CH_2)_{1-2}$—N($CH_3$)—C(O)N($C_{1-4}$ alkyl)$_2$,
(18) $(CH_2)_{1-2}$—NH—C(S)N($C_{1-4}$ alkyl)$_2$,
(19) $(CH_2)_{1-2}$—N($CH_3$)—C(S)NH($C_{1-4}$ alkyl),
(20) $(CH_2)_{1-2}$—N($CH_3$)—C(S)N($C_{1-4}$ alkyl)$_2$,
(21) $(CH_2)_{1-2}$—N—H—$SO_2$—$C_{1-4}$ alkyl,
(22) $(CH_2)_{1-2}$—N($CH_3$)—$SO_2$—$C_{1-4}$ alkyl,
(23) $(CH_2)_{1-2}$-phenyl,
(24) $(CH_2)_{1-2}$—$OCH_2$-phenyl,
(25) $(CH_2)_{1-2}$-HetC, where HetC is a heteroaromatic ring selected from the group consisting of pyridyl, pyrrolyl, pyrazinyl, pyrimidinyl, pyridazinyl, triazinyl, thienyl, furanyl, imidazolyl, pyrazolyl, triazolyl, tetrazolyl, oxazolyl, isooxazolyl, oxadiazolyl, oxatriazolyl, thiazolyl, isothiazolyl, and thiadiazolyl, wherein the heteroaromatic ring is optionally substituted with 1 or 2 substituents each of which is independently halo or a $C_{1-4}$ alkyl, or
(26) $(CH_2)_{1-2}$-HetD, where HetD is a saturated heterocyclic ring selected from the group consisting of piperidinyl, morpholinyl, thiomorpholinyl, thiazolidinyl, isothiazolidinyl, oxazolidinyl, isoxazolidinyl, pyrrolidinyl, imidazolidinyl, piperazinyl, tetrahydrofuranyl, tetrahydrothienyl, pyrazolidinyl, hexahydropyrimidinyl, thiazinanyl, thiazepanyl, thiadiazepanyl, dithiazepanyl, azepanyl, diazepanyl, thiadiazinanyl, tetrahydropyranyl, tetrahydrothiopyranyl, and dioxanyl; wherein the saturated heterocyclic ring is optionally substituted with from 1 to 4 substituents each of which is independently oxo or a $C_{1-4}$ alkyl;

$R^4$ is
(1) H,
(2) $C_{1-4}$ alkyl,
(3) $(CH_2)_{1-3}L^1$ or CH($CH_3$)-$L^1$, wherein $L^1$ is:
(a) —O—$C_{1-4}$ alkyl,
(b) —$CF_3$,
(c) —$CO_2$—$C_{1-4}$ alkyl,
(d) —NH($C_{1-4}$ alkyl),
(e) —N($C_{1-4}$ alkyl)$_2$,
(f) —S—$C_{1-4}$ alkyl,
(g) —$C_{3-6}$ cycloalkyl, which is optionally substituted with —$C_{1-4}$ alkyl, —$OCH_3$, —$CF_3$, —OH, phenyl, morpholinyl optionally substituted with $CH_3$, piperidinyl optionally substituted with $CH_3$, or piperazinyl optionally substituted with $CH_3$,
(i) aryl selected from the group consisting of phenyl and naphthyl, where the phenyl is optionally substituted with 1 or 2 substituents each of which is independently halo, —$CH_3$, —$OCH_3$, —$CF_3$, or —OH, (j) a heteroaryl selected from the group consisting of pyridyl, pyrimidinyl, oxazolyl, isoxazolyl, thiazolyl, isothiazolyl, pyrrolyl, pyrazolyl, imidazolyl, thienyl, furanyl, quinolinyl, isoquinolinyl, cinnolinyl, quinazolinyl, and imidazo[1,2-a]pyridinyl, (k) a saturated heterocyclic ring selected from the group consisting of piperidinyl, morpholinyl, thiomorpholinyl, piperazinyl, and dioxanyl, where the saturated heterocyclic ring is optionally substituted with methyl, —C(O)CH$_3$, —C(O)C(O)N(CH$_3$)$_2$, or oxo and optionally substituted with —CH$_2$-cyclopropyl, benzyl or a heteroaryl selected from the group consisting of pyridyl, pyrimidinyl, and pyrazinyl, or (l) 1-azabicyclo[4.4.0]decyl, (4) C$_{1-3}$ alkyl, either of which is substituted with:
  (a) —CO$_2$—C$_{1-4}$ alkyl and with —SCH$_3$ or —SCH$_2$CH$_3$,
  (b) a saturated heterocyclic ring and with either a C$_{3-6}$ cycloalkyl or a heteroaryl, wherein
    (i) the saturated heterocyclic ring is selected from the group consisting of piperidinyl, morpholinyl, thiomorpholinyl, and piperazinyl, wherein the saturated ring is optionally substituted with 1 or 2 methyl groups, and
    (ii) the heteroaryl is selected from the group consisting of pyridyl, pyrimidinyl, oxazolyl, isoxazolyl, thiazolyl, isothiazolyl, pyrrolyl, pyrazolyl, imidazolyl, thienyl, and furanyl,
  (c) two C$_{3-6}$ cycloalkyl groups that are the same or different, (5) (CH$_2$)$_{0-1}$C(CH$_3$)$_2$(CH$_2$)$_{0-1}$-L$^2$ wherein L$^2$ is —CO$_2$—C$_{1-4}$ alkyl or a saturated heterocyclic ring selected from the group consisting of piperidinyl, morpholinyl, thiomorpholinyl, and piperazinyl, wherein the saturated ring is optionally substituted with 1 or 2 methyl groups, (6) CH(CH$_3$)CH$_2$—O—C$_{1-4}$ alkyl, (7) (CH$_2$)$_{1-2}$CH=CH$_2$, (8) C$_{3-7}$ cycloalkyl optionally substituted with —C$_{1-4}$ alkyl, —OH, —OCH$_3$, —CF$_3$, phenyl, or a saturated heterocyclic ring selected from the group consisting of piperidinyl, piperazinyl, and morpholinyl, where the saturated heterocyclic ring is optionally substituted with 1 or 2 methyl groups, (9) aryl selected from the group consisting of phenyl, naphthyl and indanyl, where the phenyl is optionally substituted with —C$_{1-4}$ alkyl, —OCH$_3$, —CF$_3$, or a saturated heterocyclic ring selected from the group consisting of piperidinyl, piperazinyl, and morpholinyl, where the saturated heterocyclic ring is optionally substituted with 1 or 2 methyl groups,

(10) adamantyl which is optionally substituted with methyl or OH,

(11) heteroaryl selected from the group consisting of pyridyl, pyrimidinyl, pyrazinyl, and thiochromanyl in which the S atom is optionally in the form of a monoxide or dioxide, where the heteroaryl is optionally substituted with 1 or 2 substituents each of which is independently a —CH$_3$, —OCH$_3$, or a saturated heterocyclic ring selected from the group consisting of piperidinyl, piperazinyl, and morpholinyl, where the saturated heterocyclic ring is optionally substituted with 1 or 2 methyl groups,

(12) a saturated heterocyclic ring selected from the group consisting of piperidinyl, morpholinyl, thiomorpholinyl, thiazolidinyl, isothiazolidinyl, oxazolidinyl, isoxazolidinyl, pyrrolidinyl, imidazolidinyl, piperazinyl, tetrahydrofuranyl, tetrahydrothienyl, pyrazolidinyl, hexahydropyrimidinyl, thiazinanyl, thiazepanyl, thiadiazepanyl, dithiazepanyl, azepanyl, diazepanyl, thiadiazinanyl, tetrahydropyranyl, tetrahydrothiopyranyl, and dioxanyl, wherein the saturated heterocyclic ring is optionally substituted (i) with from 1 to 6 methyls, (ii) with 1 or 2 substituents each of which is independently —CF$_3$, —C(O)CH$_3$, —C(O)C(O)N(CH$_3$)$_2$, or oxo and (iii) with —CH$_2$-cyclopropyl, benzyl, —C(O)CH$_2$-morpholinyl, or —C(O)CH$_2$-piperidinyl, or

(13) 1-azabicyclo[2.2.2]octyl or 1-azabicyclo[4.4.0]decyl.

A first sub-class of the second class includes compounds of Formula IV, and pharmaceutically acceptable salts thereof, wherein Y is O; T is 4-fluorophenyl; R$^2$ is H; R$^3$ is H; and all other variables are as defined in the first class.

A second sub-class of the second class includes compounds of Formula IV, and pharmaceutically acceptable salts thereof, wherein each of the variables is as defined in the second class, and wherein any ring nitrogen in any saturated heterocyclic ring contained in R$^3$ and R$^4$ is a tertiary amine per se or is a tertiary amine formed by attachment of the ring nitrogen to the rest of the molecule via a carbon atom or by attachment of a substituent group on the ring nitrogen via a carbon atom in the substituent.

A third sub-class of the second class includes compounds of Formula IV, and pharmaceutically acceptable salts thereof, wherein each of the variables is as defined in the first sub-class, and wherein any ring nitrogen in any saturated heterocyclic ring contained in R$^3$ and R$^4$ is a tertiary amine per se or is a tertiary amine formed by attachment of the ring nitrogen to the rest of the molecule via a carbon atom or by attachment of a substituent group on the ring nitrogen via a carbon atom in the substituent.

Another embodiment of the present invention is a compound, or a pharmaceutically acceptable salt thereof, selected from the group consisting of the compounds set forth in Examples 1 to 87 below.

Still another embodiment of the present invention is a compound, or a pharmaceutically acceptable salt thereof, selected from the group consisting of the compounds set forth in Examples 1, 3, 4 to 6, 10, 13, 15, 17, 19, 20, 23, 36, 38 to 47, 49, 51, 57 to 61, 76 to 78, 80, 81, 84, 86 and 87 below.

Other embodiments of the present invention include the following:

(a) A pharmaceutical composition comprising an effective amount of a compound of Formula I and a pharmaceutically acceptable carrier.

(b) A pharmaceutical composition which comprises the product prepared by combining (e.g., mixing) an effective amount of a compound of Formula I and a pharmaceutically acceptable carrier.

(c) The pharmaceutical composition of (a) or (b), further comprising an effective amount of an HIV infection/AIDS treatment agent selected from the group consisting of HIV/AIDS antiviral agents, immunomodulators, and anti-infective agents.

(d) The pharmaceutical composition of (c), wherein the HIV infection/AIDS treatment agent is an antiviral selected from the group consisting of HIV protease inhibitors, non-nucleoside HIV reverse transcriptase inhibitors, and nucleoside HIV reverse transcriptase inhibitors.

(e) A pharmaceutical combination which is (i) a compound of Formula I and (ii) an HIV infection/AIDS treatment agent selected from the group consisting of HIV/AIDS antiviral agents, immunomodulators, and anti-infective agents; wherein the compound of Formula I and the HIV infection/AIDS treatment agent are each employed in an amount that renders the combination effective for inhibiting HIV integrase, for treating or preventing infection by HIV, or for preventing, treating or delaying the onset of AIDS.

(f) The combination of (e), wherein the HIV infection/AIDS treatment agent is an antiviral selected from the group consisting of HIV protease inhibitors, non-nucleoside HIV reverse transcriptase inhibitors and nucleoside HIV reverse transcriptase inhibitors.

(g) A method of inhibiting HIV integrase in a subject in need thereof which comprises administering to the subject an effective amount of a compound of Formula I.

(h) A method of preventing or treating infection by HIV in a subject in need thereof which comprises administering to the subject an effective amount of a compound of Formula I.

(i) The method of (h), wherein the compound of Formula (I) is administered in combination with an effective amount of at least one antiviral selected from the group consisting of HIV protease inhibitors, non-nucleoside HIV reverse transcriptase inhibitors, and nucleoside HIV reverse transcriptase inhibitors.

(j) A method of preventing, treating or delaying the onset of AIDS in a subject in need thereof which comprises administering to the subject an effective amount of a compound of Formula I.

(k) The method of (j), wherein the compound is administered in combination with an effective amount of at least one antiviral selected from the group consisting of HIV protease inhibitors, non-nucleoside HIV reverse transcriptase inhibitors, and nucleoside HIV reverse transcriptase inhibitors (l) A method of inhibiting HIV integrase in a subject in need thereof which comprises administering to the subject the pharmaceutical composition of (a), (b), (c) or (d) or the combination of (e) or (f).

(m) A method of preventing or treating infection by HIV in a subject in need thereof which comprises administering to the subject the pharmaceutical composition of (a), (b), (c) or (d) or the combination of (e) or (f).

(n) A method of preventing, treating or delaying the onset of AIDS in a subject in need thereof which comprises administering to the subject the pharmaceutical composition of (a), (b), (c) or (d) or the combination of (e) or (f).

The present invention also includes a compound of the present invention (i) for use in, (ii) for use as a medicament for, or (iii) for use in the preparation of a medicament for: (a) inhibiting HIV integrase, (b) preventing or treating infection by HIV, or (c) preventing, treating or delaying the onset of AIDS. In these uses, the compounds of the present invention can optionally be employed in combination with one or more HIV/AIDS treatment agents selected from HIV/AIDS antiviral agents, anti-infective agents, and immunomodulators.

Additional embodiments of the invention include the pharmaceutical compositions, combinations and methods set forth in (a)-(n) above and the uses set forth in the preceding paragraph, wherein the compound of the present invention employed therein is a compound of one of the embodiments, aspects, classes, sub-classes, or features of the compounds described above. In all of these embodiments, the compound may optionally be used in the form of a pharmaceutically acceptable salt.

As used herein, the term "alkyl" refers to any linear or branched chain alkyl group having a number of carbon atoms in the specified range. Thus, for example, "$C_{1-6}$ alkyl" (or "$C_1$-$C_6$ alkyl") refers to all of the hexyl alkyl and pentyl alkyl isomers as well as n-, iso-, sec- and t-butyl, n- and isopropyl, ethyl and methyl. As another example, "$C_{1-4}$ alkyl" refers to n-, iso-, sec- and t-butyl, n- and isopropyl, ethyl and methyl.

The term "alkylene" refers to any linear or branched chain alkylene group (or alternatively "alkanediyl") having a number of carbon atoms in the specified range. Thus, for example, "—$C_{1-6}$ alkylene-" refers to any of the $C_1$ to $C_6$ linear or branched alkylenes. A class of alkylenes of particular interest with respect to the invention is —$(CH_2)_{1-6}$—, and sub-classes of particular interest include —$(CH_2)_{1-4}$—, —$(CH_2)_{1-3}$—, —$(CH_2)_{1-2}$—, and —$CH_2$—. Also of interest is the alkylene —$CH(CH_3)$—.

The term "alkenyl" means any linear or branched chain alkenyl group having a number of carbon atoms in the specified range. Thus, for example, "$C_{2-6}$ alkenyl" (or "$C_2$-$C_6$ alkenyl") refers to all of the hexenyl and pentenyl isomers as well as 1-butenyl, 2-butenyl, 3-butenyl, isobutenyl, 1-propenyl, 2-propenyl, and ethenyl (or vinyl).

The term "cycloalkyl" refers to any cyclic ring of an alkane having a number of carbon atoms in the specified range. Thus, for example, "$C_{3-8}$ cycloalkyl" (or "$C_3$-$C_8$ cycloalkyl") refers to cyclopropyl, cyclobutyl, cyclopentyl, cyclohexyl, cycloheptyl, and cyclooctyl.

The term "halogen" (or "halo") refers to fluorine, chlorine, bromine and iodine (alternatively referred to as fluoro, chloro, bromo, and iodo).

The term "haloalkyl" refers to an alkyl group as defined above in which one or more of the hydrogen atoms has been replaced with a halogen (i.e., F, Cl, Br and/or I). Thus, for example, "$C_{1-6}$ haloalkyl" (or "$C_1$-$C_6$ haloalkyl") refers to a $C_1$ to $C_6$ linear or branched alkyl group as defined above with one or more halogen substituents. The term "fluoroalkyl" has an analogous meaning except that the halogen substituents are restricted to fluoro. Suitable fluoroalkyls include the series $(CH_2)_{0-4}CF_3$ (i.e., trifluoromethyl, 2,2,2-trifluoroethyl, 3,3,3-trifluoro-n-propyl, etc.).

The term "$C_{4-7}$ azacycloalkyl" (or "$C_4$-$C_7$ azacycloalkyl") means a saturated cyclic ring consisting of one nitrogen and from four to seven carbon atoms (i.e., pyrrolidinyl, piperidinyl, azepanyl, or octahydroazocinyl).

The term "$C_{3-6}$ diazacycloalkyl" (or "$C_3$-$C_6$ diazacycloalkyl") means a saturated cyclic ring consisting of two nitrogens and from three to six carbon atoms (e.g., imidazolidinyl, pyrazolidinyl, or piperazinyl).

Unless expressly stated to the contrary, all ranges cited herein are inclusive. For example, a heterocyclic ring described as containing from "1 to 4 heteroatoms" means the ring can contain 1, 2, 3 or 4 heteroatoms. It is also to be understood that any range cited herein includes within its scope all of the sub-ranges within that range. Thus, for example, a heterocyclic ring described as containing from "1 to 4 heteroatoms" is intended to include as aspects thereof, heterocyclic rings containing 2 to 4 heteroatoms, 3 or 4 heteroatoms, 1 to 3 heteroatoms, 2 or 3 heteroatoms, 1 or 2 heteroatoms, 1 heteroatom, 2 heteroatoms, and so forth.

When any variable (e.g., $R^A$, $R^B$, and HetA) occurs more than one time in any constituent or in Formula I, Formula II, or in any other formula depicting and describing compounds of the invention, its definition on each occurrence is independent of its definition at every other occurrence. Also, combinations of substituents and/or variables are permissible only if such combinations result in stable compounds.

The term "substituted" (e.g., as in "is optionally substituted with from 1 to 5 substituents . . . ") includes mono- and poly-substitution by a named substituent to the extent such single and multiple substitution (including multiple substitution at the same site) is chemically allowed. Unless expressly stated to the contrary, substitution by a named substituent is permitted on any atom in a ring (e.g., cycloalkyl, aryl, a heteroaromatic ring, or a saturated heterocyclic ring) provided such ring substitution is chemically allowed and results in a stable compound. As an example, in the case where $R^4$ is a mono- or poly-substituted $C_{3-8}$ cycloalkyl, a substituent can be attached to the ring carbon atom of the cycloalkyl that is itself attached to the rest of the molecule; e.g., $R^4$=cyclohexyl mono-substituted with alkyl includes the following moiety, wherein the asterisk * denotes attachment of the $R^4$ group to the rest of the molecule:

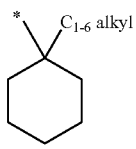

In instances where a hydroxy (—OH) substituent(s) is(are) permitted on a heteroaromatic ring and keto-enol tautomerism is possible, it is understood that the substituent might in fact be present, in whole or in part, in the keto form, as exemplified here for a hydroxypyridinyl substituent:

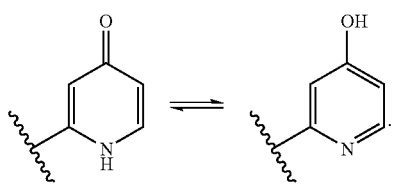

Compounds of the present invention having a hydroxy substituent on a carbon atom of a heteroaromatic ring are understood to include compounds in which only the hydroxy is present, compounds in which only the tautomeric keto form (i.e., an oxo substitutent) is present, and compounds in which the keto and enol forms are both present.

Any of the various carbocyclic and heterocyclic rings and ring systems defined herein may be attached to the rest of the compound at any ring atom (i.e., any carbon atom or any heteroatom) provided that a stable compound results. Suitable bicyclic carbocycles include, for example, bicyclo[2.2.1]heptyl, bicyclo[2.2.2]octyl, decahydronaphthyl, and bicyclo[2.2.1]hept-5-enyl, and octahydroindenyl. Suitable tricyclic carbocycles include, for example, adamantyl, dodecahydrofluorenyl, and tetradecahydroanthracenyl. Suitable heteroaromatic rings include, for example, pyridyl, pyrrolyl, pyrazinyl, pyrimidinyl, pyridazinyl, triazinyl, thienyl, furanyl, imidazolyl, pyrazolyl, triazolyl, tetrazolyl, oxazolyl, isooxazolyl, oxadiazolyl, oxatriazolyl, thiazolyl, isothiazolyl, and thiadiazolyl. Suitable heteroaryls which are bicyclic, fused ring systems include, for example, benzopiperidinyl, benzisoxazolyl, benzoxazolyl, chromenyl, quinolinyl, isoquinolinyl, cinnolinyl, quinazolinyl, and imidazo[1,2-a]pyridinyl. Suitable heteromonocycles include, for example, piperidinyl, morpholinyl, thiomorpholinyl, thiazolidinyl, isothiazolidinyl, oxazolidinyl, isoxazolidinyl, pyrrolidinyl, imidazolidinyl, piperazinyl, tetrahydrofuranyl, tetrahydrothienyl, pyrazolidinyl, hexahydropyrimidinyl, thiazinanyl, thiazepanyl, thiadiazepanyl, dithiazepanyl, azepanyl, diazepanyl, thiadiazinanyl, tetrahydropyranyl, tetrahydrothiopyranyl, dioxanyl, and the mono-unsaturated counterparts of the foregoing saturated rings. Suitable bicyclic heterocycles include, for example, 1-azabicyclo[2.2.2]octyl, 1-azabicyclo[2.2.1]heptyl, 1-azabicyclo[4.4.0]decyl, decahydroquinolinyl, and decahydroisoquinolinyl. Suitable tricyclic heterocycles include, for example, the saturated counterparts to carbazole, xanthene, and acridine.

A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject).

As a result of the selection of substituents and substituent patterns, certain of the compounds of the present invention can have asymmetric centers and can occur as mixtures of stereoisomers, or as individual diastereomers, or enantiomers. All isomeric forms of these compounds, whether isolated or in mixtures, are within the scope of the present invention.

As would be recognized by one of ordinary skill in the art, compounds of the present invention can exist as tautomers including, for example, the following:

For $R^4$ = H:

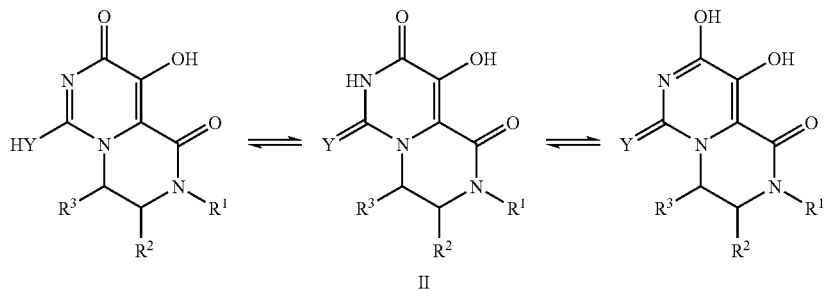

II

[YH = OH, SH, or $NHR^5$]

For R⁴ = other than H:

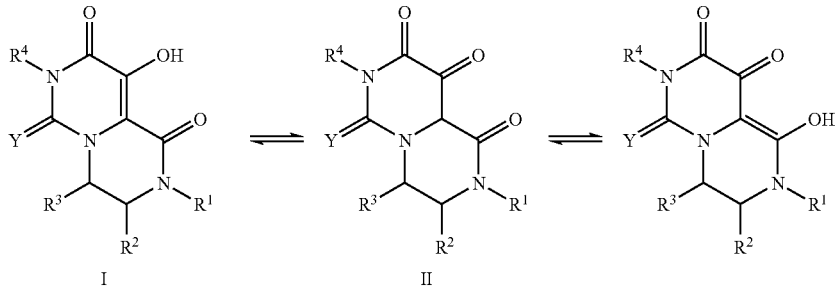

I
[Y is O, S, or NR⁵]

II

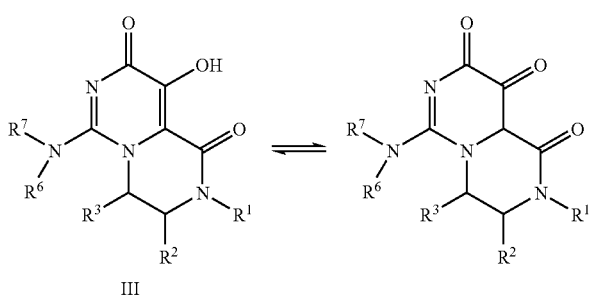

III

For the purposes of the present invention, a reference herein to a compound of Formula I, II, In, or IV is a reference to compound I, II, I or IV per se, or to any one of its tautomers per se, or to mixtures thereof.

The compounds of the present inventions are useful in the inhibition of HIV integrase, the prevention or treatment of infection by human immunodeficiency virus (HIV) and the prevention, treatment or the delay in the onset of consequent pathological conditions such as AIDS. Preventing AIDS, treating AIDS, delaying the onset of AIDS, or preventing or treating infection by HIV is defined as including, but not limited to, treatment of a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by such means as blood transfusion, exchange of body fluids, bites, accidental needle stick, or exposure to patient blood during surgery.

The compounds of this invention are useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HIV integrase, e.g., by competitive inhibition. Thus the compounds of this invention are commercial products to be sold for these purposes.

The compounds of the present invention may be administered in the form of pharmaceutically acceptable salts. The term "pharmaceutically acceptable salt" refers to a salt which possesses the effectiveness of the parent compound and which is not biologically or otherwise undesirable (e.g., is neither toxic nor otherwise deleterious to the recipient thereof). Suitable salts include acid addition salts which may, for example, be formed by mixing a solution of the compound of the present invention with a solution of a pharmaceutically acceptable acid such as hydrochloric acid, sulfuric acid, acetic acid, trifluoroacetic acid, or benzoic acid. Many of the compounds of the invention carry an acidic moiety, in which case suitable pharmaceutically acceptable salts thereof can include alkali metal salts (e.g., sodium or potassium salts), alkaline earth metal salts (e.g., calcium or magnesium salts), and salts formed with suitable organic ligands such as quaternary ammonium salts. Also, in the case of an acid (—COOH) or alcohol group being present, pharmaceutically acceptable esters can be employed to modify the solubility or hydrolysis characteristics of the compound.

The term "administration" and variants thereof (e.g., "administering" a compound) in reference to a compound of the invention mean providing the compound or a prodrug of the compound to the individual in need of treatment. When a compound of the invention or a prodrug thereof is provided in combination with one or more other active agents (e.g., antiviral agents useful for treating HIV infection or AIDS), "administration" and its variants are each understood to include concurrent and sequential provision of the compound or prodrug and other agents.

As used herein, the term "composition" is intended to encompass a product comprising the specified ingredients in the specified amounts, as well as any product which results, directly or indirectly, from combining the specified ingredients in the specified amounts.

By "pharmaceutically acceptable" is meant that the ingredients of the pharmaceutical composition must be compatible with each other and not deleterious to the recipient thereof.

The term "subject" (alternatively referred to herein as "patient") as used herein refers to an animal, preferably a mammal, most preferably a human, who has been the object of treatment, observation or experiment.

The term "effective amount" as used herein means that amount of active compound or pharmaceutical agent that elicits the biological or medicinal response in a tissue, system, animal or human that is being sought by a researcher, veterinarian, medical doctor or other clinician. In one embodiment, the effective amount is a "therapeutically effective amount" for the alleviation of the symptoms of the disease or condition being treated. In another embodiment, the effective amount is a "prophylactically effective amount" for prophylaxis of the symptoms of the disease or condition being prevented. The term also includes herein the amount of active compound sufficient to inhibit HIV integrase and thereby elicit the response being sought (i.e., an "inhibition effective amount"). When the active compound (i.e., active ingredient) is administered as the salt, references to the amount of active ingredient are to the free acid or free base form of the compound.

For the purpose of inhibiting HIV integrase, preventing or treating HIV infection or preventing, treating or delaying the onset of AIDS, the compounds of the present invention, optionally in the form of a salt, can be administered by any means that produces contact of the active agent with the agent's site of action. They can be administered by any conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice. The compounds of the invention can, for example, be administered orally, parenterally (including subcutaneous injections, intravenous, intramuscular, intrasternal injection or infusion techniques), by inhalation spray, or rectally, in the form of a unit dosage of a pharmaceutical composition containing an effective amount of the compound and conventional non-toxic pharmaceutically-acceptable carriers, adjuvants and vehicles. Liquid preparations suitable for oral administration (e.g., suspensions, syrups, elixirs and the like) can be prepared according to techniques known in the art and can employ any of the usual media such as water, glycols, oils, alcohols and the like. Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Parenteral compositions can be prepared according to techniques known in the art and typically employ sterile water as a carrier and optionally other ingredients, such as a solubility aid. Injectable solutions can be prepared according to methods known in the art wherein the carrier comprises a saline solution, a glucose solution or a solution containing a mixture of saline and glucose. Further description of methods suitable for use in preparing pharmaceutical compositions of the present invention and of ingredients suitable for use in said compositions is provided in *Remington's Pharmaceutical Sciences*, $18^{th}$ edition, edited by A. R. Gennaro, Mack Publishing Co., 1990.

The compounds of this invention can be administered orally in a dosage range of 0.001 to 1000 mg/kg of mammal (e.g., human) body weight per day in a single dose or in divided doses. One preferred dosage range is 0.01 to 500 mg/kg body weight per day orally in a single dose or in divided doses. Another preferred dosage range is 0.1 to 100 mg/kg body weight per day orally in single or divided doses. For oral administration, the compositions can be provided in the form of tablets or capsules containing 1.0 to 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

As noted above, the present invention is also directed to use of the HIV integrase inhibitor compounds of the present invention with one or more agents useful in the treatment of HIV infection or AIDS. For example, the compounds of this invention may be effectively administered, whether at periods of pre-exposure and/or post-exposure, in combination with effective amounts of one or more HIV/AIDS antivirals, immunomodulators, antiinfectives, or vaccines useful for treating HIV infection or AIDS, such as those disclosed in Table 1 of WO 01/38332 or in the Table in WO 02/30930. Suitable HIV/AIDS antivirals for use in combination with the compounds of the present invention include, for example, HIV protease inhibitors (e.g., indinavir, atazanavir, lopinavir optionally with ritonavir, saquinavir, or nelfinavir), nucleoside TV reverse transcriptase inhibitors (e.g., abacavir, lamivudine (3TC), zidovudine (AZT), or tenofovir), and non-nucleoside HIV reverse transcriptase inhibitors (e.g., efavirenz or nevirapine). It will be understood that the scope of combinations of the compounds of this invention with HIV/AIDS antivirals, immunomodulators, anti-infectives or vaccines is not limited to the foregoing substances or to the list in the above-referenced Tables in WO 01/38332 and WO 02/30930, but includes in principle any combination with any pharmaceutical composition useful for the treatment of AIDS. The HIV/AIDS antivirals and other agents will typically be employed in these combinations in their conventional dosage ranges and regimens as reported in the art, including, for example, the dosages described in the *Physicians' Desk Reference*, $57^{th}$ edition, Thomson PDR, 2003. The dosage ranges for a compound of the invention in these combinations are the same as those set forth above.

Abbreviations used in the instant specification, particularly the Schemes and Examples, include the following:
AIDS=acquired immunodeficiency syndrome
Alloc=alloxycarbonyl
ARC=AIDS related complex
BOC or Boc=t-butyloxycarbonyl
CBZ=carbobenzoxy (alternatively, benzyloxycarbonyl)
DIEA or DIPEA=diisopropylethylamine (or Hunig's base)
DMAP=dimethylaminopyridine
DMF=dimethylformamide
DMSO=dimethylsulfoxide
EDC or EDAC=1-ethyl-3-(3-dimethylaminopropyl) carbodiimide
ES-MS=electron spray mass spectroscopy
EtOAc ethyl acetate
EtOH=ethanol
HIV=human immunodeficiency virus
gHMBC=gradient-selected heteronuclear multiple bond correlation
HMQC=heteronuclear multiple quantum coherence (NMR)
HOBT or HOBt=1-hydroxy benzotriazole hydrate
HPLC=high performance liquid chromatography
HRMS=high resolution mass spectroscopy
LAH=lithium aluminum hydride
LC=liquid chromatography
Me=methyl
MeOH=methanol
NMR=nuclear magnetic resonance ROESY=rotating frame nuclear Overhauser effect spectroscopy TFA=trifluoroacetic acid THF=tetrahydrofuran The compounds of the present invention can be readily prepared according to the following reaction schemes and examples, or modifications thereof, using readily available starting materials, reagents and conventional synthesis procedures. In these reactions, it is also possible to make use of variants which are themselves known to those of ordinary skill in this art, but are not mentioned in greater detail. Furthermore, other methods for preparing compounds of the invention will be readily apparent to the person of ordinary skill in the art in light of the following reaction schemes and examples. Unless otherwise indicated, all variables are as defined above.

Compounds of Formula I of the present invention in which Y=O or S can be prepared as shown in Scheme 1, wherein an appropriately substituted piperazin-2-one 1 can be reacted at the position 4 nitrogen with an isocyanate or thioisocyanate to give urea or thiourea 2. Treatment of 2 with a strong base such as lithium bis-trimethylsilylamide and an oxalate ester or equivalent reagent will form the second ring to provide the 3,4-dihydro-2H-pyrazino[1,2-c]pyrimidine-1,6,8(7H)-trione or 6-thioxo-3,4,6,7-tetrahydro-2H-pyrazino[1,2-c]pyrimidine-1,8-dione final product 3.

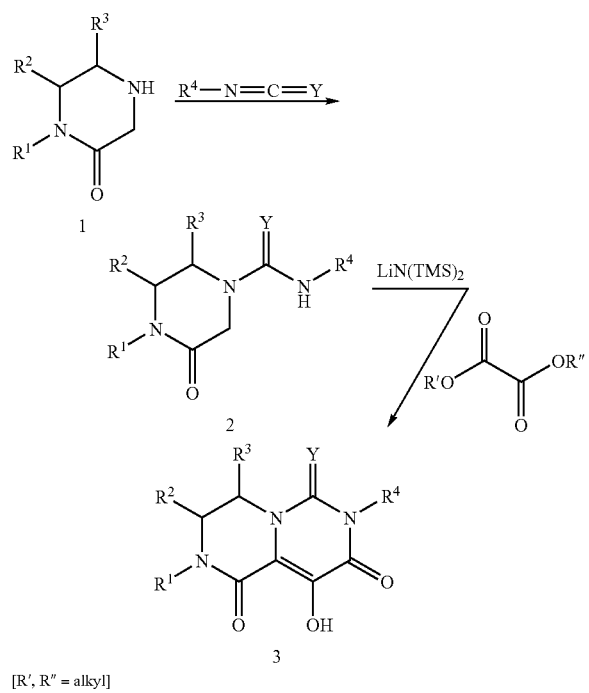

SCHEME 1

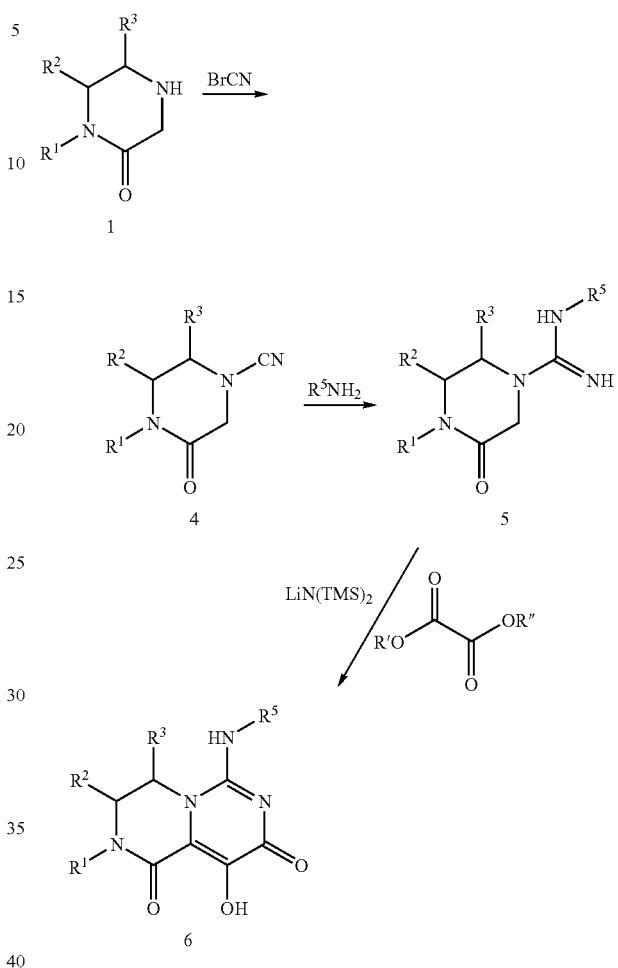

SCHEME 2

Scheme 2 depicts a method for preparing compounds of Formula I of the present invention in which Y is NHR⁵, wherein the position 4 nitrogen in piperazinone 1 can be cyanated to give cyanamide 4. Addition of an amine to the cyano group in 4 will give the guanidine product 5. Treatment of guanidine 5 with a strong base such as lithium bis-trimethylsilylamide and an oxalate ester or equivalent reagent will form the second ring to give the 6-amino-9-hydroxy-3,4-dihydro-2H-pyrazino[1,2-c]pyrimidine-1,8-dione final product 6.

The piperazin-2-ones 1 utilized in Schemes 1 and 2 can be prepared by a number of different methods described in the literature (e.g., N. Yahiro, et al., *Bull. Chem. Soc. Japan*, 1986, vol. 59, p. 321; B. Lee, et al., *Tetrahedron Letters*, 1999, vol. 40, p. 643; C. Dinsmore et al., *Tetrahedron Letters*, 2000, vol. 41, p. 6309) and by other methods given in the examples set forth below. Two general methods for piperazinone synthesis are given in Schemes 3 and 4. In Scheme 3, an N-protected amino acid (PG=a carbamate protecting group such as Boc, Cbz, and Alloc) 7 is activated with a carbodiimide or other peptide coupling reagent and condensed with N-methoxy-N-methylamine to give amide 8. Amide 8 can then be reacted with an organometallic reagent or metal hydride reagent to give ketone or aldehyde 9. The ketone or aldehyde group in 9 can then be reacted with an amine in the presence of a reducing agent such as sodium triacetoxyborohydride to give diamine 10. The newly introduced amino group in 10 can then be acylated with bromoacetyl bromide or equivalent alpha-haloacetic acid reagent to provide bromoacetamide 11. The amine protecting group in 11 can then be removed to permit intramolecular displacement of the bromide by the newly liberated amino group to give piperazinone 1.

SCHEME 3

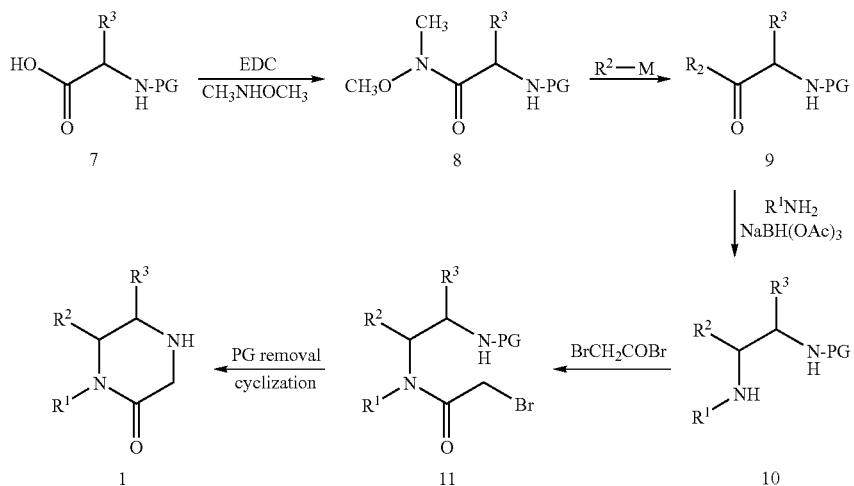

Scheme 4 depicts an alternative method for preparing piperazin-2-one 1, wherein an N-protected amino acid (PG=protecting group) 12 can be activated with a carbodiimide or other peptide coupling reagent and condensed with N-methoxy-N-methylamine to give amide 13. The nitrogen bearing the protecting group in 13 can then be deprotonated with a strong base such as sodium hydride and alkylated with an alkyl halide to give 14. The amide group in 14 can then be reacted with an organometallic reagent or metal hydride reagent to give ketone or aldehyde 15. The ketone or aldehyde group in 15 can then be reacted with glycine ester in the presence of a reducing agent such as sodium triacetoxyborohydride to give 16. Removal of the amine protecting group in 16 followed by intramolecular closure of the newly liberated amino group onto the glycyl ester group gives piperazinone 1.

SCHEME 4

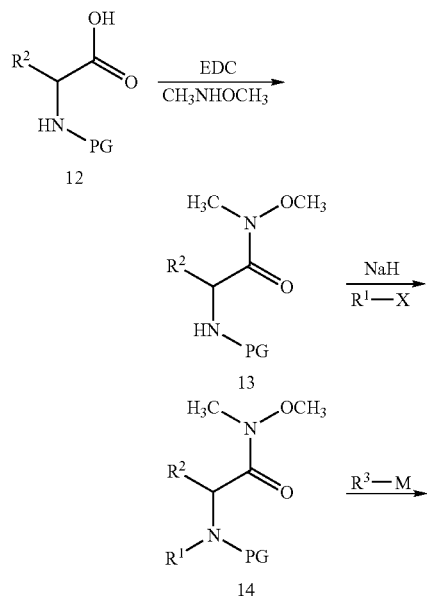

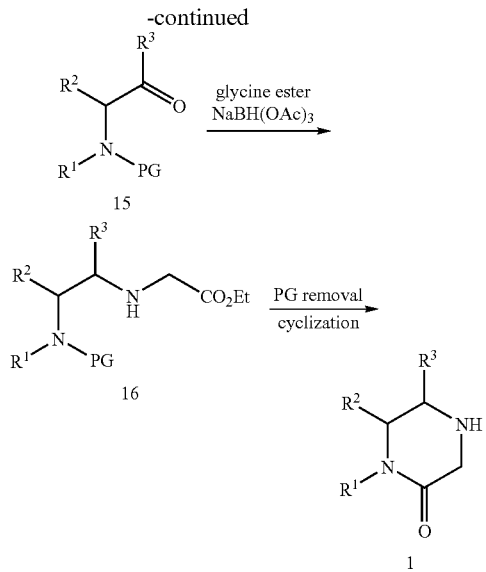

Amine protective groups suitable for use in the foregoing schemes and methods for their formation and removal are described in T. H. Greene and P. G. M. Wuts, *Protective Groups in Organic Synthesis*, 2nd edition, John Wiley & Sons, New York (1991), pp. 315-385.

Additional $R^1$ group analogs of Formula I may be prepared by synthesizing 3,4-dihydro-2H-pyrazino[1,2-c]pyrimidine-1,6,8(7H)-trione or 6-thioxo-3,4,6,7-tetrahydro-2H-pyrazino[1,2-c]pyrimidine-1,8-dione intermediates which contain a removable protecting group on nitrogen position 2, for example the N-allyl derivative 17 shown in Scheme 5. The N-allyl group may be removed in a two-step process which involves metal-catalyzed isomerization to the enamide 18 followed by hydrolytic removal of the propenyl group to give 19. The position 9 hydroxyl group can then be protected, e.g., with diazomethane to form a methyl ether such as 20. Alkylation of the nitrogen at position 2 in 20 by treatment with a base such as sodium hydride and a halide reagent bearing the $R^1$ group gives 21. Removal of the methyl ether with acid then provides 3.

SCHEME 5

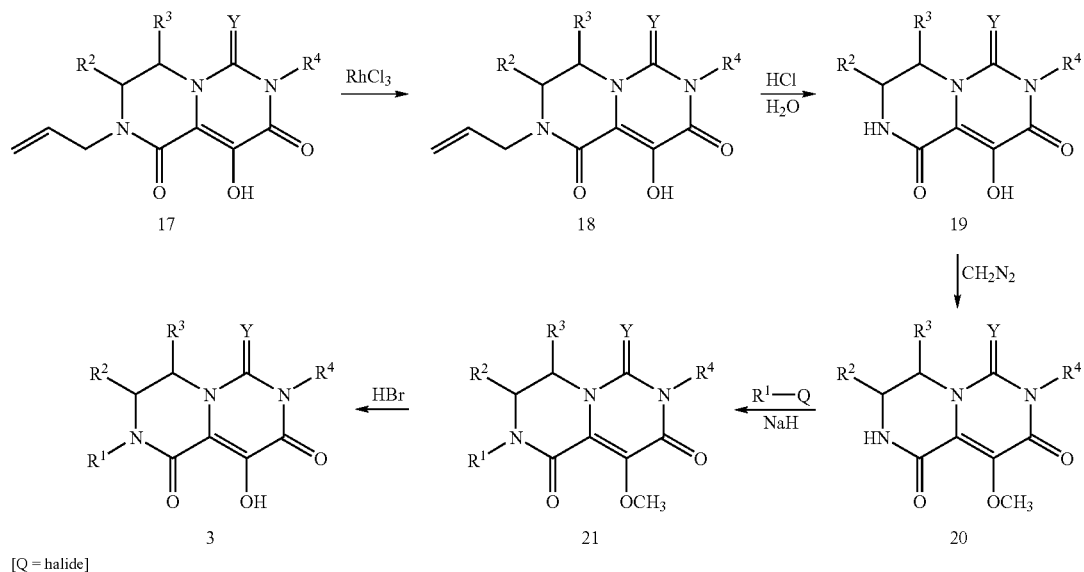

[Q = halide]

Additional $R^2$, $R^3$ and $R^4$ analogs of Formula I may be prepared by synthesizing 3,4-dihydro-2H-pyrazino[1,2-c]pyrimidine-1,6,8(7H)-trione or 6-thioxo-3,4,6,7-tetrahydro-2H-pyrazino[1,2-c]pyrimidine-1,8-dione intermediates which contain substituents at position 3, 4, or 7 suitable for chemical modification. An example of this as a means to produce various $R^4$ analogs of Formula I is given in Scheme 6. Removal of the N-Boc group from the position 7 piperidine substituent in 22 with acid (e.g., TFA) gives amine 23. The free piperidine nitrogen in 23 is then either acylated with an acid anhydride such as acetic anhydride to give 24 or reductively alkylated with a carbonyl compound such as cyclopropane carboxaldehyde and a reducing agent such as sodium cyanoborohydride to give 25. Additional examples of various $R^2$, $R^3$ and $R^4$ analogs of Formula I involving chemical modification of position 3, 4, or 7 substituents are given in the Examples below.

SCHEME 6

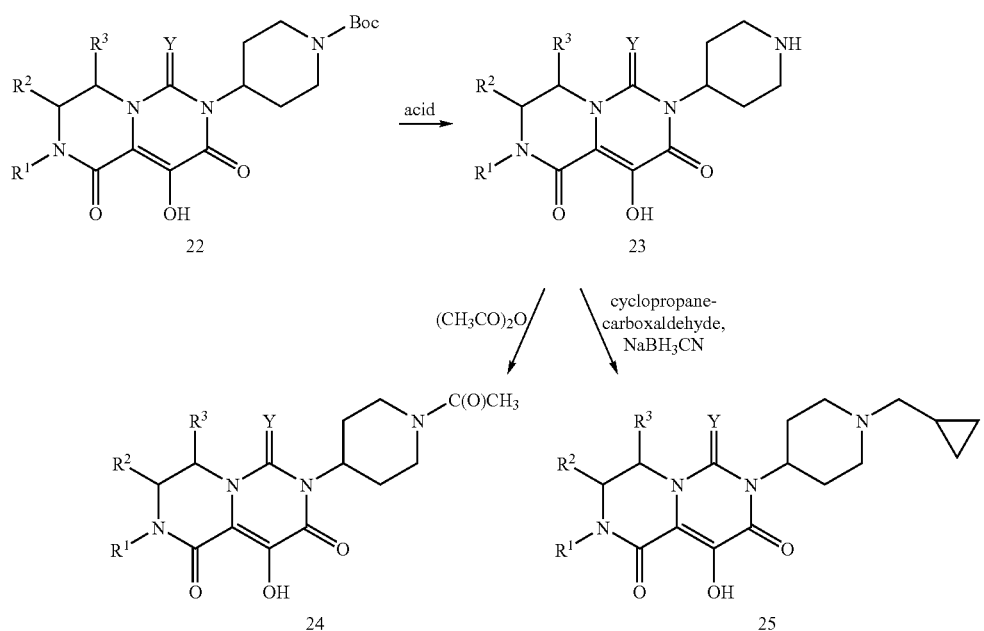

Several methods for preparing compounds of Formula II are shown in Schemes 7, 8, and 9. In Scheme 7, compound 6 from Scheme 2 in which $R^5$ is $C_{1-6}$ alkyl is reacted with a carboxylic acid halide or equivalent reagent to give 26 or with a sulfonyl halide or equivalent reagent to give 27.

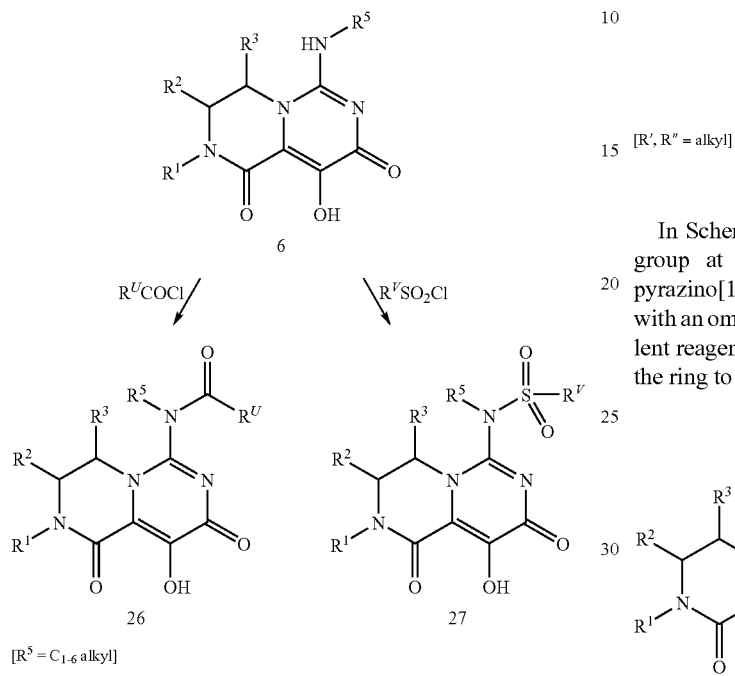

In Scheme 8, compound 4 from Scheme 2 is reacted with a cyclic amine to give 28. Compound 28 is then reacted with a strong base such as lithium bis-trimethylsilylamide and an oxalate ester or equivalent reacent to give 29.

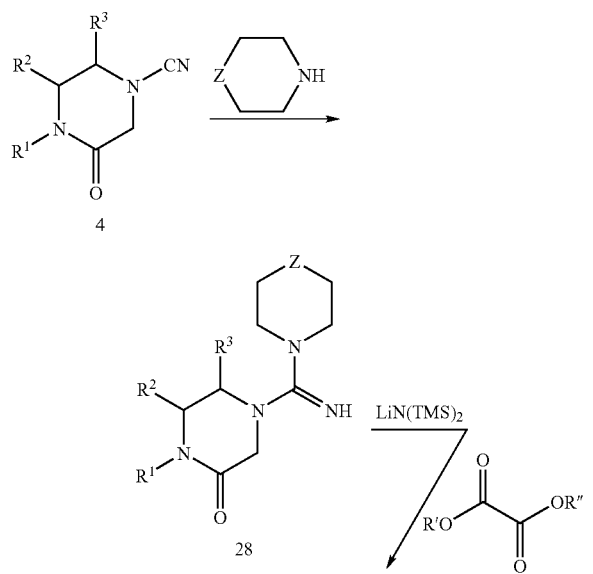

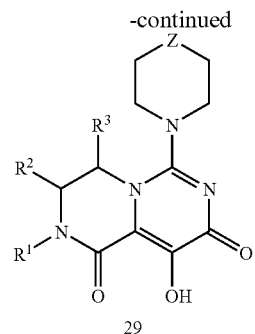

[R′, R″ = alkyl]

In Scheme 9, compound 30, which has a primary amino group at position 6 of the 9-hydroxy-3,4-dihydro-2H-pyrazino[1,2-c]pyrimidine-1,8-dione ring system, is reacted with an omega haloalkyl sulfonyl halide such as 31 or equivalent reagent to give 32. Treatment of 32 with base will close the ring to give 33.

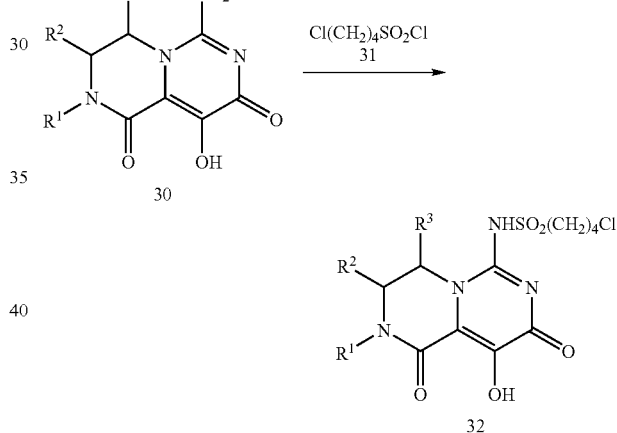

The following examples serve only to illustrate the invention and its practice. The examples are not to be construed as limitations on the scope or spirit of the invention. It is noted that Method A in the examples refers to analytical HPLC data that was obtained using an Agilent Zorbax SB-C8 4.6 mm ID×75 mm 3.5 μm column with a 4.5 min. linear gradient from 95:5 to 0:100 (0.1% TFA in water:0.1% TFA in acetonitrile) at a flow rate of 3 mL/min with UV detection at 215 nm.

EXAMPLE 1

2-(4-fluorobenzyl)-9-hydroxy-7-[(1-morpholin-4-ylcyclopentyl)methyl]-3,4-dihydro-2H-pyrazino[1,2-c]pyrimidine-1,6,8(7H)-trione

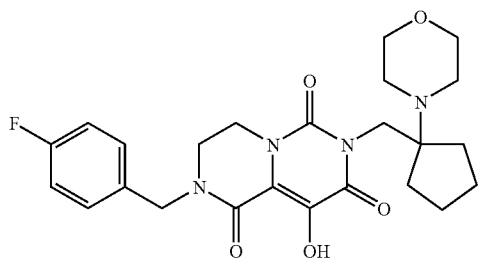

Step 1: N-(2,2-Dimethoxyethyl)-N-(4-fluorobenzyl)amine

A mixture of 4-fluorobenzaldehyde (227.6 g, 1.83 mol) and dimethoxy-ethylamine (192.6 g, 1.83 mol) in methanol (2.5 L) was heated at 65° C. for 1.5 h. The solution was allowed to cool to room temperature overnight and treated with sodium borohydride (47.6 g 1.26 mol) in portions over a period of 2 h. The resultant mixture was stirred at room temperature for 3 h and quenched with water (1 L). The product mixture was concentrated to about 1 L and extracted with diethyl ether (3×). The ethereal extracts were combined, washed with brine, dried over anhydrous sodium sulfate, filtered, and concentrated under vacuum to provide the title compound as yellow oil.

$^1$H NMR (400 MHz, CDCl$_3$) δ 7.28 (dd, J=5.5, 8.6 Hz, 2H), 7.00 (t, J=6.8 Hz, 2H), 4.48 (t, J=5.5 Hz, 1H), 3.77 (s, 2H), 3.37 (s, 6H), 2.73 (d, J=5.5 Hz, 2H); ES MS (M+1)=214.

Step 2: N$^2$-Benzyloxycarbonyl-N$^1$-(2,2-dimethoxyethyl)-N$^1$-(4-fluorobenzyl)-glycinamide To a solution of N-(2,2-dimethoxyethyl)-N-(4-fluorobenzyl)amine (50.6 g, 237.3 mmol), N-CBZ-glycine (54.6 g, 260.8 mmol), EDC (50.0 g, 260.8 mmol), and HOBt (4.2 g, 27 mmol) in anhydrous DMF (500 mL), N,N-diisopropylethylamine (~10 mL) was added until the solution is about pH 7. The reaction mixture was stirred at room temperature overnight and concentrated under vacuum. The residue was partitioned between dichloromethane (1 L) and water (250 mL). The organic extract was washed with brine, dried over anhydrous sodium sulfate, filtered, and concentrated under vacuum to provide the title compound. ES MS (M−OCH$_3$)=374.

Step 3: 4-Benzyloxycarbonyl-1-(4-fluorobenzyl)-3,4-dihydropyrazin-2(1H)-one

To a solution of N$^2$-benzyloxycarbonyl-N$^1$-(2,2-dimethoxyethyl)-N$^1$-(4-fluorobenzyl)glycinamide (61.5 g, 152 mmol) and p-toluenesulfonic acid monohydrate (3 g) in toluene (450 mL) was stirred at 75° C. for 5 days. Each day an additional 3 g of toluenesulfonic acid was added. The resultant reaction mixture was cooled to room temperature and filtered through a pad of Celite. The filtrate was concentrated under vacuum, and the residue dissolved in dichloromethane. The organic solution was washed successively with saturated aqueous sodium bicarbonate, brine, dried over anhydrous sodium sulfate, filtered, and concentrated under vacuum. The residual solid was subjected to column chromatography on silica gel eluting with dichloromethane and then 5% ethyl acetate in dichloromethane. Appropriate fractions were collected and concentrated under vacuum. Residual ethyl acetate and dichloromethane were removed by co-evaporation with toluene 3 times, for the subsequent hydrogenation. The residue was triturated with hexane, and filtered to provide the cyclization product as an off-white solid. $^1$H NMR (400 MHz, CDCl$_3$) δ 7.37 (br s, 5H), 7.23 (m, 2H), 7.02 (t, J=8.6 Hz, 2H), 6.44 (d, J=6.0 Hz, ½H), 6.32 (d, J=6.0 Hz, ½H), 5.53 (d, J=6.0 Hz, ½H), 5.42 (d, J=6.0 Hz, ½H), 5.21 (s, 2H), 4.65 (s, 2H), 4.38 (s, 2H); ES MS (M+1)=341.

Step 4: 1-(4-Fluorobenzyl)piperazin-2-one

A mixture of 4-benzyloxycarbonyl-1-(4-fluorobenzyl)-3,4-dihydro-pyrazin-2(1H)-one (0.5 g, 1.45 mmol) and Pearlman's catalyst (26 mg; 20% palladium hydroxide on carbon) in methanol (25 mL) was stirred under an atmosphere of hydrogen (1 atm) at room temperature overnight. The product mixture was filtered through a pad of Celite, and concentrated under vacuum to provide 1-(4-fluorobenzyl)piperazin-2-one. $^1$H NMR (400 MHz, d$_6$ DMSO) δ 7.29 (dd, J=8.4, 5.7 Hz, 2H), 7.16 (t, J=9.0 Hz, 2H), 4.48 (s, 2H), 3.28 (s, 2H), 3.14 (t, J=5.3 Hz, 2H) 2.84 (t, J=5.3 Hz, 2H); ES MS (M+1)=209.

Step 5: 1-(4-fluorobenzyl)-4-(1H-imidazol-1-ylcarbonyl)piperazin-2-one

To a solution of 1-(4-fluorobenzyl)piperazin-2-one (2.17 grams, 10.4 mmol) in 50 ml MeCN was added 1,1'-carbonyldiimidazole (2.03 g, 12.5 mmol) and dimethylaminopyridine (64 mg, 0.52 mmol). The solution was stirred at room temperature for 1 hour, concentrated under vacuum, and then dissolved in a mixture of CH$_2$Cl$_2$/CHCl$_3$. The organic solution was washed with water three times, dried over anhydrous sodium sulfate, filtered, and concentrated under vacuum. The residue was triturated with diethyl ether, and filtered to provide the title product as a white solid. $^1$H NMR (400 MHz, CDCl3) δ 7.91 (s, 1H), 7.27 (t, J=6.9 Hz, 2H), 7.21 (t, J=1.4 Hz, 1H), 7.13 (s, 1H), 7.05 (t, J=8.6 Hz, 2H), 4.60 (s, 2H), 4.34 (s, 2H), 3.80 (t, J=5.4 Hz, 2H), 3.40 (t, J=5.4 Hz, 2H); ES MS (M+1)=303.

Step 6: 1-{[4-(4-fluorobenzyl)-3-oxopiperazin-1-yl]carbonyl}-3-methyl-1H-imidazol-3-ium iodide To a solution of 1-(4-fluorobenzyl)-4-(1H-imidazol-1-ylcarbonyl)piperazin-2-one (2.49 g, 8.2 mmol) in 20 mL of anhydrous MeCN, under an atmosphere of nitrogen, was added iodomethane (2.05 mL, 32.9 mmol). The reaction was covered in aluminum foil and stirred at room temperature overnight. The reaction was concentrated under vacuum, co-evaporated with toluene under vacuum, followed by drying under high vacuum to provide the title compound. $^1$H NMR (400 MHz, DMSO-d$_6$) δ 9.59 (s, 1H), 8.02 (s, 1H), 7.84 (s, 1H), 7.36 (dd, J=8.4, 5.7 Hz, 2H), 7.19 (t, J=8.7 Hz, 2H), 4.56 (s, 2H), 4.23 (s, 2H), 3.91 (s, 3H), 3.77 (bs, 2H), 3.40 (t, J=5.2 Hz, 2H). ES MS (M)=317.

Step 7: 2-(4-fluorobenzyl)-9-hydroxy-7-[(1-morpholin-4-ylcyclopentyl)methyl]-3,4-dihydro-2H-pyrazino[1,2-c]pyrimidine-1,6,8(7H)-trione To a solution of 1-{[4-(4-fluorobenzyl)-3-oxopiperazin-1-yl]carbonyl}-3-methyl-1H-imidazol-3-ium iodide (75 mg, 0.17 mmol) in 1 mL of anhydrous DMF, under an atmosphere of nitrogen, was added triethylamine (28 μL, 0.20 mmol) and [(1-morpholin-4-ylcyclopentyl)methyl]amine (37 mg, 0.20 mmol) and stirred overnight at room temperature. Dimethyl oxalate (100 μL of 6.76 M DMF solution, 0.67 mmol) and sodium hydride (16 mg, 0.67 mmol) were added, and the reaction mixture was stirred at room temperature. The reaction was quenched with 4 mL of aq $NH_4Cl$, diluted with water, followed by dropwise addition of 1N HCl until slightly acidic. The precipitated product was collected by filtration and rinsed with water, and diethyl ether. Drying under high vacuum provided the title compound. $^1$H NMR (400 MHz, DMSO-$d_6$) δ 11.84 (s, 1H), 7.41 (dd, J=8.5, 5.6 Hz, 2H), 7.17 (bt, J=8.8 Hz, 2H), 4.68 (s, 2H), 4.06 (bs, 2H), 3.94 (bs, 2H), 3.59 (t, J=5.2 Hz, 2H), 3.51 (t, J=4.1 Hz, 4H), 2.64 (t, J=4.1 Hz, 4H), 1.7-1.4 (m, 8H). HRMS ES (M+1) calc'd for $C_{24}H_{30}N_4O_5F$; 473.2195 m/z. found 473.2193 m/z.

EXAMPLE 2

2-(4-Fluorobenzyl)-9-hydroxy-7-methyl-3,4-dihydro-2H-pyrazino[1,2-c]pyrimidine-1,6,8(7H)-trione

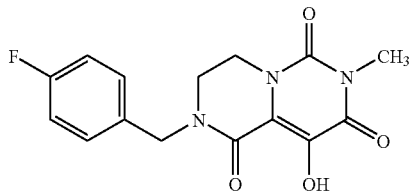

Step 1: 4-(4-Fluorobenzyl)-N-methyl-3-oxopiperazine-1-carboxamide 1-(4-Fluorobenzyl)piperazin-2-one (0.40 g, 1.9 mmol, Example 1, Step 4) was dissolved in anhydrous THF (20 mL) under nitrogen and methyl isocyanate (0.96 mL, 1.9 mmol, 2M solution in THF) was added. The reaction was allowed to stir for two hours at room temperature. The solvent was removed in vacuo and the residue was purified by flash chromatography on silica gel using a 0-5% MeOH/CHCl$_3$ gradient elution. Collection and concentration of the appropriate fractions provided the title compound as a white solid. $^1$H NMR (400 MHz, $d_6$ DMSO) δ 7.29 (m, 2H), 7.16 (m, 2H), 6.55 (d, 1H, J=4.2 Hz), 4.51 (s, 2H), 3.97 (s, 2H), 3.50 (t, 2H, J=5.4 Hz), 3.22 (t, 2H, J=5.4 Hz), and 2.56 (d, 3H, J=4.4 Hz); ES MS (M+1)=266.

Step 2: 2-(4-Fluorobenzyl)-9-hydroxy-7-methyl-3,4-dihydro-2H-pyrazino[1,2-c]pyrimidine-1,6,8(7H)-trione 4-(4-Fluorobenzyl)-N-methyl-3-oxopiperazine-1-carboxamide (200 mg, 0.75 mmol) was dissolved in anhydrous DMF (1.5 mL) under nitrogen and chilled to 0° C. in an ice-water bath. Lithium bis(trimethylsilyl)amide (0.91 mL, 0.91 mmol, 1M solution in THF) was added dropwise and then diethyl oxalate (0.15 mL, 1.13 mmol) was immediately added. The reaction was allowed to warm to room temperature and stirred for one hour. The solvent was removed in vacuo and the residue partitioned between aqueous HCl and ethyl acetate. The layers were separated and the aqueous phase was extracted twice more with ethyl acetate. The combined organic extracts were concentrated in vacuo. The residue was triturated with ethyl acetate and the solids were collected by vacuum filtration to yield the title compound as an off-white solid. $^1$H NMR (400 MHz, $d_6$ DMSO) δ 11.82 (bs, 1H), 7.40 (m, 2H), 7.21 (m, 2H), 4.69 (s, 2H), 3.94 (m, 2H), 3.58 (m, 2H), and 3.21 (s, 3H). HRMS (FT-ICR) $C_{15}H_{14}FN_3O_4$+H=320.1047; calculated 320.1041.

EXAMPLE 3

6-(Benzylamino)-2-(4-fluorobenzyl)-9-hydroxy-3,4-dihydro-2H-pyrazino[1,2-c]pyrimidine-1,8-dione

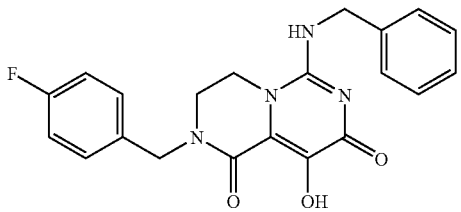

Step 1: 4-(4-Fluorobenzyl)-3-oxopiperazine-1-carbonitrile

To 1-(4-Fluorobenzyl)piperazin-2-one (0.50 g, 2.40 mmol, Example 1, Step 4) dissolved in methylene chloride (75 mL) was added diisopropylethylaime (0.84 mL, 4.80 mmol) and cyanogen bromide (0.28 g, 2.64 mmol) and the resultant solution was stirred overnight at room temperature. The solvent was removed in vacuo and the residue was purified by flash chromatography on silica gel using a 0-5% MeOH/CHCl$_3$ gradient. The pure fractions were concentrated to yield the title compound as a white solid. $^1$H NMR (400 MHz, $d_6$ DMSO) δ 7.31 (m, 2H), 7.18 (m, 2H), 4.54 (s, 2H), 3.98 (s, 2H), 3.49 (m, 2H), and 3.33 (m, 2H); ES MS (M+1)=234.3.

Step 2: N'-Benzyl-4-(4-fluorobenzyl)-3-oxopiperazine-1-carboximidamide

A solution of 4-(4-fluorobenzyl)-3-oxopiperazine-1-carbonitrile (0.56 g, 2.40 mmol) and benzylamine (0.53 mL, 4.80 mmol) in 1,1,1,3,3,3-hexafluoroisopropanol (10 mL) was heated to reflux overnight. The solvent was removed in vacuo and the residue was purified by prep HPLC on a C18 column eluting with a water/acetonitrile/TFA gradient. The pure fractions were concentrated to an oil. The oil was partitioned between aqueous sat. NH$_4$Cl and chloroform. The layers were separated and the aqueous layer was extracted twice more with chloroform. The combined organic extracts were dried over Na$_2$SO$_4$, filtered, and concentrated to give an oil for the title compound. $^1$H NMR (400 MHz, $d_6$ DMSO) before work-up δ 8.29 (t, 1H, J=5.5 Hz), 7.81 (bs, 2H), 7.29-7.40 (m, 7H), 7.19 (t, 2H, J=8.8 Hz), 4.56 (s, 2H), 4.45 (d, 2H, J=5.7 Hz), 4.15 (s, 2H), 3.67 (m, 2H), and 3.39 (m, 2H). ES MS (M+1)=341.3.

Step 3: 6-(Benzylamino)-2-(4-fluorobenzyl)-9-hydroxy-3,4-dihydro-2H-pyrazino[1,2-c]pyrimidine-1,8-dione In a similar manner to Example 2, Step 2, the title compound was prepared from N'-benzyl-4-(4-fluorobenzyl)-3-oxopiperazine-1-carboximidamide and diethyl oxalate in the presence of lithium bis(trimethylsilyl)amide. The crude reaction was purified by prep HPLC on a C18 column, eluting with a water/acetonitrile/TFA gradient, to yield the TFA salt of the title compound as a white solid. $^1$H NMR (400 MHz, $d_6$ DMSO) δ 11.74 (s, 1H), 7.54 (t, 1H, J=5.4 Hz), 7.41 (dd, 2H, J=5.7, 8.4 Hz) 7.31 (m, 4H), 7.18-7.28 (m, 3H), 4.67 (s, 2H), 4.48 (d, 2H, J=5.5 Hz), 3.96 (m, 2H), and 3.65 (m, 2H). HRMS (FT-ICR) $C_{21}H_{19}FN_4O_3$+H=395.1520; calculated 395.1514.

EXAMPLE 4

9-hydroxy-7-isopropyl-2-(quinolin-2-ylmethyl)-3,4-dihydro-2H-pyrazino[1,2-c]pyrimidine-1,6,8(7H)-trione

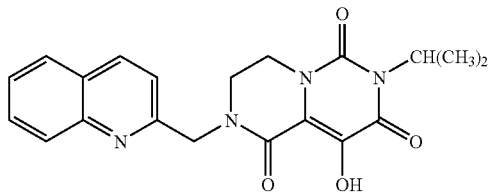

Step 1: 1-(2-Propenyl)-4-tert-butyloxycarbonyl-2-piperazinone

To a stirred solution of 4-tert-butyloxycarbonyl-2-piperazinone (10 g, 50 mmol) and allyl bromide (7.25 g, 60 mmol) in DMF (75 mL) at 0° C. was added sodium hydride (2.4 g of a 60% suspension in mineral oil, 60 mmol) in portions over a period of 10 min. The mixture was allowed to warm to ambient temperature and stirred for 18 h. The solvent was removed in vacuo and the residue was partitioned between EtOAc and water. The EtOAc layer was dried (MgSO$_4$), filtered, and the solvent was removed in vacuo. The residue was purified by silica gel column chromatography using a gradient elution of 33%, 40%, 50%, 60% EtOAc in hexanes. Concentration of product-containing fractions in vacuo gave the title compound as an oil. HPLC RT=2.80 min (Method A), ES MS (M+H)=241, $^1$H NMR (400 MHz, CDCl$_3$) δ 5.76 (ddt, 1H), 5.2 (overlapping doublets, 2H), 4.10 (s, 2H), 4.04 (d, J=6 Hz, 2H), 3.64 (t, J=7 Hz, 2 H), 3.50 (t, J=7 Hz, 2H), 1.47, (s, 9H).

Step 2: 1-(2-Propenyl)-2-piperazinone

Into a stirred solution of 1-(2-propenyl)-4-tert-butyloxycarbonyl-2-piperazinone (11 g, 46 mmol) in EtOAc (100 mL) at 0° C. was bubbled HCl gas for 10 min. The mixture was stirred at 0° C. for 30 min and then at ambient temperature for 1 h. The solvent was removed in vacuo to yield the hydrochloride salt of the title compound as a white solid. ES MS (M+H)=141.

Step 3: 1-(2-Propenyl)-4-(N-2-propylcarbamoyl)-2-piperazinone

To a stirred solution of 1-(2-propenyl)-2-piperazinone hydrochloride (7.9 g, 44 mmol) and diisopropylethylamine (8 mL, 46 mmol) in dichloromethane (100 mL) was added 2-propylisocyanate (5.6 g, 66 mmol). The mixture was stirred at ambient temperature for 18 h. Water (75 mL) was added, and the organic layer was collected, dried (MgSO$_4$), filtered. The solvent was removed in vacuo and the residue was purified by silica gel column chromatography using a gradient elution of 2%, 3%, 4% MeOH in CH$_2$Cl$_2$. Product-containing fractions were combined and concentrated in vacuo to yield 1-(2-propenyl)-4-(N-2-propylcarbamoyl)-2-piperazinone as a solid. HPLC RT=2.17 min (Mehtos A); ES MS (M+H)=226; $^1$H NMR (400 MHz, CDCl$_3$) δ 5.75 (ddt, 1H), 5.2 (overlapping doublets, 2H), 4.32 (b rd, 1H), 4.04 (d, J=6 Hz, 2H), 3.97 (s, 2H), 3.67 (t, J=7 Hz, 2H), 3.33 (t, J=7 hz, 2H), 1.16 (d, J=7 Hz, 6H).

Step 4: 9-Hydroxy-7-isopropyl-2-(2-propenyl)-3,4-dihydro-2H-pyrazino[1,2-c]pyrimidine-1,6,8(7H)-trione To a stirred solution of 1-(2-propenyl)-4-(N-2-propylcarbamoyl)-2-piperazinone (8.0 g, 35 mmol) in DMF (80 mL) at 0° C. was added lithium bis(trimethylsily)amide (40 mL of a 1.0 M solution in THF, 40 mmol). Diethyl oxalate (5.84 g, 40 mmol) was added and the mixture was stirred for 1 h at 0° C. More lithium bis(trimethylsily)amide was added (35 mL of a 1.0 M solution in THF, 35 mmol) and the mixture was stirred for 1 h at 0° C., and then at ambient temperature for 18 h. The reaction was quenched by the addition of 0.5 N aqueous HCl to pH 3 and the solvents were removed in vacuo. The residue was vigorously stirred in methanol-water, and the precipitate was collected by filtration and dried in vacuo to give the title compound. HPLC RT=2.72 min (Method A); ES MS (M+H)= 280; $^1$H NMR (400 MHz, DMSO-d$_6$) δ 11.79 (s, 1H), 5.80 (ddt, 1H), 5.29 (d, J=17 Hz, 1H), 5.22 (d, J=10 Hz, 1H), 5.05 (septet, J=7 Hz, 1H), 4.10 (d, J=7 Hz, 2H), 3.94 (t, J=7 Hz), 3.58 (t, J=7 Hz, 2H), 1.38 (d, J=7 Hz, 6H).

Step 5: 9-hydroxy-7-isopropyl-2-(1-propenyl)-3,4-dihydro-2H-pyrazino[1,2-c]pyrimidine-1,6,8(7H)-trione A mixture of 9-hydroxy-7-isopropyl-2-(2-propenyl)-3,4-dihydro-2H-pyrazino[1,2-c]pyrimidine-1,6,8(7H)-trione (3.0 g, 11 mmol) and rhodium trichloride hydrate (200 mg, 1 mmol) in EtOH (75 mL) was heated to reflux for 8 h. The reaction was cooled to ambient temperature and the solvent was removed in vacuo. The reddish solid was triturated in MeOH and collected by filtration to give the title compound as a solid. HPLC RT=2.90 min (Method A); ES MS (M+H)= 280; $^1$H NMR (400 MHz, DMSO-d$_6$) δ 11.59 (s, 1H), 7.10 (d, J=4.5 Hz, 1H), 5.49 (sextet, J=6 Hz, 1H), 5.04 (septet, J=7 Hz, 1H), 3.97 (m, 2H), 3.79 (m, 2H), 1.76 (d, J=6 Hz, 3H), 1.39 (d, J=7 Hz, 6H).

Step 6: 9-Hydroxy-7-isopropyl-3,4-dihydro-2H-pyrazino[1,2-c]pyrimidine-1,6,8(7H)-trione A solution of 9-hydroxy-7-isopropyl-2-(1-propenyl)-3,4-dihydro-2H-pyrazino[1,2-c]pyrimidine-1,6,8(7H)-trione (1.8 g, 6.4 mmol) in MeOH (15 mL) and 6 N aqueous HCl (10 mL) was heated to reflux for 1 h. The solvents were removed in vacuo and the residue was triturated in MeOH to give the title compound as a solid. HPLC RT=2.14 min (Method A); ES MS (M+H)=240; $^1$H NMR (400 MHz, DMSO-$d_6$) δ 11.5 (v broad s, 1H), 9.19 (s, 1H), 5.04 (septet, J=7 Hz, 1H), 3.87 (t, J=7 Hz, 2H), 3.46 (m, 2H), 1.38 (d, J=7 Hz, 6H).

Step 7: 7-Isopropyl-9-methoxy-3,4-dihydro-2H-pyrazino[1,2-c]pyrimidine-1,6,8(7H)-trione To a solution of 9-hydroxy-7-isopropyl-3,4-dihydro-2H-pyrazino[1,2-c]pyrimidine-1,6,8(7H)-trione (1.0 g, 4.2 mmol) in MeOH (30 mL) was added trimethylsilyldiazomethane (7 mL of a 2.0 M solution in ether, 14 mmol). The mixture was stirred at ambient temperature for 24 h. The solvent was removed in vacuo and the residue was triturated in MeOH and the solid was collected by filtration to give the title compound as a solid. HPLC RT=2.07 min (Method A); ES MS (M+H)=254; $^1$H NMR (400 MHz, DMSO-$d_6$) δ 8.64 (2, 1H), 5.03 (septet, J=7 Hz, 1H), 3.86 (m, 2H), 3.66 (s, 3H), 3.37 (m, 2H), 1.38 (d, J=7 Hz, 6H).

Step 8: 7-Isopropyl-9-methoxy-2-(quinolin-2-ylmethyl)-3,4-dihydro-2H-pyrazino[1,2-c]pyrimidine-1,6,8(7H)-trione To a cold solution (0° C.) of 7-isopropyl-9-methoxy-3,4-dihydro-2H-pyrazino[1,2-c]pyrimidine-1,6,8(7H)-trione (0.050 g, 0.197 mmol) in DMF (1.5 mL) was added 2-(chloromethyl)quinoline hydrochloride (0.051 g, 0.237 mmol). Sodium hydride (60% suspension in mineral oil, 0.022 g, 0.868 mmol) was added. The mixture was warmed to room temperature and stirred for 24 hours. The reaction mixture was partitioned between water and EtOAc. The organic phase was washed with brine, dried over $Na_2SO_4$, filtered, and concentrated in vacuo. The crude product was used in the next step without purification. HPLC RT=3.47 min (Method A); ES MS (M+H)=395.3.

Step 9: 9-hydroxy-7-isopropyl-2-(quinolin-2-ylmethyl)-3,4-dihydro-2H-pyrazino[1,2-c]pyrimidine-1,6,8(7H)-trione Crude 7-isopropyl-9-methoxy-2-(quinolin-2-ylmethyl)-3,4-dihydro-2H-pyrazino[1,2-c]pyrimidine-1,6,8(7H)-trione was stirred in 30% HBr in HOAc (3 mL). The solvents were removed in vacuo after 1 h. The residue was subjected to HPLC purification on C18 stationary phase eluted with water/acetonitrile/TFA mobile phase. Concentration of appropriate tubes afforded the TFA of the title compound. HPLC RT=3.60 min, 99% at 215 nm (Method A); ES MS (M+H)= 381.3; $^1$H NMR (400 MHz, $CD_3OD$) δ 8.86-8.82 (d, 1H) 8.2-8.16 (bd, 2H) 8.06-8.00 (bt, 1H) 7.9-7.8 (m, 2H) 5.24-5.14 (m, 3H) 4.18-4.1 (m, 2H) 3.92-3.86 (m, 2H) 1.5-1.44 (d, 6H).

EXAMPLE 5

7-Cyclopentyl-3-(N,N-dimethylaminocarbonylmethyl)-2-(4-fluorobenzyl)-9-hydroxy-3,4-dihydro-2H-pyrazino[1,2-c]pyrimidine-1,6,8(7H)-trione

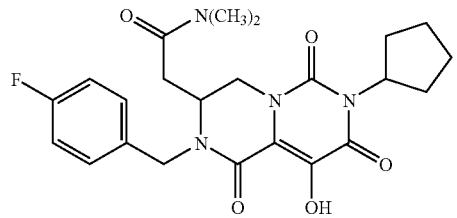

Step 1: Ethyl 5-benzyloxycarbonyl-2-(4-fluorobenzyl)-3-oxo-2,5-diazabicyclo[4.1.0]heptane-7-carboxylate To a suspension of 4-benzyloxycarbonyl-1-(4-fluorobenzyl)-3,4-dihydropyrazin-2(1H)-one (8.9 g, 26.1 mmol, from Example 1, Step 3) and copper bronze (415 mg, 6.53 mmol) in anhydrous toluene (50 mL) under nitrogen at 120° C. (oil bath) was added ethyl diazoacetate (8.3 mL, 78.4 mmol) via a syringe pump at a speed of 2.5 mL/h. After 3 h, TLC (eluted with ethyl acetate) showed no starting material left. The reaction mixture was cooled to room temperature, filtered and concentrated. The residue was purified by column chromatography with silica gel using hexanes and ethyl acetate as eluents to give two diastereomers. Higher $R_f$ isomer: $^1$H NMR (400 MHz, $CDCl_3$) ~2:1 mixture of rotamers δ 7.26-7.38 (m, 7H), 7.02 (t, J=8.6 Hz, 2H), 5.08-5.24 (m, 2H), 4.58-4.70 (m, 2H), 4.34-4.50 (m, 1H), 4.00-4.14 (m, 2H), 3.67-3.80 (m, 1H), 3.50-3.58 (m, 1H), 3.20 (dd, J=7.8, 3.6 Hz, 1H), 1.56-1.62 (m, 1H), 1.20 (t, J=7.1 Hz, 3H). ES MS M+1=427.24. Lower $R_f$ isomer: $^1$H NMR (400 MHz, $CDCl_3$) ~1:1 mixture of rotamers 87.28-7.36 (m, 7H), 6.98-7.04 (m, 2H), 5.05-5.18 (m, 2H), 4.88 (t, J=14.0 Hz, 1H), 4.59 (d, J=17.4 Hz, 0.5H), 4.50 (d, J=17.4 Hz, 0.5H), 4.22 (d, J=14.5 Hz, 0.5H), 4.16 (d, J=14.5 Hz, 0.5H), 3.70-3.96 (m, 3H), 3.50-3.58 (m, 1H), 3.20-3.27 (m, 1H), 1.93 (t, J=6.8 Hz, 0.5H), 1.85 (t, J=6.8 Hz, 0.5H), 1.12 (t, J=7.1 Hz, 1.5H), 1.06 (t, J=7.1 Hz, 1.5H). ES MS M+1=427.24

Step 2: Ethyl [1-(4-fluorobenzyl)-6-oxo-piperazin-2-yl]acetate

The lower Rf isomer of ethyl 5-benzyloxycarbonyl-2-(4-fluorobenzyl)-3-oxo-2,5-diazabicyclo[4.1.0]heptane-7-carboxylate (7.5 g, 17.5 mmol) and 10% palladium on carbon (940 mg; 0.05 mmol) in ethanol (200 mL) was stirred under an atmosphere of hydrogen (1 atm) at room temperature overnight. The product mixture was filtered through a pad of Celite, and concentrated under vacuum to provide the title compound. The structure was assigned by the analysis of HMQC, gHMBC and ROESY spectra. $^1$H NMR (400 MHz, $CDCl_3$) δ 7.24 (dd, J=8.4, 5.3 Hz, 2H), 7.01 (t, J=8.6 Hz, 2H), 5.22 (d, J=15.0 Hz, 1H), 4.13 (q, J=7.2 Hz, 2H), 3.95 (d, J=14.8 Hz, 1H), 3.64-3.80 (m, 1H), 3.61 (d, J=4.5 Hz, 2H), 2.95-3.06 (m, 2H), 2.84 (dd, J=16.1, 9.4 Hz, 1H), 2.59 (dd, J=16.1, 2.4 Hz, 1H), 1.26 (t, J=7.2 Hz, 3H). ES MS (M+1)= 295.32.

Step 3: Ethyl [1-(4-fluorobenzyl)-4-(benzyloxycarbonyl)-6-oxo-piperazin-2-yl]acetate To a solution of ethyl [1-(4-fluorobenzyl)-6-oxo-piperazin-2-yl]acetate (3.7 g, 12.5 mmol) in dichloromethane (100 mL) was added benzyl chloroformate (2.2 mL, 15.1 mmol) and triethylamine (3.5 mL, 25.1 mmol), stirred over night. The reaction mixture was diluted with dichloromethane, washed with 1N HCl, water and brine, dried over sodium sulfate, filtered and concentrated to give the title compound. $^1$H NMR (400 MHz, CDCl$_3$) δ 7.23-7.38 (m, 7H), 7.01 (t, J=8.6 Hz, 2H), 5.12-5.22 (m, 3H), 4.40-4.56 (m, 1H), 3.90-4.24 (m, 5H), 3.72-3.86 (m, 1H), 3.04-3.18 (m, 1H), 2.49-2.62 (m, 2H), 1.12-1.28 (m, 3H). ES MS (M+1)=429.24.

Step 4: [1-(4-Fluorobenzyl)-4-(benzyloxycarbonyl)-6-oxo-piperazin-2-yl]acetic acid To a solution of ethyl [1-(4-fluorobenzyl)-4-(benzyloxycarbonyl)-6-oxo-piperazin-2-yl]acetate (0.5 g, 1.2 mmol) in tetrahydrofuran (2.3 mL) was added 1N sodium hydroxide (2.3 mL, 2.3 mmol). After 2 h, 1N hydrochloric acid (3 mL) was added. The reaction mixture was partitioned between dichloromethane and brine. The organic phase was dried over sodium sulfate, filtered and concentrated to give the title compound. $^1$H NMR (400 MHz, CDCl$_3$) δ 7.23-7.38 (m, 7H), 7.01 (t, J=8.6 Hz, 2H), 5.12-5.20 (m, 3H), 4.45-4.53 (m, 1H), 4.22-4.32 (m, 1H), 3.97 (d, J=15.0 Hz, 2H), 3.78-3.83 (m, 1H), 3.04-3.18 (m, 1H), 2.52-2.67 (m, 2H). ES MS (M+1)=401.2.

Step 5: N,N-dimethyl [1-(4-fluorobenzyl)-4-(benzyloxycarbonyl)-6-oxo-piperazin-2-yl]acetamide To a solution of [1-(4-fluorobenzyl)-4-(benzyloxycarbonyl)-6-oxo-piperazin-2-yl]acetic acid (0.8 g, 2.0 mmol) in THF (30 mL) was added benzotriazol-1-yloxytris(dimethylamino)phosphonium hexafluorophosphate (2.07 g, 4.68 mmol) and dimethylamine (2.0 M in THF, 2.34 mL, 4.68 mmol). The reaction was stirred overnight. The reaction mixture was then diluted with dichloromethane, washed with aqueous hydrochloric acid, brine, dried over sodium sulfate, filtered and concentrated. The residue was purified by column chromatography with silica gel using hexanes and ethyl acetate as eluents to give the title compound. $^1$H NMR (400 MHz, CDCl$_3$) δ 7.23-7.38 (m, 7H), 7.01 (t, J=8.6 Hz, 2H), 5.0-5.24 (m, 3H), 4.45-4.60 (m, 1H), 3.88-4.26 (m, 4H), 3.02-3.20 (m, 1H), 2.62-2.95 (m, 6H), 2.42-2.62 (m, 1H), 2.24 (d, J=15.8 Hz, 1H).

ES MS (M+1)=428.3

Step 6: N,N-dimethyl [1-(4-fluorobenzyl)-6-oxo-piperazin-2-yl]acetamide

A suspension of N,N-dimethyl [1-(4-fluorobenzyl)-4-(benzyloxycarbonyl)-6-oxo-piperazin-2-yl]acetamide (0.5 g, 1.17 mmol) and 10% palladium on carbon (120 mg; 0.11 mmol) in ethanol (25 mL) was stirred under an atmosphere of hydrogen (1 atm) at room temperature overnight. The reaction mixture was filtered through a pad of Celite, and concentrated under vacuum to provide the title compound. $^1$H NMR (400 MHz, CDCl$_3$) δ 7.24-7.28 (m, 2H), 7.01 (t, J=8.6 Hz, 2H), 5.06 (d, J=14.8 Hz, 1H), 4.06 (d, J=14.8 Hz, 1H), 3.87-3.94 (m, 1H), 3.57-3.69 (m, 2H), 2.88-3.08 (m, 9H), 2.48 (d, J=16.3 Hz, 1H). ES MS (M+1)=294.3

Step 7: 7-Cyclopentyl-3-(N,N-dimethylaminocarbonylmethyl)-2-(4-fluorobenzyl)-9-hydroxy-3,4-dihydro-2H-pyrazino[1,2-c]pyrimidine-1,6,8(7H)-trione N,N-dimethyl [1-(4-fluorobenzyl)-6-oxo-piperazin-2-yl] acetamide was converted to the title compound by reaction with carbonyldiimidazole, methylation, urea formation using cyclo-pentylamine, and ring closure with diethyl oxalate and sodium hydride using procedures analogous to those given in Example 1, Steps 5-7. $^1$H NMR (400 MHz, DMSO-d$_6$) δ 11.66 (s, 1H), 7.39 (dd, J=8.0, 5.7 Hz, 2H), 7.20 (t, J=8.4 Hz, 2H), 5.20 (quintet, J=8.6 Hz, 1H), 5.07 (d, J=15.1 Hz, 1H), 4.42 (d, J=13.4 Hz, 1H), 4.38 (d, J=15.1 Hz, 1H), 3.98-4.04 (m, 1H), 3.47 (d, J=13.3 Hz, 1H), 2.87 (s, 3H), 2.79 (s, 3H), 2.78-2.84 (m, 1H), 2.65 (d, J=14.4 Hz, 1H), 1.93-2.06 (m, 2H), 1.80-1.90 (m, 2H), 1.68-1.80 (m, 2H), 1.48-1.60 (m, 2H). HRMS ES (M+1) calc'd for C23H27N4O5F; 459.2038 m/z. found 459.2040 m/z.

EXAMPLE 6

2-(4-Fluorobenzyl)-9-hydroxy-7-isopropyl-4-[2-(N-methoxy-N-methylamino)ethyl]-3,4-dihydro-2H-pyrazino[1,2-c]pyrimidine-1,6,8(7H)-trione

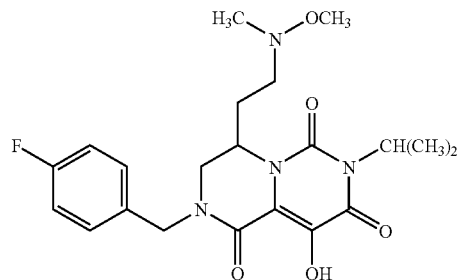

Step 1: Methyl N-(4-fluorobenzyl)glycinate

To a solution of methyl bromoacetate (24.0 mL, 254 mmol) in anhydrous THF (264 mL) was added dropwise triethylamine (35.3 mL, 254 mmol). The cloudy mixture was treated rapidly with 4-fluorobenzylamine, and the resulting viscous mixture was stirred at ambient temperature under inert atmosphere for 18 h. THF was removed in vacuo, and the resulting residue was suspended in diethyl ether. The mixture was filtered and the solids washed with excess diethyl ether. Concentration of the filtrate in vacuo afforded the title compound as a light yellow oil. $^1$H NMR (400 MHz, CDCl$_3$) δ 7.31-7.27 (m, 2H), 7.04-6.99 (m, 2H), 3.77 (s, 2H), 3.74 (s, 3H), 3.41 (s, 2H), 1.82 (br s, 1H).

Step 2: Methyl N-(tert-butoxycarbonyl)-N-(4-fluorobenzyl)glycinate

To a solution of methyl N-(4-fluorobenzyl)glycinate (46.0 g, 233 mmol) in CH$_2$Cl$_2$ (350 mL) were added 4-dimethylaminopyridine (2.85 g, 23.3 mmol) and triethylamine (42.3 mL, 303 mmol). The solution was then treated with 1 M di-tert-butyl dicarbonate in THF (280 mL, 280 mmol), and the reaction was stirred at ambient temperature for 18 h. The solvent was removed in vacuo, and the resulting residue was purified by silica gel chromatography using gradient elution (10% EtOAc/hexanes to 50% EtOAc/hexanes) to afford the title compound as a light yellow oil. $^1$H NMR (400 MHz, CDCl$_3$) δ 7.25-7.18 (m, 2H), 7.03-6.99 (m, 2H), 4.48 (d, J=14.4 Hz, 2H), 3.92 (s, 1H), 3.78 (s, 1H), 3.70 (s, 3H), 1.47 (d, J=2.4 Hz, 9H). ES MS (M+1−100, for loss of BOC group)= 198.0.

Step 3: N-(tert-Butoxycarbonyl)-N-(4-fluorobenzyl)glycine

To a solution of methyl N-(tert-butoxycarbonyl)-N-(4-fluorobenzyl)glycinate (12.4 g, 41.6 mmol) in MeOH (180 mL) was added 5 N aqueous NaOH solution (18.3 mL, 91.6 mmol). The reaction was stirred under inert atmosphere at ambient temperature for 2 h. The solvent was removed in vacuo, and the remaining residue was taken up in water, washing twice with CHCl$_3$. The aqueous layer was cooled to 0° C., acidified to pH 2 with 1 N aqueous HCl solution, and saturated with NaCl. The mixture was extracted with EtOAc three times, and the combined organic layers were dried (MgSO$_4$) and concentrated in vacuo to afford the title acid as a light yellow oil. $^1$H NMR (400 MHz, CDCl$_3$) δ 7.26-7.23 (m, 2H), 7.03 (br s, 2H), 4.50 (d, J=13.6 Hz, 2H), 3.96 (br s, 1H), 3.83 (br s, 1H), 1.49 (s, 9H). ES MS (M+1)=284.20

Step 4: $N^2$-tert-Butyloxycarbonyl-$N^2$-(4-fluorobenzyl)-$N^1$-methoxy-$N^1$-methylglycinamide To a stirred solution of N-(tert-butoxycarbonyl)-N-(4-fluorobenzyl)glycine (10.5 g, 37.2 mmol) in CH$_2$Cl$_2$ (37 mL) was added N,O-dimethylhydroxylamine hydrochloride (3.62 g, 37.2 mmol). The resulting suspension was treated with N-methylmorpholine (4.08 mL, 37.2 mmol) and cooled to 0° C. The mixture was then treated with a 1 M solution of N,N'-dicyclohexylcarbodiimide in CH$_2$Cl$_2$ (37.2 mL, 37.2 mmol) and was then allowed to warm to ambient temperature under inert atmosphere. After stirring for 66 h, the mixture was filtered, washing the solid residue with excess CH$_2$Cl$_2$. The filtrate was concentrated in vacuo and resuspended in EtOAc. After stirring for 1 h, the mixture was filtered, washing the solids with excess EtOAc. The filtrate was again concentrated in vacuo to give an orange oil. Purification by silica gel chromatography (20% to 60% EtOAc/hexanes) afforded the title compound as a colorless oil. $^1$H NMR (400 MHz, CDCl$_3$) δ 7.27-7.20 (m, 2H), 7.03-7.01 (m, 2H), 4.52 (d, J=13.6 Hz, 2H), 4.09 (s, 1H), 3.95 (s, 1H), 3.63 (d, J=20.4 Hz, 3H), 3.18 (s, 3H), 1.47 (s, 9H). ES MS (M+1)=327.17.

Step 5: tert-Butyl 4-fluorobenzyl{4-[methoxy(methyl)amino]-2-oxobutyl}carbamate $N^2$-tert-Butyloxycarbonyl-$N^2$-(4-fluorobenzyl)-$N^1$-methoxy-$N^1$-methylglycinamide (4.91 g, 15.0 mmol) was azeotroped with anhydrous toluene (2×10 mL) and dissolved in anhydrous THF (25 mL). The solution was cooled to 0° C. and treated rapidly with 1 M vinyl magnesium bromide in THF (18.0 mL, 18.0 mmol). After stirring at 0° C. for 10 min, the reaction was allowed to warm to ambient temperature over 1 h and treated with water (18 mL). The mixture was stirred for 20 min and then partitioned between EtOAc and water. The organic layer was washed twice with water, dried (Na$_2$SO$_4$), and concentrated in vacuo to give a red oil. Purification by silica gel chromatography afforded the title compound as an orange oil. $^1$H NMR (400 MHz, CDCl$_3$) δ 7.24-7.16 (m, 2H), 7.03-6.99 (m, 2H), 4.45 (d, J=17.2 Hz, 2H), 4.00 (s, 1H), 3.86 (s, 1H), 3.42 (s, 3H), 2.91-2.85 (m, 2H), 2.63-2.57 (m, 2H), 2.55 (s, 3H), 1.46 (d, J=6.4 Hz, 9H).

Step 6: Methyl N-{1-{[(tert-butoxycarbonyl)(4-fluorobenzyl)amino]methyl}-3-[methoxy(methyl)amino]propyl}glycinate A mixture of glycine methyl ester (2.78 g, 22.1 mmol) in anhydrous THF (13.5 mL) was treated with triethylamine (3.03 mL, 21.6 mmol), tert-butyl 4-fluorobenzyl{4-[methoxy(methyl)amino]-2-oxobutyl}carbamate (1.50 g, 4.23 mmol) in anhydrous THF (8.5 mL), sodium triacetoxyborohydride (5.11 g, 24.1 mmol), and acetic acid (485 µL, 8.46 mmol). The mixture was stirred at ambient temperature under inert atmosphere for 42 h. Saturated aqueous NaHCO$_3$ solution was added and the mixture was stirred until gas evolution ceased. The mixture was extracted into EtOAc, and the aqueous layer was saturated with NaCl and extracted into EtOAc again. The combined organic layers were washed with brine, dried over Na$_2$SO$_4$, and concentrated in vacuo to a pale yellow oil. Purification by silica gel chromatography using gradient elution (hexanes to 40% EtOAc/hexanes to EtOAc) afforded the title compound as a colorless oil. $^1$H NMR (400 MHz, CDCl$_3$) δ 7.19 (br s, 2H), 7.02-6.98 (m, 2H), 4.56-4.37 (m, 2H), 3.72 (s, 3H), 3.49 (s, 3H), 3.39 (br s, 2H), 3.05 (br s, 1H), 2.97 (br s, 1H), 2.66 (br s, 2H), 2.55 (s, 3H), 1.68-158 (m, 4H), 1.47 (br s, 9H). ES MS (M+1)=428.4.

Step 7: 1-(4-Fluorobenzyl)-5-{2-[methoxy(methyl)amino]ethyl}piperazine-2-one A solution of methyl N-{1-{[(tert-butoxycarbonyl)-(4-fluorobenzyl)amino]methyl}-3-[methoxy(methyl)amino]propyl}glycinate (1.63 g, 3.82 mmol) in CH$_2$Cl$_2$ (41 mL) was treated with TFA (12.6 mL) at 0° C. The mixture was stirred at ambient temperature under inert atmosphere for 2 h and then concentrated in vacuo. The resulting oil was suspended in water (46 mL) and treated, portion-wise, with solid K$_2$CO$_3$ (3.1 g). The reaction was heated to 100° C. for 30 min. After cooling to ambient temperature, the mixture was saturated with NaCl and extracted into CH$_2$Cl$_2$ three times. The combined organic layers were dried over Na$_2$SO$_4$ and concentrated in vacuo to yield the title compound as an orange oil. $^1$H NMR (400 MHz, CDCl$_3$) δ 7.29-7.23 (m, 2H), 7.05-6.99 (m, 2H), 4.63 (d, J=14.8 Hz, 1H), 4.47 (d, J=14.8 Hz, 1H), 3.62 (dt, J=17.2, 38.8 Hz, 2H), 3.47 (s, 3H), 3.12-3.10 (m, 1H), 3.08-2.94 (m, 2H), 2.71-2.62 (m, 2H), 2.55 (s, 3H), 1.82 (br s, 1H), 1.63 (dd, J=6.4, 12.4 Hz, 2H). ES MS (M+1)=296.4.

Step 8: 4-(4-Fluorobenzyl)-N-isopropyl-2-{2-[methoxy(methyl)amino]ethyl}-5-oxopiperazine-1-carboxamide A solution of 1-(4-fluorobenzyl)-5-{2-[methoxy(methyl)amino]ethyl}piperazine-2-one (784 mg, 2.65 mmol) in anhydrous CH$_2$Cl$_2$ (13 mL) was treated with isopropyl isocyanate (391 µL, 3.98 mmol) and stirred under inert atmosphere at ambient temperature for 18 h. The solvent was removed in vacuo, and the resulting oil was purified by silica gel chromatography (EtOAc to 5% MeOH/EtOAc to 10% MeOH/EtOAc) to afford the title urea as a light orange oil.

$^1$H NMR (400 MHz, CDCl$_3$) δ 7.28-7.24 (m, 2H), 7.06-7.00 (m, 2H), 4.81 (d, J=14.8 Hz, 1H), 4.62-4.58 (m, 1H), 4.36 (d, J=14.4 Hz, 1H), 4.26 (br s, 1H), 3.95-3.87 (m, 1H), 3.71 (d, J=18.4 Hz, 1H), 3.61-3.53 (m, 1H), 3.50 (s, 3H), 2.99 (dd, J=1.6, 12.4 Hz, 1H), 2.53 (s, 3H), 2.52 (br s, 3H), 1.78-1.70 (m, 1H), 1.17-1.14 (m, 6H). ES MS (M+1)=381.4.

Step 9: 2-(4-Fluorobenzyl)-9-hydroxy-7-isopropyl-4-[2-(N-methoxy-N-methylamino)ethyl]-3,4-dihydro-2H-pyrazino[1,2-c]pyrimidine-1,6,8(7H)-trione 4-(4-Fluorobenzyl)-N-isopropyl-2-{2-[methoxy(methyl)amino]ethyl}-5-oxopiperazine-1-carboxamide (777 mg, 2.04 mmol) was azeotroped with anhydrous toluene (10 µL) and dissolved in anhydrous DMF (10 mL). The solution was cooled to 0° C. under inert atmosphere and treated with 1.0 M lithium bis(trimethylsilyl)amide in THF (2.45 mL, 2.45 mmol). After stirring for 10 min, diethyl oxalate (416 µL, 3.06 mmol) was added. The mixture was stirred at 0° C. for an additional 15 min and then allowed to warm to ambient temperature. Following addition of excess 1.0 M lithium bis(trimethylsilyl)amide in THF (7.30 mL, 7.30 mmol), the reaction was stirred at ambient temperature for 18 h. The mixture was treated with MeOH and concentrated in vacuo to give a dark oil. Purification by reverse phase chromatography [95:5 water (+0.1% TFA)/MeCN (+0.1% TFA) to 5:95 water (+0.1% TFA)/MeCN (+0.1% TFA)] afforded the title compound as tan foam. $^1$H NMR (400 MHz, $d_6$-DMSO) δ 11.78 (br s, 1H), 7.44-7.41 (m, 2H), 7.24-7.19 (m, 2H), 5.04 (dt, J=6.4, 13.6 Hz, 1H), 4.84 (d, J=14.8 Hz, 1H), 4.72 (br s, 1H), 4.51 (d, J=14.4 Hz, 1H), 3.77 (dd, J=3.6, 13.2 Hz, 1H), 3.43 (d, J=13.6 Hz, 1H), 3.31 (s, 3H), 2.36 (s, 3H), 2.33-2.31 (m, 2H), 1.71-1.62 (m, 1H), 1.51-1.43 (m, 1H), 1.37 (d, J=6.8 Hz, 6H). HRMS (FT/ES) M+H: calcd for $(C_{21}H_{27}FN_4O_5)^+$ 435.2038. found 435.2038.

EXAMPLE 7

7-(Cyclohexylmethyl)-2-(4-fluorobenzyl)-9-hydroxy-6-thioxo-3,4,6,7-tetrahydro-2H-pyrazino[1,2-c]pyrimidine-1,8-dione

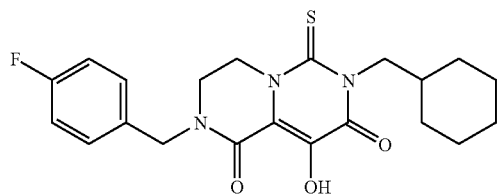

Step 1: N-(Cyclohexylmethyl)-4-(4-fluorobenzyl)-3-oxopiperazine-1-carbothioamide To a cold (0° C.) solution of 1-(4-fluorobenzyl)piperazin-2-one (150 mg, 0.72 mmol) in EtOAc (2 mL) was added cyclohexyl isothiocyanate (117 µL, 0.76 mmol). The reaction was stirred at ambient temperature for 4 h, and the resulting precipitate was collected by filtration and washed with diethyl ether to afford the title thiourea as a white powder. ES MS (M+H): 364.3.

Step 2: 7-(Cyclohexylmethyl)-2-(4-fluorobenzyl)-9-hydroxy-6-thioxo-3,4,6,7-tetrahydro-2H-pyrazino[1,2-c]pyrimidine-1,8-dione N-(Cyclohexylmethyl)-4-(4-fluorobenzyl)-3-oxopiperazine-1-carbothioamide (239 mg, 0.66 mmol) was azeotroped with anhydrous toluene and dissolved in anhydrous DMF (2 mL). The solution was cooled to 0° C., and a 1.0 M solution of lithium bis(trimethylsilyl)amide in THF (789 µL, 0.79 mmol) and diethyl oxalate (134 µL, 0.99 mmol) were added sequentially. After 15 min, the reaction was warmed to ambient temperature and treated once more with 1.0 M lithium bis(trimethylsilyl)amide in THF (789 µL, 0.79 mmol). The dark orange solution was stirred for 18 h. THF was removed by warming the reaction under a nitrogen stream, and the residue was diluted with MeOH. The resulting precipitate was collected by filtration and washed with MeOH to afford the title compound as a pale yellow solid.
$^1$NMR (400 MHz, CDCl$_3$) δ 7.24-7.21 (m, 2H), 6.97-6.93 (m, 2 H), 5.07 (br s, 2H), 4.39 (br s, 4H), 3.31-3.30 (m, 2H), 2.10-1.93 (m, 2H), 1.75-1.52 (m, 6H), 1.22-1.01 (m, 4H). HRMS (FT/ES) M+H: calcd for $(C_{21}H_{24}FN_3O_3S)^+$ 418.1595. found 418.1612.

EXAMPLE 8

Racemic-(7R,9aS)-4-hydroxy-2-isopropyl-7-phenyl-8,9,9a,10-tetrahydro-7H-pyrrolo[1',2':4,5]pyrazino[1,2-c]pyrimidine-1,3,5(2H)-trione

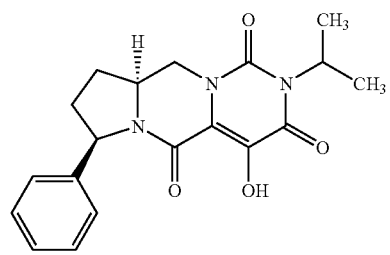

Step 1: 1-tert-butyloxycarbonyl-cis-2-{[methoxy(methyl)amino]carbonyl}-5-phenylpyrrolidine A solution of racemic N-Boc-cis-5-phenylproline (2 g, 6.865 mmol) in DMF (35 mL) was added HOBt (1.05 g, 6.87 mmol), EDC (1.97 g, 10.3 mmol), O, N-dimethylhydroxylamine hydrochloride (1.00 g, 10.3 mmol) and DIEA dropwise (1.33 mL, 10.3 mmol). The reaction was stirred at ambient temperature for 30 min and then partitioned between ethyl acetate and water. The EtOAc layer was separated and washed with brine, dried over anhydrous sodium sulfate, filtered, and concentrated under vacuum. The residue was subjected to column chromatography on silica gel eluting with 50:50 ethyl acetate and hexane. Collection and concentration of appropriate fractions provided the title compound. HPLC RT=3.46 min, 86% at 215 nm (Method A); ES MS (M+H)=335.3.

Step 2: 1-tert-butyloxycarbonyl-cis-2-formyl-5-phenylpyrrolidine

To a cold (−78° C.) solution of 1-tert-butyloxycarbonyl-cis-2-{[methoxy(methyl)amino]carbonyl}-5-phenylpyrrolidine (1.36 g, 4.07 mmol) in THF (20 mL) under an atmosphere of nitrogen, a 1M solution of LAH in THF (4.07 mL, 4.07 mmol) was added dropwise and the mixture was stirred for 30 min. The mixture was warmed to 0° C. for 30 min and then quenched with potassium bisulfate solution in water (0.969 g, 7.12 mmol). EtOAc was added and the organic phase was separated, washed with brine, dried over anhydrous sodium sulfate, filtered, and concentrated under vacuum. The residue was subjected to column chromatography on silica gel eluting with a 50:50 mixture of ethyl acetate and hexane. Collection and concentration of appropriate fractions provided 1-tert-butyloxycarbonyl-cis-2-formyl-5-phenylpyrrolidine. HPLC RT=3.47 min, 99% at 215 nm (Method A); ES MS (M+H)=276.3.

Step 3: 1-tert-butyloxycarbonyl-cis-2-[(N-benzyl-N-ethoxycarbonylmethyl)aminomethyl]-5-phenylpyrrolidine To a solution of 1-tert-butyloxycarbonyl-cis-2-formyl-5-phenylpyrrolidine (1.11 g, 4.03 mmol) in dichloromethane (20 mL) under nitrogen was added N-benzylglycine ethyl ester (0.771 g, 4.03 mmol), followed by sodium triacetoxyborohydride (1.7 g, 8.06 mmol). After 10 min, the solvent was concentrated under vacuum and partitioned between ethyl acetate and water. The organic layer was washed with brine, dried over anhydrous sodium sulfate, filtered, and concentrated under vacuum. The residue was subjected to column chromatography on silica gel eluting with a 50:50 mixture of ethyl acetate and hexane. Collection and concentration of appropriate fractions provided the title compound. HPLC RT=3.5 min, 95% at 215 nm (Method A); ES MS (M+H)=453.3.

Step 4: (6R,8aS)-2-benzyl-6-phenylhexahydropyrrolo[1,2-a]pyrazin-4(1H)-one

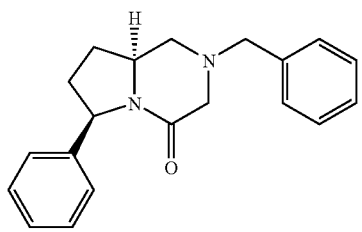

A solution of 1-tert-butyloxycarbonyl-cis-2-[(N-benzyl-N-ethoxycarbonylmethyl)aminomethyl]-5-phenylpyrrolidine (1.28 g, 2.83 mmol) in dichloromethane (10 mL) was added TFA (10 mL) and the mixture was stirred for 10 min. The solvents were removed under vacuum and the residue was partitioned between ethyl acetate and aqueous sodium bicarbonate. The organic layer was washed with brine, dried over anhydrous sodium sulfate, filtered, and concentrated under vacuum. The residue was dissolved in toluene (15 mL) and heated to reflux for 30 min. Removal of the toluene under vacuum provided the title compound. HPLC RT=2.41 min (Method A); ES MS (M+H)=307.3.

Step 5: (6R,8aS)-6-phenylhexahydropyrrolo[1,2-a]pyrazin-4(1H)-one

To a solution of racenic-(6R,8aS)-2-benzyl-6-phenyl-hexahydropyrrolo[1,2-a]pyrazin-4(1H)-one (1.12 g, 3.47 mmol) in methanol (15 mL) was added 12 N HCl (0.2 mL). The solution was degassed with nitrogen. 10% Palladium on carbon (0.50 g) was added and the mixture was shaken on a Parr apparatus under 50 psi of hydrogen for 3 h. The catalyst was removed by filtration through celite and the filtercake was washed with ethyl acetate. Removal of the solvents under vacuum provided the HCl salt of the title compound. HPLC RT=2.01 min, 97% at 215 nm (Method A); ES MS (M+H)=217.3.

Step 6: (6R,8aS)-N-isopropyl-4-oxo-6-phenyl-hexahydropyrrolo[1,2-a]pyrazine-2(1H)-carboxamide To a solution of the HCl salt of racemic-(6R,8aS)-6-phenylhexahydropyrrolo[1,2-a]pyrazin-4(1H)-one (0.25 g, 0.99 mmol) and DIEA (0.345 mL, 1.99 mmol) in dichloromethane (4 mL) at ambient temperature was added isopropyl isocyanate (0.146 mL, 1.48 mmol). The mixture was stirred at ambient temperature for 18 h. The solvent was removed under vacuum and the residue was partitioned between ethyl acetate and brine. The EtOAc layer was separated, dried over anhydrous sodium sulfate, filtered, and concentrated under vacuum. The residue was subjected to HPLC purification on C-18 stationary phase eluted with water/acetonitrile/TFA mobile phase. Concentration of appropriate fractions afforded (6R,8aS)-N-isopropyl-4-oxo-6-phenylhexahydropyrrolo[1,2-a]pyrazine-2(1H)-carboxamide. HPLC RT=2.68 min (Method A); ES MS (M+H)=302.3.

Step 7: (7R,9aS)-4-hydroxy-2-isopropyl-7-phenyl-8,9,9a,10-tetrahydro-7H-pyrrolo[1',2':4,5]pyrazino[1,2-c]pyrimidine-1,3,5(2H)-trione To a solution of racemic (6R,8aS)-N-isopropyl-4-oxo-6-phenylhexahydropyrrolo[1,2-a]pyrazine-2(1H)-carboxamide (0.187 g, 0.620 mmol) in DMF (3 mL) at 0° C. was added a 1M solution of lithium bis(trimethylsilyl)amide in THF (1.49 mL, 1.49 mmol), followed by diethyl oxalate (0.101 mL, 0.745 mmol). The mixture was stirred for 18 h, allowing the cooling bath to warm to ambient temperature. The resultant mixture was then treated with additional lithium bis(trimethylsilyl)amide in THF (1.49 mL, 1.49 mmol) and stirred at room temperature for 6 h. The product mixture was concentrated under vacuum and the residue was partitioned between aqueous HCl and ethyl acetate. The organic extract was concentrated under vacuum. The residue was subjected to HPLC purification on C18 stationary phase eluted with water/acetonitrile/TFA mobile phase to give the title compound as a solid. HPLC RT=3.19 min, 95% at 215 nm (Method A); ES MS (M+H)=356.2; $^1$H NMR (400 MHz, DMSO-$d_6$) δ 7.32-7.24 (m, 2H) 7.22-7.16 (m, 3H) 5.12-5.02 (m, 2H) 4.80-4.74 (d, 1H) 3.84-3.74 (m, 1H) 2.38-2.28 (m, 1H) 2.06-1.98 (m, 1H) 1.74-1.66 (m, 1H) 1.42-1.34 (dd, 6H) 1.34-1.26 (m, 1H).

EXAMPLE 9

2-(4-Fluorobenzyl)-9-hydroxy-7-[(1R,2S)-2-phenyl-cyclopropyl]-3,4-dihydro-2H-pyrazino[1,2-c]pyrimidine-1,6,8(7H)-trione

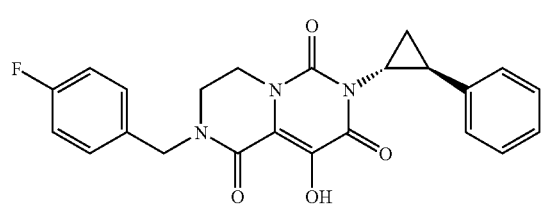

In a similar manner to the synthesis of Example 2, the title compound was prepared using trans-2-phenylcyclopropyl isocyanate in the first step. The crude reaction from Step 1 was taken on without further purification to Step 2. The title compound was isolated by prep HPLC using a C18 stationary phase eluting and a water/acetonitrile/TFA gradient. Concentration of appropriate fractions gave the title compound as an off-white solid. $^1$H NMR (400 MHz, $d_6$ DMSO) δ 11.87 (s, 1H), 7.39 (dd, 2H, J=5.7, 8.2 Hz), 7.28 (m, 5H), 7.21 (t, 2H, J=8.7 Hz), 4.69 (s, 2H), 3.93 (m, 2H), 3.58 (m, 2H), 2.72 (m, 1H), 2.20 (m, 1H), 1.58 (m, 1H), and 1.33 (m, 1H). HRMS (FT-ICR) $C_{23}H_{20}FN_3O_4$+H=422.1509; calculated 422.1511.

EXAMPLE 10

7-(1-Adamantyl)-2-(4-fluorobenzyl)-9-hydroxy-3,4-dihydro-2H-pyrazino[1,2-c]pyrimidine-1,6,8(7H)-trione

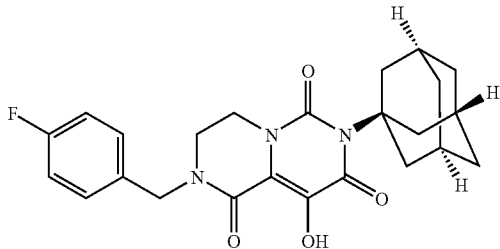

The procedures of Example 9 were employed, using 1-adamantylisocyanate. Purification by prep HPLC using a C18 stationary phase eluting and a water/acetonitrile/TFA gradient gave the title compound as a solid. $^1$H NMR (400 MHz, $d_6$ DMSO) δ 11.77 (s, 1H), 7.38 (dd, 2H, J=5.7, 8.4 Hz), 7.20 (t, 2H, J=8.7 Hz), 4.66 (s, 2H), 3.80 (m, 2H), 3.54 (m, 2H), 2.44 (m, 6H), 2.08 (m, 3H), and 1.65 (m, 6H). HRMS (FT-ICR) $C_{24}H_{26}FN_3O_4$+H=440.1982; calculated 440.1980.

EXAMPLE 11

2-(4-Fluorobenzyl)-9-hydroxy-7-[1-(1-naphthyl) ethyl]-3,4-dihydro-2H-pyrazino[1,2-c]pyrimidine-1, 6,8(7H)-trione

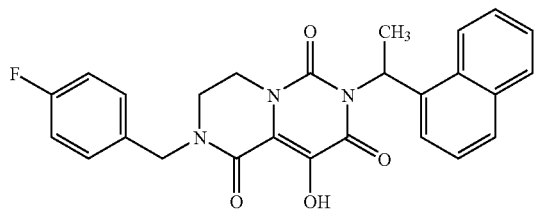

The procedures of Example 9 were employed, using 1-(1-naphthyl)ethylisocyanate. Purification by prep HPLC using a C18 stationary phase eluting and a water/acetonitrile/TFA gradient gave the title compound as a solid. $^1$H NMR (400 MHz, $d_6$ DMSO) δ 11.80 (s, 1H), 7.93 (m, 1H), 7.86 (m, 3H), 7.46-7.55 (m, 3H), 7.36 (dd, 2H, J=5.7, 8.4 Hz), 7.16 (t, 2H, J=8.8 Hz), 6.68 (m, 1H), 4.63 (s, 2H), 3.86 (m, 2H), 3.51 (t, 2H, J=5.5 Hz), and 1.89 (d, 3H, J=7.0 Hz). HRMS (FT-ICR) $C_{26}H_{22}FN_3O_4$+H=460.1665; calculated 460.1667.

EXAMPLE 12

2-(4-Fluorobenzyl)-9-hydroxy-7-(piperidin-4-yl)-3,4-dihydro-2H-pyrazino[1,2-c]pyrimidine-1,6,8(7H)-trione

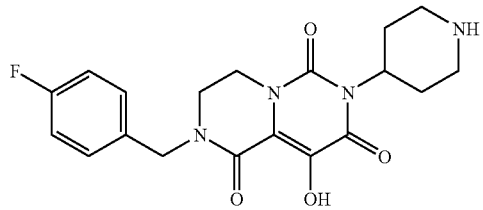

In a similar manner to Example 1, step 7,4-amino-1-BOC-piperidine was reacted with 1-{[4-(4-fluorobenzyl)-3-oxopiperazin-1-yl]carbonyl}-3-methyl-1H-imidazol-3-ium iodide and then cyclized in situ. The crude reaction was pipetted into aq. sat. NH$_4$Cl solution and the pH adjusted to 4 using aq. 1N HCl. The water layer was poured off and the remaining gum was dissolved in DMF and purified by prep HPLC on a C18 stationary phase and eluting with a water/acetonitrile/TFA gradient. The pure fractions were combined and concentrated to an orange solid which was then dissolved in methylene chloride (3 mL) and treated with TFA (0.5 mL) and stirred for 18 h. The solvent was removed in vacuo and the residue was purified by prep HPLC on a C18 stationary phase and eluting with a water/acetonitrile/TFA gradient. Concentration of appropriate fractions gave the TFA salt of the title compound. $^1$H NMR (400 MHz, $d_6$ DMSO) δ 11.81 (s, 1H), 8.68 (m, 1H), 8.33 (m, 1H), 7.39 (dd, 2H, J=5.6, 8.5 Hz), 7.21 (t, 2H, J=8.8 Hz), 4.97 (m, 1H), 4.69 (s, 2H), 3.94 (m, 2H), 3.58 (m, 2H), 3.36 (d, 2H, J=12.1 Hz), 3.05 (m, 2H), 2.72 (m, 2H), and 1.73 (d, 2H, J=12.5 Hz). ES MS (M+1)=389.3.

EXAMPLE 13

7-(1-Acetylpiperidin-4-yl)-2-(4-fluorobenzyl)-9-hydroxy-3,4-dihydro-2H-pyrazino[1,2-c]pyrimidine-1,6,8(7H)-trione

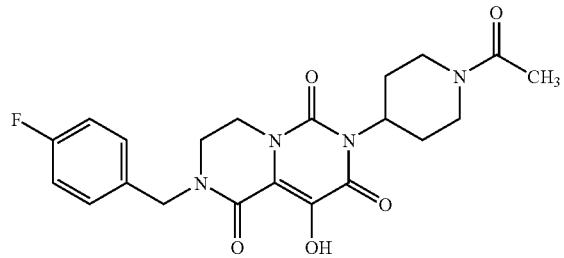

To 2-(4-Fluorobenzyl)-8,9-dihydroxy-7-(piperidin-4-ylmethyl)-3,4-dihydro-2H-pyrido[1,2-a]pyrazine-1,6-dione TFA salt (50 mg, 0.10 mmol, Example 12) in dry methylene chloride (2 mL) was added pyridine (10 μL, 0.12 mmol) and acetic anhydride (11 μL, 0.12 mmol). The reaction was stirred overnight at room temperature. The crude reaction was purified by prep HPLC on a C18 stationary phase and eluting with a water/acetonitrile/TFA gradient. The title compound was obtained as a white solid after lyophilization from dioxane. $^1$H NMR (400 MHz, $d_6$ DMSO) δ 11.80 (bs, 1H), 7.39 (dd, 2H, J=5.7, 8.6 Hz), 7.20 (t, 2H, J=8.8 Hz), 4.91 (m, 1H), 4.68 (s, 2H), 4.48 (d, 1H, J=13.0 Hz), 3.91 (m, 3H), 3.58 (m, 2H), 3.08 (m, 1H), 2.41-2.57 (m, 2H), 2.31 (m, 1H), 2.01 (s, 3H), and 1.56 (d, 2H, J=14.5 Hz). ES MS (M+1)=431.3.

EXAMPLE 14

7-[1-(Cyclopropylmethyl)piperidin-4-yl]-2-(4-fluorobenzyl)-9-hydroxy-3,4-dihydro-2H-pyrazino[1,2-c]pyrimidine-1,6,8(7H)-trione

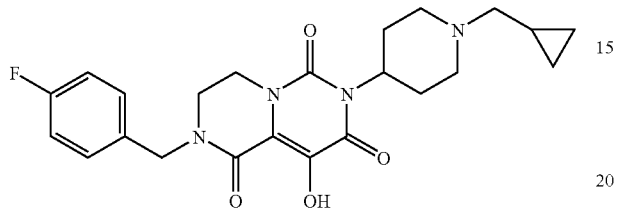

To 2-(4-Fluorobenzyl)-8,9-dihydroxy-7-(piperidin-4-ylmethyl)-3,4-dihydro-2H-pyrido[1,2-a]pyrazine-1,6-dione mono TFA salt (50 mg, 0.10 mmol, Example 12) in dry methanol was added cyclopropane carboxaldehyde (19 μL, 0.25 mmol) and pyridine (10 μL, 0.12 mmol). The reaction was stirred for 1 h and then sodium cyanoborohydride (8 mg, 0.12 mmol) was added. After overnight, more cyclopropane carboxaldehyde (19 μL, 0.25 mmol) and sodium cyanoborohydride (8 mg, 0.12 mmol) were added. After one hour, the reaction was concentrated and the residue was purified by prep HPLC on a C18 stationary phase and eluting with a water/acetonitrile/TFA gradient. The TFA salt of the title compound was obtained as a white solid after lyophilizing from dioxane. $^1$H NMR (400 MHz, $d_6$ DMSO) δ 11.82 (s, 1H), 9.37 (bs, 1H), 7.39 (dd, 2H, J=5.7, 8.4 Hz), 7.21 (t, 2H, J=8.8 Hz), 4.97 (m, 1H), 4.70 (s, 2H), 3.94 (m, 2H), 3.57-3.64 (m, 4H), 3.13 (m, 2H), 2.97 (m, 2H), 2.84 (m, 2H), 1.81 (d, 2H, J=12.6 Hz), 1.06 (m, 1H), 0.65 (m, 2H), and 0.36 (m, 2H). ES MS (M+1)=443.3.

EXAMPLE 15

2-(4-Fluorobenzyl)-9-hydroxy-7-[1-(morpholin-4-ylacetyl)piperidin-4-yl]-3,4-dihydro-2H-pyrazino[1,2-c]pyrimidine-1,6,8(7H)-trione

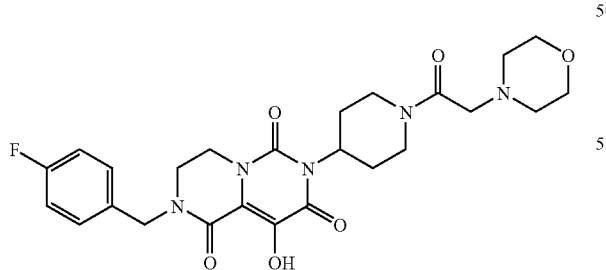

To 2-(4-Fluorobenzyl)-8,9-dihydroxy-7-(piperidin-4-ylmethyl)-3,4-dihydro-2H-pyrido[1,2-a]pyrazine-1,6-dione mono TFA salt (50 mg, 0.10 mmol, Example 12) in DMF (1 mL) was added 1-(3-dimethylaminopropyl)-3-ethylcarbodiimide hydrochloride (29 mg, 0.15 mmol), 1-hydroxybenzotriazole hydrate (23 mg, 0.15 mmol), triethylamine (31 μL, 0.22 mmol), and 2-morpholinoacetic acid HCl (22 mg, 0.12 mmol). The reaction was stirred overnight and then purified by prep HPLC on a C18 stationary phase and eluting with a water/acetonitrile/TFA gradient. The TFA salt of the title compound was obtained as a white solid after lyophilizing from dioxane. $^1$H NMR (400 MHz, $d_6$ DMSO) δ 11.81 (s, 1H), 10.03 (bs, 1H), 7.39 (dd, 2H, J=5.7, 8.4 Hz), 7.21 (t, 2H, J=8.8 Hz), 4.98 (m, 1H), 4.69 (s, 2H), 4.47 (m, 2H), 4.36 (m, 1H), 3.90-4.02 (m, 4H), 3.80 (m, 2H), 3.64 (m, 2H), 3.57 (m, 3H), 3.44 (m, 2H), 3.18 (m, 2H), 2.78 (m, 1H), 2.39 (m, 1H), and 1.65 (m, 2H). HRMS (FT-ICR $C_{25}H_{30}FN_5O_6$+H)= 516.2261; calculated 516.2253.

EXAMPLE 16

7-[(4-Benzylmorpholin-3-yl)methyl]-2-(4-fluorobenzyl)-9-hydroxy-3,4-dihydro-2H-pyrazino[1,2-c]pyrimidine-1,6,8(7H)-trione

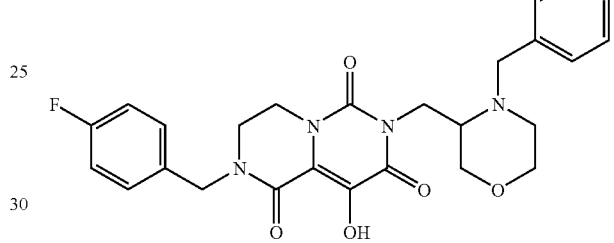

In a similar manner to Example 1, Step 7, 4-benzylmorpholin-3-ylmethylamine was reacted with 1-{[4-(4-fluorobenzyl)-3-oxopiperazin-1-yl]carbonyl}-3-methyl-1H-imidazol-3-ium iodide and then cyclized in situ. The crude reaction was purified by prep HPLC on a C18 stationary phase and eluting with a water/acetonitrile/TFA gradient to obtain the TFA salt of the title compound as an orange solid. HRMS (FT-ICR) $C_{26}H_{27}FN_4O_5$+H=495.2065; calculated 495.2038.

EXAMPLE 17

2-(4-Fluorobenzyl)-9-hydroxy-7-(3-morpholinylmethyl)-3,4-dihydro-2H-pyrazino[1,2-c]pyrimidine-1,6,8(7H)-trione

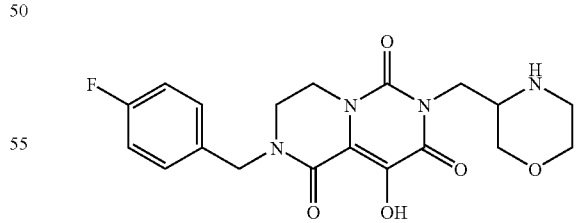

7-[(4-Benzylmorpholin-3-yl)methyl]-2-(4-fluorobenzyl)-9-hydroxy-3,4-dihydro-2H-pyrazino[1,2-c]pyrimidine-1,6,8(7H)-trione TFA salt (921 mg, 1.86 mmol, from Example 16) was dissolved in degassed ethanol (10 mL) under nitrogen and 10% palladium on carbon (92 mg) was added. The flask was evacuated and purged with hydrogen three times using a vacuum line and a hydrogen gas balloon. The reaction was stirred overnight under a hydrogen gas atmosphere. The reaction was filtered through a thin pad of celite, washing with degassed ethanol. The filtrate was concentrated to a yellow solid which was triturated with methanol. The solids were collected by vacuum filtration to give the desired product as a white powder. $^1$H NMR (400 MHz, $d_6$ DMSO) δ 11.9 (s, 1H), 8.96 (bs, 2H), 7.39 (m, 2H), 7.22 (m, 2H), 4.72 (s, 2H), 4.13 (m, 1H), 3.84-4.02 (m, 5H), 3.52-3.70 (m, 5H), 3.27 (m, 1H), and 3.05 (m, 1H). HRMS (FT-ICR $C_{19}H_{21}FN_4O_5$+H)= 405.1572; calculated 405.1569.

EXAMPLE 18

2-(3-{[2-(4-Fluorobenzyl)-9-hydroxy-1,6,8-trioxo-1,3,4,8-tetrahydro-2H-pyrazino[1,2-c]pyrimidin-7(6H)-yl]methyl}morpholin-4-yl)-N,N-dimethyl-2-oxoacetamide

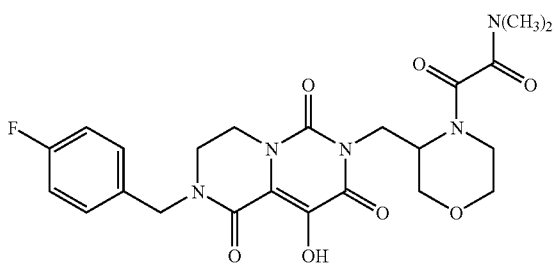

To a solution of 2-(4-Fluorobenzyl)-9-hydroxy-7-(morpholin-3-ylmethyl)-3,4-dihydro-2H-pyrazino[1,2-c]pyrimidine-1,6,8(7H)-trione mono TFA salt (50 mg, 0.096 mmol, from Example 17) in DMF (1 mL) was added 1-(3-dimethylaminopropyl)-3-ethylcarbodiimide hydrochloride (28 mg, 0.145 mmol), 1-hydroxybenzotriazole hydrate (22 mg, 0.145 mmol), triethylamine (30 μL, 0.212 mmol), and (dimethylamino)(oxo)acetic acid (22 mg, 0.12 mmol). The reaction was stirred overnight at room temperature and equal amount of the reagents were added to the flask in the morning. After two hours the reaction was purified by prep HPLC on a C18 stationary phase with a water/acetonitrile/TFA gradient. The title compound as obtained as a white solid after lyophilization from dioxane. $^1$H NMR (400 MHz, $d_6$ DMSO) Mixture of rotamers, approximately 1:1. δ 11.8 (2bs, 1H), 7.40 (m, 2H), 7.21 (m, 2H), 4.61-4.77 (m, 4H), 4.05 (m, 0.5H), 3.78-3.99 (m, 5H), 3.67 (m, 0.5H), 3.55-3.61 (m, 3H), 3.31-3.43 (m, 1.5H), 3.08 (m, 0.5H), 2.84, 2.81 (2s, 3H), and 2.76, 2.75 (2s, 3H). HRMS (FT-ICR) $C_{23}H_{26}FN_5O_7$+H=504.1873; calculated 504.1889.

EXAMPLES 19-46

The compounds in the following table were prepared in accordance with the procedure set forth in Example 1, Step 7, using the appropriate amine.

| Example | Compound | Data |
|---|---|---|
| 19 | 7-cyclopentyl-2-(4-fluorobenzyl)-9-hydroxy-3,4-dihydro-2H-pyrazino[1,2-c]pyrimidine-1,6,8(7H)-trione | HRMS ES (M + 1) calc'd for C19H21FN3O4; 374.1511; found 374.1515. |
| 20 | 2-(4-fluorobenzyl)-9-hydroxy-7-(trans-4-hydroxycyclohexyl)-3,4-dihydro-2H-pyrazino[1,2-c]pyrimidine-1,6,8(7H)-trione | HRMS ES (M + 1) calc'd for C20H23FN3O5; 404.1616; found 404.1621. |

| Example | Compound | Data |
| --- | --- | --- |
| 21 | 7-(2,3-dihydro-1H-inden-2-yl)-2-(4-fluorobenzyl)-9-hydroxy-3,4-dihydro-2H-pyrazino[1,2-c]pyrimidine-1,6,8(7H)-trione | HRMS ES (M + 1) calc'd for C23H21FN3O4; 422.1511; found 422.1504. |
| 22 | 7-(4-tert-butylcyclohexyl)-2-(4-fluorobenzyl)-9-hydroxy-3,4-dihydro-2H-pyrazino[1,2-c]pyrimidine-1,6,8(7H)-trione | HRMS ES (M + 1) calc'd for C24H31FN3O4; 444.2293; found 444.2309. |
| 23 | 7-(2,2-dimethyltetrahydro-2H-pyran-4-yl)-2-(4-fluorobenzyl)-9-hydroxy-3,4-dihydro-2H-pyrazino[1,2-c]pyrimidine-1,6,8(7H)-trione | HRMS ES (M + 1) calc'd for C21H25FN3O5; 418.1773; found 418.1782. |
| 24 | 2-(4-fluorobenzyl)-9-hydroxy-7-(4-methoxyphenyl)-3,4-dihydro-2H-pyrazino[1,2-c]pyrimidine-1,6,8(7H)-trione | HRMS ES (M + 1) calc'd for C21H19FN3O5; 412.1303; found 412.1303. |
| 25 | 2-(4-fluorobenzyl)-9-hydroxy-7-(6-methoxypyridin-3-yl)-3,4-dihydro-2H-pyrazino[1,2-c]pyrimidine-1,6,8(7H)-trione | HRMS ES (M + 1) calc'd for C20H18FN4O5; 413.1256; found 413.1246. |

-continued

| Example | Compound | Data |
|---|---|---|
| 26 | 7-azepan-1-yl-2-(4-fluorobenzyl)-9-hydroxy-3,4-dihydro-2H-pyrazino[1,2-c]pyrimidine-1,6,8(7H)-trione | HRMS ES (M + 1) calc'd for C20H24FN4O4; 403.1776; found 403.1771. |
| 27 | 7-(1,4-dioxan-2-ylmethyl)-2-(4-fluorobenzyl)-9-hydroxy-3,4-dihydro-2H-pyrazino[1,2-c]pyrimidine-1,6,8(7H)-trione | HRMS ES (M + 1) calc'd for C19H21FN3O6; 406.1409; found 406.1404. |
| 28 | 2-(4-fluorobenzyl)-9-hydroxy-7-(isoquinolin-1-ylmethyl)-3,4-dihydro-2H-pyrazino[1,2-c]pyrimidine-1,6,8(7H)-trione | HRMS ES (M + 1) calc'd for C24H20FN4O4; 447.1463; found 447.1463. |
| 29 | 2-(4-fluorobenzyl)-9-hydroxy-7-(1,3-thiazol-4-ylmethyl)-3,4-dihydro-2H-pyrazino[1,2-c]pyrimidine-1,6,8(7H)-trione | HRMS ES (M + 1) calc'd for C18H16FN4O4S; 403.0871; found 403.0858. |
| 30 | 2-(4-fluorobenzyl)-9-hydroxy-7-[2-(thien-2-yl)ethyl]-3,4-dihydro-2H-pyrazino[1,2-c]pyrimidine-1,6,8(7H)-trione | HRMS ES (M + 1) calc'd for C20H19FN3O4S; 416.1075; found 416.1071. |

-continued

| Example | Compound | Data |
|---|---|---|
| 31 | 2-(4-fluorobenzyl)-9-hydroxy-7-(2-imidazo[1,2-a]pyridin-2-ylethyl)-3,4-dihydro-2H-pyrazino[1,2-c]pyrimidine-1,6,8(7H)-trione | HRMS ES (M + 1) calc'd for C23H21FN5O4; 450.1572; found 450.1559. |
| 32 | 2-(4-fluorobenzyl)-9-hydroxy-7-(2,2,2-trifluoroethyl)-3,4-dihydro-2H-pyrazino[1,2-c]pyrimidine-1,6,8(7H)-trione | HRMS ES (M + 1) calc'd for C16H14F4N3O4; 388.0915; found 388.092. |
| 33 | tert-butyl 2-[2-(4-fluorobenzyl)-9-hydroxy-1,6,8-trioxo-1,3,4,8-tetrahydro-2H-pyrazino[1,2-c]pyrimidin-7(6H)-yl]-2-methylpropanoate | HRMS ES (M + Na) calc'd for C22H26FN3O6Na; 470.1698; found 470.1721. |
| 34 | 7-[2-(ethylthio)ethyl]-2-(4-fluorobenzyl)-9-hydroxy-3,4-dihydro-2H-pyrazino[1,2-c]pyrimidine-1,6,8(7H)-trione | HRMS ES (M + 1) calc'd for C18H21FN3O4S; 394.1232; found 394.1237. |
| 35 | methyl 2-[2-(4-fluorobenzyl)-9-hydroxy-1,6,8-trioxo-1,3,4,8-tetrahydro-2H-pyrazino[1,2-c]pyrimidin-7(6H)-yl]-4-(methylthio)butanoate | HRMS ES (M + 1) calc'd for C20H23FN3O6S; 452.1286; found 452.1293. |

| Example | Compound | Data |
|---|---|---|
| 36 | 2-(4-fluorobenzyl)-9-hydroxy-7-(tetrahydro-2H-thiopyran-4-yl)-3,4-dihydro-2H-pyrazino[1,2-c]pyrimidine-1,6,8(7H)-trione 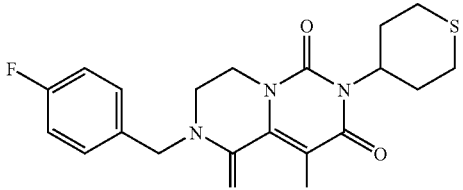 | ES MS (M + 1) = 406. |
| 37 | 7-(3,4-dihydro-2H-thiochromen-4-yl)-2-(4-fluorobenzyl)-9-hydroxy-3,4-dihydro-2H-pyrazino[1,2-c]pyrimidine-1,6,8(7H)-trione 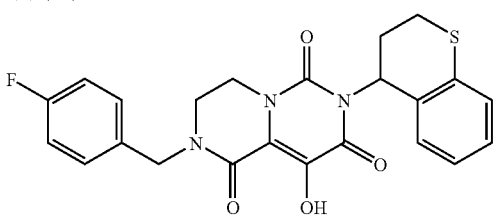 | HRMS ES (M + Na) calc'd for C23H20FN3O4SNa; 476.1051; found 476.1048. |
| 38 | 2-(4-fluorobenzyl)-9-hydroxy-7-(tetrahydro-2H-pyran-4-yl)-2H-pyrazino[1,2-c]pyrimidine-1,6,8(7H)-trione 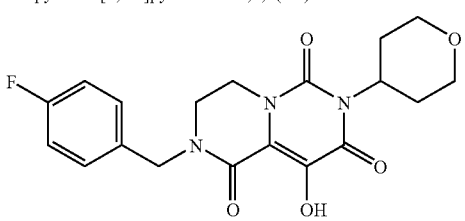 | HRMS ES (M + 1) calc'd for C19H21FN3O5, 390.1460; found 390.1458. |
| 39 | 7-dicyclopropylmethyl-2-(4-fluorobenzyl)-9-hydroxy-3,4-dihydro-2H-pyrazino[1,2-c]pyrimidine-1,6,8(7H)-trione 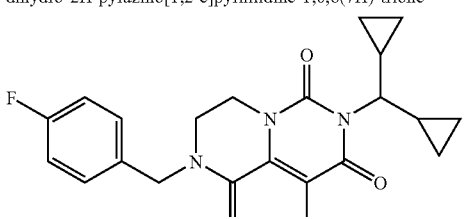 | HRMS ES (M + 1) calc'd for C21H23FN3O4, 400.1667; found 400.1667. |
| 40 | 2-(4-fluorobenzyl)-9-hydroxy-7-[4-(4-morpholinyl)phenyl]-3,4-dihydro-2H-pyrazino[1,2-c]pyrimidine-1,6,8(7H)-trione 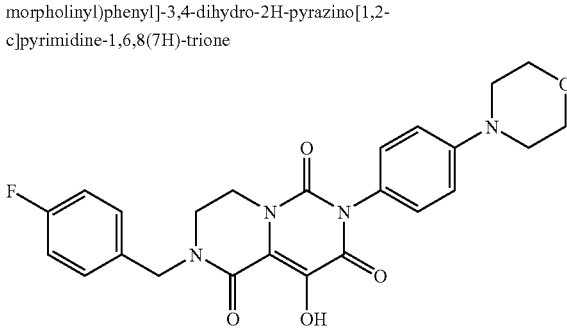 | HRMS ES (M + 1) calc'd for C24H24FN4O5, 467.1725; found 467.1704. |

-continued

| Example | Compound | Data |
| --- | --- | --- |
| 41 | 7-(1-benzyl-2-oxo-azacyclohept-3-yl)-2-(4-fluorobenzyl)-9-hydroxy-3,4-dihydro-2H-pyrazino[1,2-c]pyrimidine-1,6,8(7H)-trione | HRMS ES (M + 1) calc'd for C27H28FN4O5, 507.2038; found 507.2045. |
| 42 | 7-cyclohexyl-2-(4-fluorobenzyl)-9-hydroxy-3,4-dihydro-2H-pyrazino[1,2-c]pyrimidine-1,6,8(7H)-trione | HRMS ES (M + 1) calc'd for C20H23FN3O4, 388.1667; found 388.1676. |
| 43 | 2-(4-fluorobenzyl)-9-hydroxy-7-(trans-2-hydroxycyclohexyl)-3,4-dihydro-2H-pyrazino[1,2-c]pyrimidine-1,6,8(7H)-trione | HRMS ES (M + 1) calc'd for C20H23FN3O5, 404.1616; found 404.1621. |
| 44 | 2-(4-fluorobenzyl)-9-hydroxy-7-(3-tetrahydrofuryl)-3,4-dihydro-2H-pyrazino[1,2-c]pyrimidine-1,6,8(7H)-trione | HRMS ES(M + 1) calc'd for C18H19FN3O5, 376.1303; found 376.1308. |
| 45 | 7-cyclobutyl-2-(4-fluorobenzyl)-9-hydroxy-3,4-dihydro-2H-pyrazino[1,2-c]pyrimidine-1,6,8(7H)-trione | HRMS ES (M + 1) calc'd for C18H19FN3O4, 360.1354; found 360.1354. |

| Example | Compound | Data |
|---|---|---|
| 46 | 2-(4-fluorobenzyl)-9-hydroxy-7-(3-hydroxyadamant-1-yl)-3,4-dihydro-2H-pyrazino[1,2-c]pyrimidine-1,6,8(7H)-trione 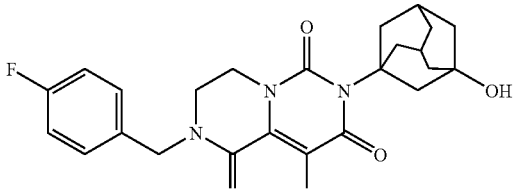 | HRMS ES (M + 1) calc'd for C24H27FN3O5, 456.1929; found 456.1939. |

EXAMPLE 47

7-[4-(1-piperidinyl)phenyl]-2-(4-fluorobenzyl)-9-hydroxy-3,4-dihydro-2H-pyrazino[1,2-c]pyrimidine-1,6,8(7H)-trione

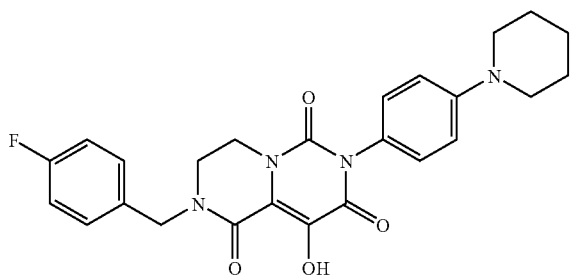

To a solution of 1-{[4-(4-fluorobenzyl)-3-oxopiperazin-1-yl]carbonyl}-3-methyl-1H-imidazol-3-ium iodide (75 mg, 0.17 mmol, from Step 6 of Example 1) in 1 mL of anhydrous DMF, under an atmosphere of nitrogen, was added triethylamine (31 µL, 0.22 mmol) and (4-piperidin-1-ylphenyl)amine (39 mg, 0.22 mmol) and the mixture was stirred for 2 h at 70° C. Dimethyl oxalate (100 µL of 6.76 M DMF solution, 0.67 mmol) and sodium hydride (20 mg, 0.83 mmol) were added, and the reaction mixture was stirred at room temperature. After 5 hours, the reaction was acidified with 3N aq. TFA (~600 µL) and purified by reverse-phase HPLC chromatography on a C18 stationary phase using a water/acetonitrile/TFA mobile phase. Lyophilization of the appropriate fractions provided the TFA salt of the title compound. $^1$H NMR (400 MHz, CDCl$_3$) δ 12.0 (s, 1H), 7.61 (d, J=9.0 Hz, 2H), 7.3 (m, 4H), 7.09 (t, J=8.6 Hz, 2H), 4.73 (s, 2H), 4.06 (t, J=5.6 Hz, 2H), 3.57 (t, J=5.6 Hz, 2H), 3.44 (t, J=5.5 Hz, 4H), 2.04 (m, 4H), 1.71 (m, 2H). HRMS ES (M+1) calc'd for C25H26FN4O4; 465.1933. found 465.1933.

EXAMPLES 48-61

Examples 48-61 were made by the same method as Example 47, wherein the title compounds were isolated as TFA salts.

| Example | Compound | Data |
|---|---|---|
| 48 | 7-(1-azabicyclo[2.2.2]oct-3-yl)-2-(4-fluorobenzyl)-9-hydroxy-3,4-dihydro-2H-pyrazino[1,2-c]pyrimidine-1,6,8(7H)-trione 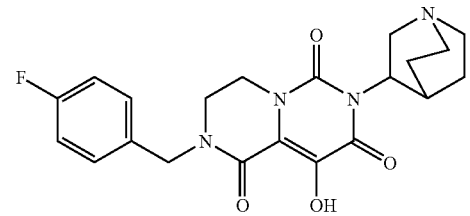 | HRMS ES (M + 1) calc'd for C21H24FN4O4; 415.1776; found 415.1773. |

-continued

| Example | Compound | Data |
| --- | --- | --- |
| 49 | 2-(4-fluorobenzyl)-9-hydroxy-7-(1,2,2,6,6-pentamethyl-4-piperidinyl)-3,4-dihydro-2H-pyrazino[1,2-c]pyrimidine-1,6,8(7H)-trione | HRMS ES (M + 1) calc'd for C24H32FN4O4, 459.2402; found 459.2407. |
| 50 | 2-(4-fluorobenzyl)-9-hydroxy-7-{1-[(2-pyrimidinyl)piperidine-3-yl]methyl}-3,4-dihydro-2H-pyrazino[1,2-c]pyrimidine-1,6,8(7H)-trione | HRMS ES (M + 1) calc'd for C24H26FN6O4; 481.1994; found 481.1996. |
| 51 | 2-(4-fluorobenzyl)-9-hydroxy-7-[1-(2-pyridyl)ethyl]-3,4-dihydro-2H-pyrazino[1,2-c]pyrimidine-1,6,8(7H)-trione | HRMS ES (M + 1) calc'd for C21H20FN4O4; 411.1463; found 411.1439. |
| 52 | 2-(4-fluorobenzyl)-9-hydroxy-7-[3-(1-imidazolyl)propyl]-3,4-dihydro-2H-pyrazino[1,2-c]pyrimidine-1,6,8(7H)-trione | HRMS ES (M + 1) calc'd for C20H21FN5O4; 414.1572; found 414.1569. |
| 53 | 7-[3-(N,N-dibutyl)propyl]-2-(4-fluorobenzyl)-9-hydroxy-3,4-dihydro-2H-pyrazino[1,2-c]pyrimidine-1,6,8(7H)-trione | HRMS ES (M + 1) calc'd for C25H36FN4O4; 475.2715; found 475.2684. |

| Example | Compound | Data |
|---|---|---|
| 54 | 2-(4-fluorobenzyl)-9-hydroxy-7-[2-(4-morpholinyl)-2-(4-pyridyl)ethyl]-3,4-dihydro-2H-pyrazino[1,2-c]pyrimidine-1,6,8(7H)-trione | HRMS ES (M + 1) calc'd for C25H27FN5O5; 496.1991; found 496.1973. |
| 55 | 2-(4-fluorobenzyl)-9-hydroxy-7-{[1-(4-methylpiperazin-4-yl)cyclohexyl]methyl}-3,4-dihydro-2H-pyrazino[1,2-c]pyrimidine-1,6,8(7H)-trione | HRMS ES (M + 1) calc'd for C26H35FN5O4; 500.2668; found 500.2661. |
| 56 | 2-(4-fluorobenzyl)-9-hydroxy-7-(2-methoxy-1-methylethyl)-3,4-dihydro-2H-pyrazino[1,2-c]pyrimidine-1,6,8(7H)-trione | HRMS ES (M + 1) calc'd for C18H21FN3O5; 378.1461; found 378.1459. |
| 57 | 7-[2,2-dimethyl-3-(4-morpholinyl)propyl]-2-(4-fluorobenzyl)-9-hydroxy-3,4-dihydro-2H-pyrazino[1,2-c]pyrimidine-1,6,8(7H)-trione | ES MS (M + 1) = 461. |
| 58 | 2-(4-fluorobenzyl)-9-hydroxy-7-[2-(4-morpholinyl)cyclohexyl]-3,4-dihydro-2H-pyrazino[1,2-c]pyrimidine-1,6,8(7H)-trione | ES MS (M + 1) = 473. |

| Example | Compound | Data |
|---|---|---|
| 59 | 2-(4-fluorobenzyl)-9-hydroxy-7-[2-(4-morpholinyl)pyrid-5-yl]-3,4-dihydro-2H-pyrazino[1,2-c]pyrimidine-1,6,8(7H)-trione | HRMS ES (M + 1) calc'd for C23H23FN5O5, 468.1678; found 468.1664. |
| 60 | 2-(4-fluorobenzyl)-9-hydroxy-7-(cis-2-hydroxycyclohexyl)-3,4-dihydro-2H-pyrazino[1,2-c]pyrimidine-1,6,8(7H)-trione | HRMS ES (M + 1) calc'd for C20H23FN3O5, 404.1616; found 404.1617. |
| 61 | 7-(1-azabicyclo[4.4.0]dec-5-ylmethyl)-2-(4-fluorobenzyl)-9-hydroxy-3,4-dihydro-2H-pyrazino[1,2-c]pyrimidine-1,6,8(7H)-trione | HRMS ES (M + 1) calc'd for C24H30FN4O4, 457.2246; found 457.2231. |

EXAMPLE 62

7-(1,1-dioxidotetrahydro-2H-thiopyran-4-yl)-2-(4-fluorobenzyl)-9-hydroxy-3,4-dihydro-2H-pyrazino[1,2-c]pyrimidine-1,6,8(7H)-trione

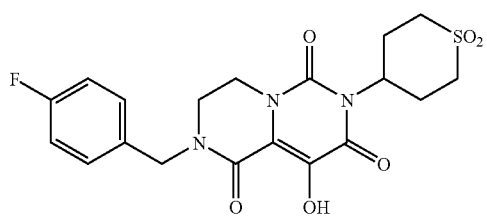

To a solution of 2-(4-fluorobenzyl)-9-hydroxy-7-tetrahydro-2H-thiopyran-4-yl-3,4-dihydro-2H-pyrazino[1,2-c]pyrimidine-1,6,8(7H)-trione (30 mg, 0.074 mmol, Example 36). in dichloromethane (2 mL) was added 3-Chloroperoxybenzoic acid (38 mg, 0.165 mmol). The reaction was stirred at room temperature and after one hour DMSO was added (0.2 mL). After stirring for one hour, the dichloromethane was evaporated under a stream of nitrogen and the reaction was diluted with water and aq. NaHCO$_3$. The precipitated product was collected by filtration and rinsed with water and diethyl ether. Drying under high vacuum provided the title compound. $^1$H NMR (400 MHz, CDCl$_3$) δ 11.8 (s, 1H), 7.3 (m, 2H), 7.07 (t, J=8.6 Hz, 2H), 5.07 (tt, J=12.0, 3.2 Hz, 1H), 4.69 (s, 2H), 4.00 (t, J=5.6 Hz, 2H), 3.53 (t, J=5.6 Hz, 2H), 3.35 (m, 2H), 3.16 (m, 4H), 1.95 (m, 2H).

EXAMPLE 63

7-(1,1-dioxido-3,4-dihydro-2H-thiochromen-4-yl)-2-(4-fluorobenzyl)-9-hydroxy-3,4-dihydro-2H-pyrazino[1,2-c]pyrimidine-1,6,8(7H)-trione

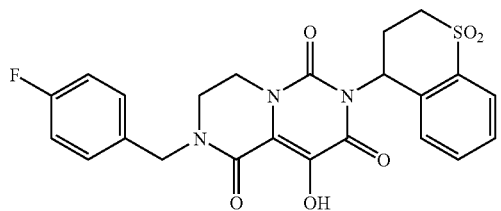

The title compound was prepared from 7-(3,4-dihydro-2H-thiochromen-4-yl)-2-(4-fluorobenzyl)-9-hydroxy-3,4-dihydro-2H-pyrazino[1,2-c]pyrimidine-1,6,8(7H)-trione (Example 37) by the same method as Example 48. HRMS ES (M+1) calc'd for C23H21FN3O6S; 486.113. found 486.1123.

EXAMPLE 64

2-(4-Fluorobenzyl)-9-hydroxy-7-isopropyl-4-[2-(methylamino)ethyl]-3,4-dihydro-2H-pyrazino[1,2-c]pyrimidine-1,6,8(7H)-trione

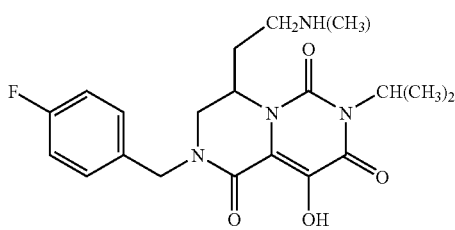

2-(4-Fluorobenzyl)-9-hydroxy-7-isopropyl-4-{2-[methoxy(methyl)amino]ethyl}-3,4-dihydro-2H-pyrazino[1,2-c]pyrimidine-1,6,8(7H)-trione (108 mg, 0.20 mmol, from Example 6) was dissolved in degassed MeOH (8 mL). The solution was degassed and purged three times with nitrogen and then treated with 10% palladium on activated carbon (25 mg) and 6 N aqueous HCl solution (10 drops). The mixture was degassed and purged with nitrogen three times more and placed under hydrogen atmosphere for 24 h. The reaction was filtered through Celite, washing with MeOH, and the filtrate was concentrated in vacuo to a dark yellow oil. Purification by reverse phase chromatography [95:5 water (+0.1% TFA)/MeCN (+0.1% TFA) to 5:95 water (+0.1% TFA)/MeCN (+0.1% TFA)] afforded the title compound as a gray foam. $^1$H NMR (500 MHz, CD$_3$OD) δ 7.45-7.43 (m, 2H), 7.16-7.12 (m, 2H), 5.19 (dt, J=7.0, 14.0 Hz, 1H), 4.94 (d, J=14.5 Hz, 1H), 4.85-4.84 (m, 1H), 4.50 (d, J=14.5 Hz, 1H), 3.84 (dd, J=4.0, 14.0 Hz, 1H), 3.43 (dd, J=1.5, 14.0 Hz, 1H), 2.92-2.78 (m, 2H), 2.64 (s, 3H), 1.96-1.88 (m, 1H), 1.77-1.70 (m, 1H), 1.47 (dd, J=4.5, 6.5 Hz, 6H). HRMS (FT/ES) M+H: calcd for (C$_{20}$H$_{26}$FN$_4$O$_4$)$^+$ 405.1933. found 405.1945.

EXAMPLE 65

N-{2-[2-(4-Fluorobenzyl)-9-hydroxy-7-isopropyl-1,6,8-trioxo-1,3,4,6,7,8-hexahydro-2H-pyrzino[1,2-c]pyrimidine-4-yl]ethyl}-N-methylacetamide

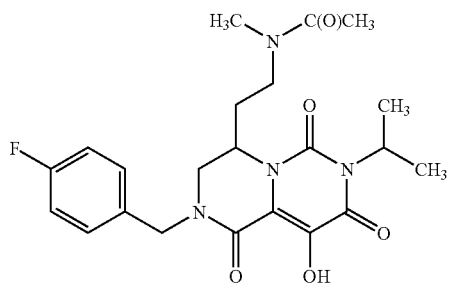

Step 1: 4-{2-[Acetyl(methyl)amino]ethyl}-2-(4-fluorobenzyl)-7-isopropyl-1,6,8-trioxo-1,3,4,6,7,8-hexahydro-2H-pyrazino[1,2-c]pyrimidine-9-yl acetate 2-(4-Fluorobenzyl)-9-hydroxy-7-isopropyl-4-[2-(methylamino)ethyl]-3,4-dihydro-2H-pyrazino[1,2-c]pyrimidine-1,6,8(7H)-trione (34 mg, 0.066 mmol, from Example 50) was suspended in CH$_2$Cl$_2$ at 0° C. and treated with Hünig's base (350 μL, 2.01 mmol), acetyl chloride (100 μL, 1.41 mmol), and 4-dimethylaminopyridine (2.0 mg, 0.013 mmol). The mixture was stirred under inert atmosphere for 20 min. Purification by reverse phase chromatography [95:5 water (+0.1% TFA)/MeCN (+0.1% TFA) to 5:95 water (+0.1% TFA)/MeCN (+0.1% TFA)] afforded the title compound as an orange oil. $^1$H NMR (400 MHz, CDCl$_3$) δ 7.39-7.36 (m, 2H), 7.09-7.03 (m, 2H), 5.18-4.98 (m, 2H), 4.44-4.32 (m, 2H), 3.83-3.35 (m, 6H), 3.00 (d, J=7.2 Hz, 3H), 2.74-2.37 (m, 2H), 2.13 (d, J=4.0 Hz, 3H), 1.76-1.73 (m, 1H), 1.47-1.44 (m, 6H).

Step 2: N-{2-[2-(4-Fluorobenzyl)-9-hydroxy-7-isopropyl-1,6,8-trioxo-1,3,4,6,7,8-hexahydro-2H-pyrazino[1,2-c]pyrimidine-4-yl]ethyl}-N-methylacetamide To a stirred solution of 4-{2-[acetyl(methyl)amino]ethyl}-2-(4-fluorobenzyl)-7-isopropyl-1,6,8-trioxo-1,3,4,6,7,8-hexahydro-2H-pyrazino[1,2-c]pyrimidine-9-yl acetate (28 mg, 0.057 mmol) in MeOH (2 mL) at ambient temperature under inert atmosphere was added potassium carbonate (48 mg, 0.344 mmol). After 1.5 h, the solvent was removed in vacuo and the residue treated with 1 N aqueous HCl solution and MeOH. The solvent was again removed in vacuo and the residue suspended in CH$_2$Cl$_2$. The mixture was filtered through a cotton plug, and the filtrate was concentrated in vacuo to give an orange oil. Purification by reverse phase chromatography [95:5 water (+0.1% TFA)/MeCN (+0.1% TFA) to 5:95 water (+0.1% TFA)/MeCN (+0.1% TFA)] afforded the title compound as an off-white solid. $^1$H NMR (400 MHz, CDCl$_3$) δ 11.76 (br s, 1H), 7.39-7.36 (m, 2H), 7.09-7.05 (m, 2H), 5.16 (dt, J=6.8, 13.6 Hz, 1H), 4.97 (d, J=14.0 Hz, 1H), 4.43 (d, J=11.2 Hz, 1H), 4.35 (d, J=14.4 Hz, 1H), 3.84 (br s, 1H), 1.77-1.70 (m, 1H), 1.46 (dd, J=1.6, 6.8 Hz, 6H). HRMS (FT/ES) M+H: calcd for (C$_{22}$H$_{27}$FN$_4$O$_5$)$^+$ 447.2038. found 447.2031.

EXAMPLE 66

4-{2-[Benzyl(methyl)amino]ethyl}-2-(4-fluorobenzyl)-9-hydroxy-7-isopropyl-3,4-dihydro-2H-pyrazino[1,2-c]pyrimidine-1,6,8(7H)-trione

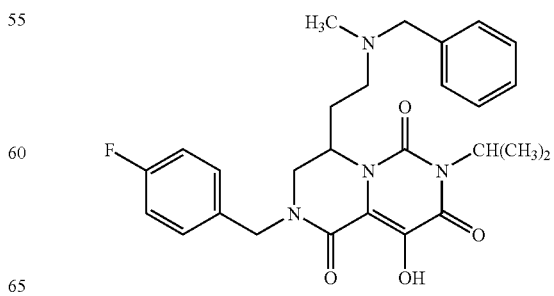

Step 1: tert-Butyl {4-[benzyl(methyl)amino]-2-oxobutyl}(4-fluorobenzyl)carbamate The title compound was prepared from $N^2$-tert-Butyloxycarbonyl-$N^2$-(4-fluorobenzyl)-$N^1$-methoxy-$N^1$-methylglycinamide (1.13 g, 3.47 mmol, from Example 6, Step 4) according to the procedure described in Example 72, Step 1 with N-methylbenzylamine (0.546 g, 4.51 mmol) in place of N-methylpiperazine. The crude product was carried directly into the next step. $^1$H NMR (400 MHz, CDCl$_3$): δ 7.33-7.14 (br m, 7 H), 7.01 (m, 2 H), 4.45 and 4.51 (s, rotamers, 2 H), 3.97 and 3.83 (s, rotamers, 2 H), 3.45 (s, 2 H), 2.72-2.65 (m, 2 H), 2.57-2.50 (m, 1 H), 2.48-2.14 (m, 1 H), 2.04 (s, 3 H), 1.46 and 1.43 (s, rotamers, 9 H). ES MS (M+1)=415.5.

Step 2: Methyl-N-(3-[benzyl(methyl)amino]-1-{[tert-butoxycarbonyl)(4-fluorobenzyl)amino]methyl}propyl)glycinate The title compound was prepared from tert-butyl {4-[benzyl(methyl)amino]-2-oxobutyl}(4-fluorobenzyl)carbamate (1.50 g, 3.62 mmol) and glycine methyl ester hydrochloride (1.18 g, 9.42 mmol) essentially according to the procedure described in Example 6, Step 6. The crude product was obtained as a yellow oil which was purified by silica gel chromatography (40 g RediSep column, 40 mL/min, gradient elution with EtOAc for 4 min, then with 0-5% MeOH-EtOAc over 12 min, then with 5-10% MeOH-EtOAc over 5 main) to afford the title compound as a light yellow oil which was used directly in the next step. ES MS (M+1)=488.6.

Step 3: 5-{2-[benzyl(methyl)amino]ethyl}-1-(4-fluorobenzyl)piperazine-2-one

The title compound was prepared from methyl-N-(3-[benzyl(methyl)amino]-1-{[tert-butoxycarbonyl)(4-fluorobenzyl)amino]-methyl}propyl)glycinate (1.54 g, 3.16 mmol) essentially according to the procedure described in Example 6, Step 7. The compound was isolated as an orange oil. $^1$H NMR (400 MHz, CDCl$_3$): δ 7.35-7.17 (br m, 7 H), 7.03-6.98 (m, 2 H), 4.57 (d, J=14.8 Hz, 1 H), 4.46 (d, J=14.4 Hz, 1 H), 3.63 (d, J=16.8 Hz, 1 H), 3.60-3.47 (br m, 2 H), 3.37 (d, J=13.2 Hz, 1 H), 3.00-2.86 (br m, 3 H), 2.54-2.44 (m, 1 H), 2.39-2.32 (m, 1 H), 2.23 (s, 3 H), 1.64-1.45 (br m, 2 H). ES MS (M+1)=356.4.

Step 4: 2-{2-[Benzyl(methyl)amino]ethyl}-4-(4-fluorobenzyl)-N-isopropyl-5-oxopiperazine-1-carboxamide The title compound was prepared from 5-{2-[benzyl(methyl)amino]-ethyl}-1-(4-fluorobenzyl)piperazine-2-one (1.15 g, 3.23 mmol) and isopropyl isocyanate (0.412 g, 4.84 mmol) essentially according to the procedure described in Example 6, Step 8. The crude product was purified by silica gel chromatography (120 g RediSep column, 85 mL/min, gradient elution with EtOAc for 4 min, then with 0-10% MeOH-EtOAc over 15 min, then with 10% MeOH-EtOAc for 11 min) to afford the title compound as a viscous, light orange oil. $^1$H NMR (400 MHz, CDCl3): δ 7.34-7.19 (br m, 7 H), 7.03-6.98 (m, 2 H), 5.59 (m, 1 H), 4.75 (d, J=11.6 Hz, 1 H), 4.58 (d, J=14.8 Hz, 1 H), 4.28 (d, J=11.6 Hz, 1 H), 4.18 (m, 1 H), 4.12 (d, J=6.0 Hz, 1 H), 3.93-3.87 (m, 1 H), 3.70 (d, J=14.8 Hz, 1 H), 3.54 (d, J=10.4 Hz, 1 H), 3.49-3.46 (br m, 1 H), 3.24 (d, J=10.4 Hz, 1 H), 2.83 (dd, J=1.2, 10.0 Hz, 1 H), 2.34-2.29 (m, 1 H), 2.18-2.14 (m, 4 H), 1.71-1.65 (m, 1 H), 1.47-1.42 (m, 1 H), 1.08 and 1.05 (d, J=5.2 Hz, rotamers, 6 H). ES MS (M+1)=441.6.

Step 5: 4-{2-[Benzyl(methyl)amino]ethyl}-2-(4-fluorobenzyl)-9-hydroxy-7-isopropyl-3,4-dihydro-2H-pyrazino[1,2-c]pyrimidine-1,6,8(7H)-trione The title compound was prepared from 2-{2-[benzyl(methyl)amino]-ethyl}-4-(4-fluorobenzyl)-N-isopropyl-5-oxopiperazine-1-carboxamide (950 mg, 2.16 mmol) essentially according to the procedure (including purification) described in Example 6, Step 9 and was isolated as a light yellow foam. $^1$H NMR (400 MHz, CD$_3$OD) δ 7.50-7.45 (m, 7 H), 7.14 (app t, J=8.4 Hz, 2 H), 5.20-5.13 (m, 1 H), 4.90-4.75 (br m, 2 H, overlapping with solvent), 4.56 (m, 1 H), 4.27 (m, 2 H), 3.83 (dd, J=3.6, 10.0 Hz, 1 H), 3.50-3.42 (m, 1 H), 3.21-2.95 (br m, 2 H), 2.72 (s, 3 H), 2.03-1.86 (br m, 2 H), 1.46 (d, J=6.8 Hz, 6 H). HRMS (FT/ES) M+H: calcd for $(C_{29}H_{33}FN_4O_6)^+$ 495.2402. found 495.2441.

EXAMPLE 67

N-{2-[2-(4-Fluorobenzyl)-9-hydroxy-7-isopropyl-1,6,8-trioxo-1,3,4,6,7,8-hexahydro-2H-pyrazino[1,2-c]pyrimidine-4-yl]ethyl}-N'-isopropyl-N-methylthiourea

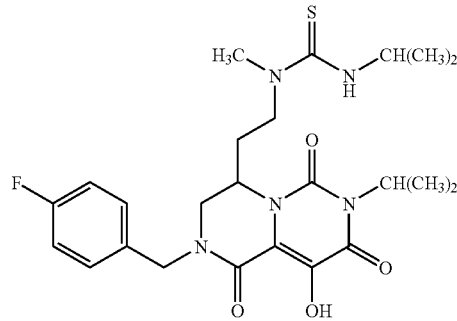

Step 1: 4-{2-[Benzyl(methyl)amino]ethyl}-2-(4-fluorobenzyl)-7-isopropyl-1,6,8-trioxo-1,3,4,6,7,8-hexahydro-2H-pyrazino[1,2-c]pyrimidin-9-yl acetate Triethylamine (370 µL, 2.64 mmol) and DMAP (21 mg, 0.18 mmol) were added to a stirred solution of 4-{2-[benzyl(methyl)amino]ethyl}-2-(4-fluorobenzyl)-9-hydroxy-7-isopropyl-3,4-dihydro-2H-pyrazino[1,2-c]pyrimidine-1,6,8(7H)-trione trifluoroacetate (from Example 52, 535 mg, 0.88 mmol) in anhydrous CH$_2$Cl$_2$ (10 mL) at 0 C. Acetyl chloride (94 µL, 1.32 mmol) was added and the mixture was then stirred at room temperature for 20 min. The solvent was removed in vacuo and the residue partitioned between EtOAc and saturated aqueous NaHCO$_3$. The layers were separated and the aqueous layer extracted with EtOAc. The combined organic layers were washed successively with water and brine, dried (Na$_2$SO$_4$), filtered and concentrated in vacuo to give the title compound as an orange solid which was carried directly into the hydrogenation step. ES MS (M+1)=537.6.

Step 2: 2-(4-Fluorobenzyl)-7-isopropyl-4-[2-(methylamino)ethyl]-1,6,8-trioxo-1,3,4,6,7,8-hexahydro-2H-pyrazino[1,2-c]pyrimidin-9-yl acetate 4-{2-[Benzyl(methyl)amino]ethyl}-2-(4-fluorobenzyl)-7-isopropyl-1,6,8-trioxo-1,3,4,6,7,8-hexahydro-2H-pyrazino

[1,2-c]pyrimidin-9-yl acetate (456 mg, 0.85 mmol) was suspended in degassed MeOH (10 mL). Aqueous HCl (6 M) was added dropwise until all the solids dissolved. The resulting stirred solution was degassed and purged with nitrogen three times. Palladium on carbon (10%, 131 mg) was added and the mixture was again degassed and purged with nitrogen (×3) and was then placed under hydrogen atmosphere (balloon) and stirred overnight at room temperature. The mixture was filtered through Celite, washing the filter cake well with MeOH. The filtrate was concentrated in vacuo and the residual oil triturated with diethyl ether to afford the hydrochloride salt of the title compound as a bright yellow solid. ES MS (M+1)=447.5.

Step 3: N-{2-[2-(4-Fluorobenzyl)-9-hydroxy-7-isopropyl-1,6,8-trioxo-1,3,4,6,7,8-hexahydro-2H-pyrazino[1,2-c]pyrimidine-4-yl]ethyl}-N'-isopropyl-N-methylthiourea To a suspension of 2-(4-fluorobenzyl)-7-isopropyl-4-[2-(methylamino)ethyl]-1,6,8-trioxo-1,3,4,6,7,8-hexahydro-2H-pyrazino[1,2-c]pyrimidin-9-yl acetate hydrochloride (37 mg, 0.077 mmol) in $CH_2Cl_2$ (830 μL) were added isopropyl isothiocyanate (15 μL) and triethylamine (36 μL) in $CH_2Cl_2$ (214 μL). The reaction was stirred at ambient temperature for 18 h. The resulting mixture was diluted with EtOAc and filtered, washing with excess EtOAc. The filtrate was concentrated at 40° C. under a steady stream of nitrogen to afford a sticky solid which was dissolved in MeOH (1.5 mL) and treated with $K_2CO_3$ (64 mg, 0.46 mmol). The reaction was stirred at ambient temperature for 18 h. Following addition of trifluoroacetic acid, the mixture was filtered through a cotton plug, purified by reverse phase chromatography [95:5 water (+0.1% TFA)/MeCN (+0.1% TFA) to 5:95 water (+0.1% TFA)/MeCN (+0.1% TFA)], and azeotroped with $CH_2Cl_2$ to afford the title compound as an off-white foam. $^1$H NMR (500 MHz, CDCl$_3$) δ 11.80 (br s, 1H), 7.40-7.37 (m, 2H), 7.08-7.05 (m, 2H), 4.69 (d, J=14.5 Hz, 1H), 4.60-4.52 (m, 2H), 4.32-4.26 (m, 1H), 4.09 (d, J=14.0 Hz, 1H), 3.57 (dd, J=3.5, 14.0 Hz, 1H), 3.51-3.40 (m, 2H), 3.01 (s, 3H), 1.71 (br s, 1H), 1.46 (d, J=7.0 Hz, 6H), 1.26 (dd, J=3.5, 6.5 Hz, 6H). HRMS (FT/ES) M+H: calcd for $(C_{24}H_{32}FN_5O_4S)^+$ 506.2232. found 506.2247.

EXAMPLE 68

N-{2-[2-(4-fluorobenzyl)-9-hydroxy-7-isopropyl-1,6,8-trioxo-1,3,4,6,7,8-hexahydro-2H-pyrazino[1,2-c]pyrimidin-4-yl]ethyl}-N'-isopropyl-N-methylurea

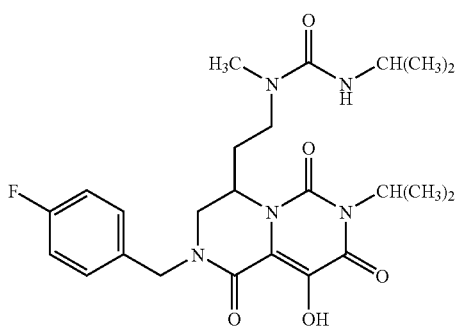

The title compound was prepared essentially according to the procedure described in Example 53, Step 3, except that isopropyl isocyanate was used in place of isopropyl isothiocyanate. $^1$H NMR (500 MHz, CDCl$_3$) δ 11.78 (br s, 1H), 7.39-7.36 (m, 2H), 7.08-7.04 (m, 2H), 5.17 (t, J=7.0 Hz, 1H), 4.92 (d, J=14.0 Hz, 1H), 4.51 (d, J=10.5, 1H), 4.41 (d, J=14.5 Hz, 1H), 3.91-3.84 (m, 2H), 3.62 (dd, J=3.5, 14.0 Hz, 1H), 3.50-3.43 (m, 2H), 2.82 (s, 3H), 2.70-2.66 (m, 1H), 2.15 (br s, 1H), 1.70 (br s, 1H), 1.46 (d, J=7.0 Hz, 6H), 1.16 (d, J=7.0 Hz, 6H). HRMS (FT/ES) M+H: calcd for $(C_{24}H_{32}FN_5O_5)^+$ 490.2460. found 490.2493

EXAMPLE 69

N-{2-[2-(4-Fluorobenzyl)-9-hydroxy-7-isopropyl-1,6,8-trioxo-1,3,4,6,7,8-hexahydro-2H-pyrazino[1,2-c]pyrimidine-4-yl]ethyl}-N-methylbenzamide

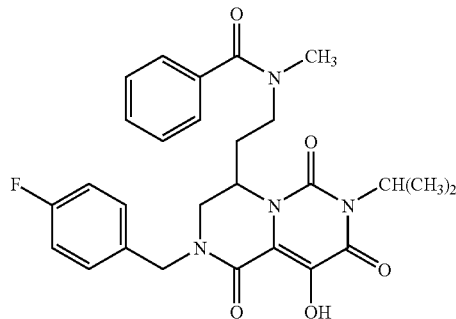

2-(4-Fluorobenzyl)-7-isopropyl-4-[2-(methylamino)ethyl]-1,6,8-trioxo-1,3,4,6,7,8-hexahydro-2H-pyrazino[1,2-c]pyrimidin-9-yl acetate hydrochloride (from Example 67, Step 2, 37 mg, 0.077 mmol) was suspended in $CH_2Cl_2$ and treated with benzoyl chloride (15 μL, 0.13 mmol), triethylamine (36 μL, 0.26 mmol) in $CH_2Cl_2$ (214 μL), and 4-dimethylaminopyridine (2.0 mg, 0.015 mmol) in $CH_2Cl_2$ (50 μL). The solution was stirred at ambient temperature for 18 h. The resulting material was suspended in EtOAc and filtered, washing with excess EtOAc. The filtrate was concentrated at 40° C. under a steady stream of nitrogen to yield a sticky solid which was dissolved in MeOH and treated with sodium methoxide in MeOH (25 wt %, 1.5 mL). The reaction was stirred for 30 min at ambient temperature and was then treated with aqueous HCl (1 M) and trifluoroacetic acid. The mixture was concentrated at 40° C. under a steady stream of nitrogen. The resulting residue was taken up in $CH_2Cl_2$, filtered, and concentrated. Purification of the remaining residue (dissolved in MeOH) by reverse phase chromatography [95:5 water (+0.1% TFA)/MeCN (+0.1% TFA) to 5:95 water (+0.1% TFA)/MeCN (+0.1% TFA)] afforded the title compound as a white solid. $^1$H NMR (500 MHz, CDCl$_3$) δ 11.77 (br s, 1H), 7.47-7.30 (m, 5H), 7.29-7.22 (m, 3H), 4.41 (d, J=14.0 Hz, 1H), 3.93 (d, J=14.0 Hz, 1H), 3.77-3.73 (m, 1H), 3.65 (d, J=11.0 Hz, 1H), 2.98 (s, 3H), 2.77 (d, J=13.0 Hz, 1H), 1.87 (br s, 1H), 1.48 (d, J=6.0 Hz, 6H). HRMS (FT/ES) M+H: calcd for $(C_{27}H_{29}FN_4O_5)^+$ 509.2195. found 509.2214.

EXAMPLE 70

4-[(Benzyloxy)methyl]-2-(4-fluorobenzyl)-9-hydroxy-7-isopropyl-3,4-dihydro-2H-pyrazino[1,2-c]pyrimidine-1,6,8(7H)-trione

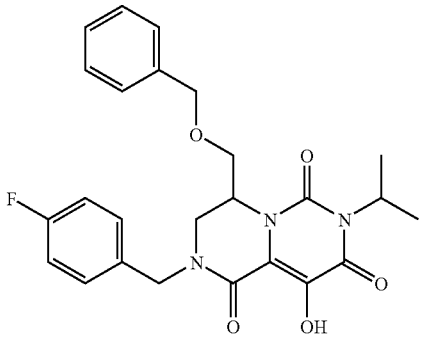

Step 1: O-Benzyl-$N^1$-methoxy-$N^1$-methyl-$N^2$-(tert-butoxycarbonyl)serinamide To a solution of O-benzyl-N-(tert-butoxycarbonyl)serine (5.9 g, 20.0 mmol) in $CH_2Cl_2$ (20 mL) was added N,O-dimethylhydroxylamine hydrochloride (1.95 g, 20.0 mmol) followed by N-methylmorpholine (2.20 mL, 19.98 mmol). The mixture was cooled to 0° C. and treated with a 1 M solution of N,N-dicyclohexylcarbodiimide in $CH_2Cl_2$ (20.0 mL, 20.0 mmol). The mixture was allowed to warm to ambient temperature while stirring under inert atmosphere for 18 h. The mixture was filtered, washing the solid residue with excess $CH_2Cl_2$, and the filtrate was concentrated in vacuo. The resulting oil was suspended in EtOAc, stirred for 20 min, and filtered once more, washing with EtOAc. The filtrate was concentrated to an orange oil which was purified by silica gel chromatography (20% to 60% EtOAc/hexanes) to afford the title compound as a colorless oil. $^1$H NMR (500 MHz, $CDCl_3$) δ 7.35-7.25 (m, 5H), 5.44 (d, J=8.4 Hz, 1H), 4.88 (d, J=3.2 Hz, 1H), 4.53 (dd, J=12.4, 28.8 Hz, 2H), 3.71 (s, 3H), 3.69-3.64 (m, 2H), 3.21 (s, 3H), 1.44 (s, 9H). ES MS (M+1−100, for loss of BOC group)=239.2.

Step 2: tert-Butyl 2-(benzyloxy)-1-formylethylcarbamate

A cold (10° C.) solution of O-benzyl-$N^1$-methoxy-$N^1$-methyl-$N^2$-(tert-butoxycarbonyl)serinamide (6.27 g, 18.5 mmol) in diethyl ether (312 mL) was treated in portions with LAH (780 mg, 20.6 mmol). The reaction was stirred under inert atmosphere for 30 min and quenched at 0° C. by the addition of a solution of $KHSO_4$ (16 g) in water (75 mL). The mixture was diluted with 1 M aqueous HCl (60 mL), and the organic layer was washed with brine, dried over $MgSO_4$ and concentrated in vacuo to a yellow oil. Purification by silica gel chromatography (10% to 50% EtOAc/hexanes) afforded the title compound as a colorless oil. $^1$H NMR (500 MHz, $CDCl_3$) δ 9.64 (s, 1H), 7.38-7.26 (m, 5H), 5.42 (d, J=5.0 Hz, 1H), 4.51 (dd, J=12.0, 19.5 Hz, 2H), 4.32 (d, J=4.01-3.99 (m, 1H), 3.73-3.70 (m, 1H), 1.46 (s, 9H). ES MS (M+1−100, for loss of BOC group)=180.1.

Step 3: tert-Butyl 2-(benzyloxy)-1-{[(4-fluorobenzyl)amino]methyl}-ethylcarbamate To a stirred solution of tert-butyl 2-(benzyloxy)-1-formylethylcarbamate (3.29 g, 11.8 mmol) in anhydrous THF (12 mL) was added 4-fluorobenzylamine (2.03 mL, 17.7 mmol). After 10 min, sodium triacetoxyborohydride (3.99 g, 18.8 mmol) was added, and the reaction was stirred at ambient temperature under inert atmosphere for 30 min. Saturated aqueous $NaHCO_3$ solution was added and the mixture stirred until gas evolution ceased. The aqueous layer was extracted with EtOAc, saturated with NaCl and again extracted with EtOAc. The combined organic extracts were washed with brine, dried over $Na_2SO_4$ and concentrated in vacuo. The resulting cloudy yellow oil was purified by silica gel chromatography (EtOAc to 10% MeOH/EtOAc) to afford the title compound as a pale yellow oil. $^1$H NMR (500 MHz, $CDCl_3$) δ 7.37-7.23 (m, 7H), 7.03-6.96 (m, 2H), 5.04 (br s, 1H), 4.49 (dd, J=11.5, 18.0 Hz, 2H), 3.86 (br s, 1H), 3.76-3.70 (m, 2H), 3.60 (dd, J=3.0, 9.0 Hz, 1H), 3.53 (d, J=4.5 Hz, 1H), 2.83-2.80 (m, 1H), 2.76-2.72 (m, 1H), 1.44 (s, 9H). ES MS (M+1)=389.5.

Step 4: tert-Butyl 2-(benzyloxy)-1-{[(bromoacetyl)(4-fluorobenzyl)amino]-methyl}ethylcarbamate Bromoacetyl bromide (588 μL, 6.75 mmol) was added slowly to a stirred solution of tert-butyl 2-(benzyloxy)-1-{[(4-fluorobenzyl)amino]-methyl}ethylcarbamate (2.39 g, 6.14 mmol) and triethylamine (941 μL, 6.75 mmol) in anhydrous THF (12 mL) at 0° C. under inert atmosphere. After stirring for 20 min, the reaction was poured into ice water and extracted twice with diethyl ether. The combined organic layers were washed twice with brine, dried over $Na_2SO_4$, and concentrated in vacuo. The resulting orange/brown oil was purified by silica gel chromatography (10% to 40% EtOAc/hexanes) to afford the title compound as a red-orange oil. $^1$H NMR (500 MHz, $CDCl_3$) δ 7.40-7.21 (m, 6H), 7.16-6.96 (m, 3H), 5.20 (d, J=8.0 Hz, 1H), 5.01 (d, J=9.0 Hz, 1H), 4.75-4.66 (m, 1H), 4.59-4.48 (m, 2H), 4.39 (d, J=15.0 Hz, 1H), 4.04-3.92 (m, 2H), 3.87-3.28 (m, 4H), 1.43 (s, 9H). ES MS (M+1−100, for loss of BOC group)=409.4.

Step 5: 5-[(Benzyloxy)methyl]-1-(4-fluorobenzyl)piperazine-2-one

To a solution of tert-butyl 2-(benzyloxy)-1-{[(bromoacetyl)(4-fluorobenzyl)amino]methyl}ethylcarbamate (2.79 g, 5.47 mmol) in $CH_2Cl_2$ (28 mL) was added trifluoroacetic acid (10 ml). The reaction was stirred at ambient temperature under inert atmosphere for 2 h and then concentrated in vacuo, azeotroping the residual oil with $CHCl_3$. The resulting residue was dissolved in $CH_2Cl_2$ (100 mL) and treated with Hünig's base (10 mL). The solution was stirred at ambient temperature under inert atmosphere for 18 h. The solvent was removed in vacuo, and the remaining residue was partitioned between EtOAc and saturated aqueous $NaHCO_3$ solution. The organic layer was washed with water and brine, dried over $Na_2SO_4$, and concentrated in vacuo. Purification by silica gel chromatography (EtOAc to 10% MeOH/EtOAc) afforded the title compound as a yellow oil. $^1$H NMR (400 MHz, $CDCl_3$) δ 7.37-7.22 (m, 7H), 7.04-6.98 (m, 2H), 4.64 (d, J=14.8 Hz, 1H), 4.49-4.44 (m, 3H), 3.63 (dd, J=17.6, 41.2 Hz, 2H), 3.47 (dd, J=4.0, 9.6 Hz, 1H), 3.40 (dd, J=6.4, 9.2 Hz, 1H), 3.22-3.16 (m, 1H), 3.10-3.06 (m, 2H), 1.71 (br s, 1H). ES MS (M+1)=329.3.

Step 6: 2-[(Benzyloxy)methyl]-4-(4-fluorobenzyl)-N-isopropyl-5-oxopiperazine-1-carboxamide The urea was prepared essentially according to the procedure described in Example 6, Step 8. The crude product was purified by silica gel chromatography (isocratic elution with EtOAc). $^1$H NMR (400 MHz, CDCl$_3$) δ 7.35-7.18 (m, 7H), 7.01-6.97 (m, 2H), 4.70 (d, J=14.4 Hz, 1H), 4.55 (d, J=7.2 Hz, 1H), 4.43-4.31 (m, 4H), 4.14 (d, J=16.8 Hz, 1H), 3.93-3.85 (m, 2H), 3.50 (dd, J=4.4, 12.8 Hz, 1H), 3.42 (dd, J=6.4, 9.2 Hz, 1H), 3.32-3.26 (m, 2H), 1.09 (dd, J=6.8, 13.6 Hz, 6H). ES MS (M+1)=414.4.

Step 7: 4-[(Benzyloxy)methyl]-2-(4-fluorobenzyl)-9-hydroxy-7-isopropyl-3,4-dihydro-2H-pyrazino[1,2-c]pyrimidine-1,6,8(7H)-trione The title compound was prepared essentially according to the procedure described in Example 6, Step 9. The crude reaction product was partitioned between EtOAc and 1 M aqueous HCl solution. Brine and NaCl were added to the mixture and the layers were separated. The aqueous layer was saturated once more with NaCl and extracted with EtOAc. The combined organic layers were dried over Na$_2$SO$_4$ and concentrated in vacuo. The resulting solids were suspended in MeOH and diethyl ether and cooled to −20° C. for 18 h. Filtration of the mixture, washing the solids with MeOH and diethyl ether, afforded the title compound as a white solid. $^1$H NMR (400 MHz, CDCl$_3$) δ 11.76 (s, 1H), 7.52-7.25 (m, 5H), 7.17-7.15 (m, 2H), 7.06-6.99 (m, 2H), 5.18 (dt, J=6.8, 13.6 Hz, 1H), 4.87-4.83 (m, 1H), 4.69 (d, J=14.4 Hz, 1H), 4.48 (d, J=14.8 Hz, 1H), 4.38 (d, J=11.6 Hz, 1H), 4.26 (d, J=11.6 Hz, 1H), 3.64 (d, J=3.2 Hz, 2H), 3.50-3.47 (m, 1H), 3.35 (t, J=8.8 Hz, 1H), 1.46 (dd, J=2.4, 6.8 Hz, 6H). HRMS (FT/APCI) M+H: calcd for $(C_{25}H_{26}FN_3O_5)^+$ 468.1929. found 468.1936

EXAMPLE 71

4-[2-(Benzyloxy)ethyl]-2-(4-fluorobenzyl)-9-hydroxy-7-isopropyl-3,4-dihydro-2H-pyrazino[1,2-c]pyrimidine-1,6,8(7H)-trione

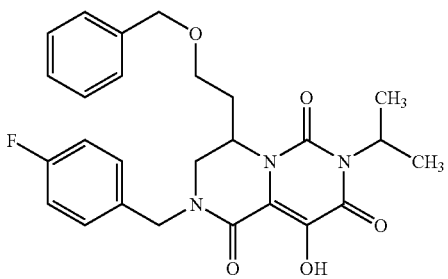

The title compound was prepared essentially according to the procedures described in Example 70, starting with O-Benzyl-N$^1$-methoxy-N$^1$-methyl-N$^2$-(tert-butoxycarbonyl)homoserinamide. The product of the final step was purified by reverse phase chromatography to afford the title compound as an off-white solid. $^1$H NMR (400 MHz, CDCl$_3$) δ 11.76 (s, 1H), 7.40-7.26 (m, 7H), 7.16-7.10 (m, 1H), 7.10-6.97 (m, 1H), 5.19 (dt, J=6.8, 13.6 Hz, 1H), 4.83 (dd, J=3.6, 5.2 Hz, 1H), 4.65 (d, J=14.0 Hz, 1H), 4.46-4.36 (m, 3H), 3.57-3.32 (m, 4H), 1.88-1.71 (m, 2H), 1.46 (d, J=7.2 Hz, 6H). HRMS (FT/APCI) M+H: calcd for $(C_{26}H_{28}FN_3O_5)^+$ 482.2086. found 482.2085.

EXAMPLE 72

7-Cyclopropyl-2-(4-fluorobenzyl)-9-hydroxy-4-[2-(4-methylpiperazin-1-yl)ethyl]-6-thioxo-3,4,6,7-tetrahydro-2H-pyrazino[1,2-c]pyrimidine-1,8-dione

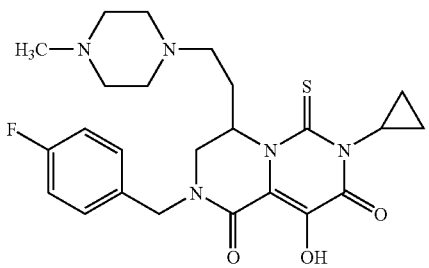

Step 1: tert-Butyl-4-fluorobenzyl[4-(4-methylpiperazin-1-yl)-2-oxobutyl]carbamate N$^2$-tert-Butyloxycarbonyl-N$^2$-(4-fluorobenzyl)-N$^1$-methoxy-N$^1$-methylglycinamide oxobutanoate (1.72 g, 5.28 mmol, from Example 6, Step 4) was azeotroped with anhydrous toluene (20 mL) and dissolved in anhydrous THF (53 mL). The solution was cooled to 0° C. and treated rapidly with vinylmagnesium bromide (866 mg, 6.60 mmol) under inert atmosphere. After stirring for 20 min at 0° C. and warming to ambient temperature over 40 min, the mixture was treated with N-methylpiperazine (585 μL, 5.28 mmol) and water (8 ml) and stirred for 20 min. The reaction was partitioned between EtOAc and brine, and the organic layer was washed twice with water, dried over Na$_2$SO$_4$, and concentrated in vacuo. The residue was azeotroped with CHCl$_3$ to afford the title compound as yellow oil. $^1$H NMR (400 MHz, CDCl$_3$) δ 7.26-7.17 (m, 3H), 7.03-7.00 (m, 1H), 4.45 (d, J=16.8 Hz, 2H), 3.93 (d, J=54.8 Hz, 2H), 2.67-2.45 (m, 12H), 2.27 (s, 3H), 1.46 (d, J=8.4 Hz, 9H). ES MS (M+1)=394.5.

Step 2: Methyl N-[1-{[(tert-butoxycarbonyl)(4-fluorobenzyl)amino]methyl}-3-(4-methylpiperazin-1-yl)propyl]glycinate The title compound was prepared from tert-butyl-4-fluorobenzyl[4-(4-methylpiperazin-1-yl)-2-oxobutyl]carbamate and glycine methyl ester hydrochloride using a procedure essentially the same as that in Example 6, Step 6. $^1$H NMR (400 MHz, CDCl$_3$) δ 7.19 (br s, 2H), 7.00 (t, J=8.4 Hz, 2H), 4.50-4.46 (m, 1H), 4.39 (d, J=15.6 Hz, 1H), 4.05 (d, J=4.8 Hz, 1H), 3.77 (s, 1H), 3.72 (s, 3H), 3.56-3.38 (m, 2H), 3.27-3.05 (m, 2H), 2.82-2.77 (m, 2H), 2.55-2.43 (m, 8H), 2.29 (s, 3H), 2.05 (s, 2H), 1.45 (d, J=13.2 Hz, 9H). ES MS (M+1)=467.4.

Step 3: 1-(4-Fluorobenzyl)-5[2-(4-methylpiperzin-1-yl)ethylpiperazin-2-one

The title compound was prepared essentially according to the procedure described in Example 6, Step 7 and was isolated as a brown oil. $^1$H NMR (400 MHz, CDCl$_3$) δ 7.25-7.23 (m, 2H), 7.04-6.99 (m, 2H), 4.63 (d, J=14.8 Hz, 1H), 4.46 (d, J=14.4 Hz, 1H), 3.62 (dd, J=17.2, 36.4 Hz, 2H), 3.09-2.97 (m, 3H), 2.63-2.36 (m, 10H), 2.29 (s, 3H), 1.63-1.44 (m, 3H). ES MS (M+1)=335.3.

Step 4: N-Cyclopropyl-4-(4-fluorobenzyl)-2-[2-(4-methylpiperazin-1-yl)ethyl]-5-oxopiperazine-1-carbothioamide To a cold (0° C.) solution of 1-(4-fluorobenzyl)-5[2-(4-methylpiperazin-1-yl)ethyl]piperazin-2-one (241 mg, 0.72 mmol) in EtOAc (4 mL) was added cyclopropyl isocyanate (70 µL, 0.76 mmol). The mixture was stirred at ambient temperature under inert atmosphere for 66 h. The resulting precipitate was filtered, washing with ether, to afford the title thiourea as a white solid. Additional product remaining in the filtrate was recovered by reverse phase chromatography [95:5 water (+0.1% TFA)/MeCN (+0.1% TFA) to 5:95 water (+0.1% TFA)/MeCN (+0.1% TFA)] to afford the trifluoroacetate salt of the urea as an off-white solid. $^1$H NMR (400 MHz, d$_6$-DMSO, free base) δ 7.90 (br s, 1H), 7.35-7.32 (m, 2H), 7.20-7.15 (m, 2H), 4.95 (br s, 1H), 4.72 (d, J=14.4 Hz, 2H), 4.29 (d, J=14.4 Hz, 1H), 3.81 (d, J=18.0 Hz, 1H), 3.45 (dd, J=3.6, 12.8 Hz, 1H), 3.32 (s, 1H), 3.11 (d, J=12.4, 1H), 2.91 (br s, 1H), 2.50 (s, 1H), 2.42-2.27 (m, 6H), 2.13 (s, 3H), 2.00-1.97 (m, 2H), 1.61-1.56 (m, 1H), 1.46 (m, 1H), 0.67 (d, J=6.8 Hz, 2H), 0.64-0.53 (m, 2H). HRMS (FT/ES) M+H: calcd for $(C_{22}H_{32}FN_5OS)^+$ 434.2385. found 434.2386.

Step 5: 7-Cyclopropyl-2-(4-fluorobenzyl)-9-hydroxy-4-[2-(4-methylpiperazin-1-yl)ethyl]-6-thioxo-3,4,6,7-tetrahydro-2H-pyrazino[1,2-c]pyrimidine-1,8-dione The title compound was prepared essentially according to the procedure described in Example 6, Step 9 and was isolated as the trifluoroacetate salt. $^1$H NMR (400 MHz, d$_6$-DMSO) δ 7.46-7.43 (m, 2H), 7.26-7.21 (m, 2H), 5.74 (d, J=4.4 Hz, 1H), 4.80 (d, J=14.4 Hz, 1H), 4.60 (d, J=14.4 Hz, 1H), 3.78 (d, J=10.4 Hz, 1H), 3.51 (d, J=14.0 Hz, 1H), 3.40-2.80 (m, 6H), 2.77 (s, 3H), 2.33-2.29 (m, 4H), 1.86-1.84 (m, 1H), 0.80-0.73 (m, 1H), 0.67-0.61 (m, 1H). HRMS (FT/ES) M+H: calcd for $(C_{24}H_{30}FN_5O_3S)^+$ 488.2126. found 488.2114.

EXAMPLE 73

4-[2-(3,4-Dihydroisoquinolin-2(1H)-yl)ethyl]-2-(4-fluorobenzyl)-9-hydroxy-7-isopropyl-3,4-dihydro-2H-pyrazino[1,2-c]pyrimidine-1,6,8(7H)-trione

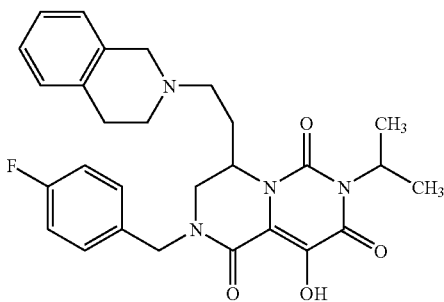

The title compound was prepared essentially according to the procedure described in Example 72, except that 1,2,3,4-tetrahydroisoquinoline was used in place of N-methylpiperazine in Step 1, and isopropyl isocyanate was used in place of cyclopropyl isothiocyanate in Step 4. The title compound was isolated as an off-white foam. $^1$H NMR (400 MHz, d$_6$-DMSO) δ 11.78 (s, 1H), 9.67 (s, 1H), 7.46-7.42 (m, 2H), 7.31-7.17 (m, 6H), 5.09-5.02 (m, 1H), 4.84-4.78 (m, 2H), 4.65-4.59 (m, 1H), 4.45 (d, J=15.2 Hz, 1H), 4.29-4.16 (m, 1H), 3.83-3.79 (m, 2H), 3.63 (s, 1H), 3.47 (d, J=13.2 Hz, 1H), 3.19-3.07 (m, 3H), 2.00 (d, J=7.2 Hz, 2H), 1.40 (d, J=6.8 Hz, 6H). HRMS (FT/ES) M+H: calcd for $(C_{28}H_{31}FN_4O_4)^+$ 507.2402. found 507.2424.

EXAMPLE 74

2-(4-fluorobenzyl)-9-hydroxy-4-[2-(1H-imidazol-1-yl)ethyl]-7-isopropyl-3,4-dihydro-2H-pyrazino[1,2-c]pyrimidine-1,6,8(7H)-trione

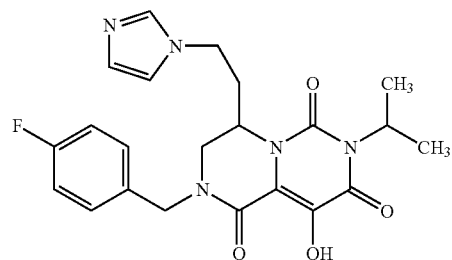

Step 1: 4-[2-(Benzyloxy)ethyl]-2-(4-fluorobenzyl)-7-isopropyl-1,6,8-trioxo-1,3,4,6,7,8-hexahydro-2H-pyrazino[1,2-c]pyrimidin-9-yl pivalate To a solution of 4-[2-(benzyloxy)ethyl]-2-(4-fluorobenzyl)-9-hydroxy-7-isopropyl-3,4-dihydro-2H-pyrazino[1,2-c]pyrimidine-1,6,8(7H)-trione (Example 9, Step 6, 1.18 g, 2.46 mmol) in anhydrous dichloromethane (20 mL) at 0° C. were added diisopropylethylamine (856 µL, 4.91 mmol), trimethylacetyl chloride (454 µL, 3.69 mmol), and N,N-dimethylaminopyridine (60 mg, 0.49 mmol). The mixture was stirred at ambient temperature under inert atmosphere for 1.5 h. Addition of methanol resulted in the precipitation of the title compound as a white solid. $^1$H NMR (CDCl$_3$, 400 MHz): δ 7.39-7.26 (m, 5 H), 7.07-7.03 (m, 2 H), 6.97-6.93 (m, 2 H), 5.18-5.12 (m, 1 H), 4.79 (m, 1 ), 4.64-4.58 (m, 1 H), 4.47-4.34 (m, 3 H), 3.66-3.54 (m, 1 H), 3.45-3.27 (m, 3 H), 1.88 (m, 1 H), 1.77-1.72 (m, 1 H), 1.46-1.44 (m, 6 H), 1.40 (s, 9 H). ES MS (M+1)=566.7.

Step 2: 2-(4-fluorobenzyl)-4-(2-hydroxyethyl)-7-isopropyl-1,6,8-trioxo-1,3,4,6,7,8-hexahydro-2H-pyrazino[1,2-c]pyrimidine-9-yl pivalate A mixture of 4-[2-(benzyloxy)ethyl]-2-(4-fluorobenzyl)-7-isopropyl-1,6,8-trioxo-1,3,4,6,7,8-hexahydro-2H-pyrazino[1,2-c]pyrimidin-9-yl pivalate (918 mg, 1.62 mmol) and 10% Pd(C) (92 mg) in ethyl acetate (32 mL) was stirred under a balloon atmosphere of hydrogen for 24 h. The reaction mixture was filtered through Celite, fresh catalyst was added and the mixture subjected to balloon hydrogenation for an additional 24 h. Analysis by LCMS showed slow conversion to the alcohol, so the mixture was again filtered through Celite and the filtrate was concentrated. The residual solid was taken up in ethanol (32 mL) with a small amount of ethyl acetate added to aid dissolution of the material. 10% Pd(C) was added and the mixture subjected to balloon hydrogenation for 96 h, with fresh catalyst being added after the first 24 h. The reaction still appeared to be progressing slowly, so the mixture was filtered through Celite and Pearlman's catalyst was added to the filtrate. Hydrogenation (balloon) was complete after 48 h (fresh Pearlman's catalyst was added after the first 24 h). Filtration through Celite and concentration afforded the title compound as a foamy white solid. $^1$H NMR (CDCl$_3$, 400 MHz): δ 7.28-7.26 (m, 2 H), 7.07-7.02 (m, 2 H), 5.21-5.14 (m, 1 H), 4.87-4.74 (m, 2 H), 4.48-4.36 (m, 1 H), 3.89-3.77 (m, 1 H), 3.49-3.25 (m, 3 H), 1.68-1.54 (m, 2H), 1.46 (d, J=6.8 MHz, 6 H), 1.40 (s, 9 H). ES MS (M+1): 476.5.

Step 3: 2-(4-fluorobenzyl)-7-isopropyl-4-{2-[(methylsulfonyl)oxy]ethyl}-1,6,8-trioxo-1,3,4,6,7,8-hexahydro-2H-pyrazino[1,2-c]pyrimidine-9-yl pivalate 2-(4-Fluorobenzyl)-4-(2-hydroxyethyl)-7-isopropyl-1,6,8-trioxo-1,3,4,6,7,8-hexahydro-2H-pyrazino[1,2-c]pyrimidine-9-yl pivalate (300 mg, 0.63 mmol) was azeotroped twice with anhydrous acetonitrile, twice with anhydrous toluene, and was then taken up in anhydrous acetonitrile (6.2 mL) under N$_2$ and the solution cooled to 0° C. To this solution was added triethylamine (0.37 mL, 2.71 mmol) and methanesulfonyl chloride (0.13 mL, 1.63 mmol). After 1 h, the resulting mixture was filtered and the filtrate was concentrated in vacuo. The residue was taken up in ethyl acetate, filtered, and the filtrate was concentrated in vacuo to afford the title compound as an orange foam, which was carried on crude. ES MS (M+H): 554.5.

Step 4: 2-(4-fluorobenzyl)-9-hydroxy-4-[2-(1H-imidazol-1-yl)ethyl]-7-isopropyl-3,4-dihydro-2H-pyrazino[1,2-c]pyrimidine-1,6,8(7H)-trione Dry NaH (95%; 3 mg, 0.13 mmol) was taken up in anhydrous dimethylformamide (0.6 mL) under N$_2$ and cooled to 0° C. To the mixture was added imidazole (9 mg, 0.13 mmol) and a solution of 2-(4-fluorobenzyl)-7-isopropyl-4-{2-[(methylsulfonyl)oxy]ethyl}-1,6,8-trioxo-1,3,4,6,7,8-hexahydro-2H-pyrazino[1,2-c]pyrimidine-9-yl pivalate (70 mg, 0.13 mmol) in DMF (1 mL). The resulting yellow solution was stirred overnight while warming to room temperature. The product was purified by reverse phase preparative HPLC (95:5 to 5:95 A:B where A=0.1% TFA-H$_2$O and B=0.1% TFA-MeCN over 30 min) to afford the TFA salt of the title compound. $^1$H NMR (CD$_3$OD, 500 MHz): δ 8.91 (s, 1 H), 7.62-7.58 (m, 2 H), 7.46-7.43 (m, 2 H), 7.14-7.10 (m, 2 H), 5.19-5.16 (m, 1 H), 4.78-4.71 (m, 2 H), 4.54 (d, J=14.5 MHz, 1 H), 4.15 (t, J=7.2 MHz, 2 H), 3.82 (dd, J=4.0 MHz, 13.5 MHz, 1 H), 3.47 (dd, J=2.0 MHz, 14.0 MHz, 1 H), 2.18-2.16 (m, 1 H), 1.97-1.94 (m, 1 H), 1.48 (dd, J=4.5 MHz, 7.0 MHz, 6 H). HRMS (FT/ICR) M+H: calcd for (C$_{22}$H$_{25}$FN$_5$O$_4$)$^+$ 442.1885. found 442.1866.

EXAMPLE 75

2-(4-fluorobenzyl)-9-hydroxy-4-(2-hydroxyethyl)-7-isopropyl-3,4-dihydro-2H-pyrazino[1,2-c]pyrimidine-1,6,8(7H)-trione

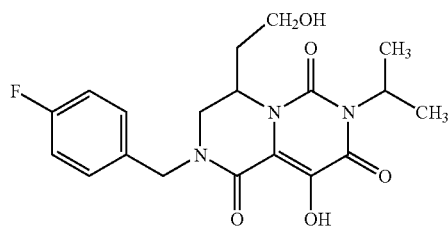

To a stirred solution of 2-(4-fluorobenzyl)-4-(2-hydroxyethyl)-7-isopropyl-1,6,8-trioxo-1,3,4,6,7,8-hexahydro-2H-pyrazino[1,2-c]pyrimidine-9-yl pivalate (Example 74, Step 2, 40 mg, 0.08 mmol) in methanol (0.5 mL) was added sodium methoxide (25 wt. % solution in methanol, 1.6 mL) and the mixture stirred at room temperature for 20 min. The reaction was quenched by dropwise addition of 1 N hydrochloric acid and the solvent was removed in vacuo. The resulting residue was taken up in methylene chloride, filtered, and the filtrate concentrated. The residue was purified by reverse phase preparative HPLC (95:5 to 5:95 A:B where A=0.1% TFA-H$_2$O and B=0.1% TFA-MeCN over 30 min) to afford the title compound. $^1$H NMR (CD$_3$OD, 400 MHz): δ 7.44-7.40 (m, 2 H), 7.13-7.08 (m, 2 H), 5.19-5.15 (m, 1 H), 4.92-4.75 (m, 2 H), 4.51 (d, J=14.4 MHz, 1 H), 3.75 (dd, J=3.8 MHz, 13.4 MHz, 1 H), 3.51 (dd, J=1.6 MHz, 13.6 MHz, 1 H), 3.42-3.30 (m, 2 H), 1.76-1.71 (m, 1 H), 1.62-1.57 (m, 1 H), 1.45 (d, J=7.2 MHz, 6 H). HRMS (FT/ICR) M+H: calcd for (C$_{19}$H$_{23}$FN$_3$O$_5$)$^+$ 392.1616. found 392.1625.

EXAMPLE 76

2-(4-fluorobenzyl)-9-hydroxy-7-isopropyl-4-(N-methyl-N-methylsulfonyl-2-aminoethyl)-3,4-dihydro-2H-pyrazino[1,2-c]pyrimidine-1,6,8(7H)-trione

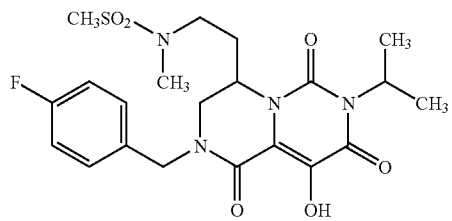

2-(4-Fluorobenzyl)-7-isopropyl-4-[2-(methylamino) ethyl]-1,6,8-trioxo-1,3,4,6,7,8-hexahydro-2H-pyrazino[1,2-c]pyrimidin-9-yl acetate (Example 67, Step 2, 37 mg, 0.08 mmol) in CH$_2$Cl$_2$ (1.5 mL) was treated with a large excess of reagents (70 μL MsCl, 270 μL triethylamine and 20 mg DMAP). Stirring the reaction at ambient temperature overnight gave complete conversion to the sulfonamide with exchange of the 9-acetate to the 9-mesylate. The solvent was removed under a steady nitrogen stream at 50° C. and the residue dissolved in MeOH (1 mL) and treated with a solution of sodium methoxide in MeOH (25 wt %, 2.5 mL). After four days of stirring at ambient temperature, cleavage of the 9-mesylate to the 9-hydroxy was complete. The mixture was quenched by the addition of TFA and water and was then concentrated under a steady stream of nitrogen at 50° C. The crude material was purified by reverse phase preparative HPLC to afford the title compound as an off-white solid. $^1$H NMR (500 MHz, CDCl$_3$) δ 11.73 (s, 1 H), 7.38-7.27 (m, 2 H), 7.09-7.05 (m, 2 H), 5.22-5.15 (m, 1 H), 4.96 (d, J=14.5 Hz, 1 H), 4.78-4.76 (m, 1 H), 4.37 (d, J=14.0 Hz, 1 H), 3.72 (dd, J=1.5, 14.0 Hz, 1 H), 3.62 (dd, J=3.8, 14.0 Hz, 1 H), 2.83 (s, 3 H), 2.80-2.66 (m, 5 H), 1.90-1.83 (m, 1 H), 1.56-1.49 (m, 1 H), 1.47 (d, J=7.0 Hz, 6 H). HRMS (APCI) M+H: calcd for $(C_{21}H_{28}FN_4O_6S)^+$ 483.1708. found 483.1729.

EXAMPLE 77

2-(4-fluorobenzyl)-9-hydroxy-7-isopropyl-4-[2-(4-morpholinyl)ethyl]-3,4-dihydro-2H-pyrazino[1,2-c]pyrimidine-1,6,8(7H)-trione

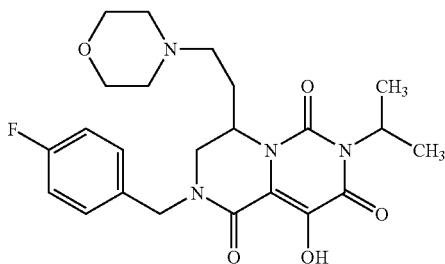

The title compound was prepared using the procedures given in Example 73 except that morpholine was used in place of 1,2,3,4-tetrahydroisoquinoline. The TFA salt of the title compound was obtained as a solid. $^1$HNMR (400 MHz, CD$_3$OD) δ 7.47-7.43 (m, 2H), 7.17-7.13 (m, 2H), 5.17 (t, J=6.8 Hz, 1H), 4.88 (d, J=14.8 Hz, 1H), 4.58 (d, J=14.8 Hz, 1H), 3.98-3.81 (m, 6H), 3.45 (dd, J=1.2, 13.6 Hz, 2H), 3.13- 3.01 (m, 5H), 1.98-1.88 (m, 2H), 1.47 (dd, J=1.6, 6.8 Hz, 6H). HRMS (FT/ES) M+H: calcd for $(C_{23}H_{29}FN_4O_5)^+$ 461.2195. found 461.2213.

EXAMPLE 78

7-(4-acetylmorpholin-3-ylmethyl)-2-(4-fluorobenzyl)-9-hydroxy-3,4-dihydro-2H-pyrazino[1,2-c]pyrimidine-1,6,8(7H)-trione

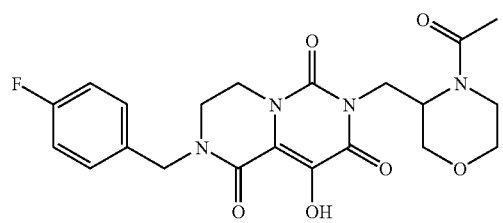

To 2-(4-fluorobenzyl)-9-hydroxy-7-(morpholin-3-ylmethyl)-3,4-dihydro-2H-pyrazino[1,2-c]pyrimidine-1,6,8(7H)-trione mono TFA salt (72 mg, 0.14 mmol, Example 17) dissolved in dry methylene chloride (1 mL) was added pyridine (13 μL, 0.17 mmol) and acetic anhydride (28 mg, 0.28 mmol). The reaction was stirred overnight at room temperature. The reaction was purified by prep HPLC using a C18 stationary phase and a water/acetonitrile/TFA gradient to obtain the title compound as a white powder after lyophilization from dioxane. High Resolution FT-ICR $C_{21}H_{23}FN_4O_6$+H=447.1677; calculated 447.1675.

EXAMPLES 79-85

The compounds in the following table were prepared in accordance with the procedures set forth in Example 4, Steps 8 and 9, using the appropriate bromide starting materials in place of 2-(chloromethyl)quinoline hydrochloride.

| Example | Compound | Data |
|---|---|---|
| 79 | 2-(2-chloro-4-fluorobenzyl)-9-hydroxy-7-isopropyl-3,4-dihydro-2H-pyrazino[1,2-c]pyrimidine-1,6,8(7H)-trione | HPLC RT = 3.37 min (Method A); ES MS (M + H) = 382. |
| 80 | 2-(3-chloro-4-fluorobenzyl)-9-hydroxy-7-isopropyl-3,4-dihydro-2H-pyrazino[1,2-c]pyrimidine-1,6,8(7H)-trione | HPLC RT = 3.37 min (Method A); ES MS (M + H) = 382. |

-continued

| Example | Compound | Data |
|---|---|---|
| 81 | 9-hydroxy-7-isopropyl-2-(2-napthylmethyl)-3,4-dihydro-2H-pyrazino[1,2-c]pyrimidine-1,6,8(7H)-trione | HPLC RT = 3.46 min (Method A); ES MS (M + H) = 380. |
| 82 | 2-(2-cyanobenzyl)-9-hydroxy-7-isopropyl-3,4-dihydro-2H-pyrazino[1,2-c]pyrimidine-1,6,8(7H)-trione | HPLC RT = 3.03 min (Method A); ES MS (M + H) = 355. |
| 83 | 9-hydroxy-7-isopropyl-2-(1-naphthylmethyl)-3,4-dihydro-2H-pyrazino[1,2-c]pyrimidine-1,6,8(7H)-trione | HPLC RT = 3.45 min (Method A); ES MS (M + H) = 380. |
| 84 | 9-hydroxy-7-isopropyl-2-(2-pyridylmethyl)-3,4-dihydro-2H-pyrazino[1,2-c]pyrimidine-1,6,8(7H)-trione | HPLC RT = 2.46 min (Method A); ES MS (M + H) = 331. |
| 85 | 9-hydroxy-7-isopropyl-2-(3-isoquinolinylmethyl)-3,4-dihydro-2H-pyrazino[1,2-c]pyrimidine-1,6,8(7H)-trione | HPLC RT = 3.36 min (Method A); ES MS (M + H) = 381. |

EXAMPLE 86

7-(1-Acetylpiperidin-3-yl)-2-(4-fluorobenzyl)-9-hydroxy-3,4-dihydro-2H-pyrazino[1,2-c]pyrimidine-1,6,8(7H)-trione

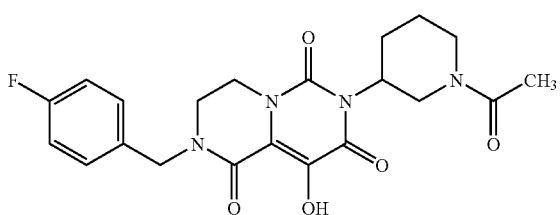

2-(4-Fluorobenzyl)-9-hydroxy-7-(piperidin-3-yl)-3,4-dihydro-2H-pyrazino[1,2-c]pyridine-1,6,8(7H)-trione was prepared from 1-Boc-3-aminopiperidine using the procedure of Example 12. The product from this reaction was acetylated using the procedure given in Example 13 to provide the title compound. HRMS ES (M+1) calc'd for C21H23FN4O5, 431.1725. found 431.1710.

EXAMPLE 87

7-cycloheptyl-2-(4-fluorobenzyl)-9-hydroxy-3,4-dihydro-2H-pyrazino[1,2-c]pyrimidine-1,6,8(7H)-trione

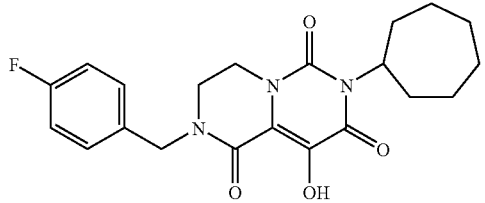

The title compound was prepared using the procedure given in Step 7 of Example 1, using aminocycloheptane in place of [(1-morpholin-4-ylcyclopentyl)methyl]amine. HRMS ES (M+1) calc'd for C21H25FN3O4, 402.1824. found 402.1832.

EXAMPLE 88

Oral Compositions

As a specific embodiment of an oral composition of a compound of this invention, 50 mg of compound of Example 1 is formulated with sufficient finely divided lactose to provide a total amount of 580 to 590 mg to fill a size 0 hard gelatin capsule. Encapsulated oral compositions containing any one of the compounds of Examples 2-87 can be similarly prepared.

EXAMPLE 89

HIV Integrase Assay: Strand Transfer Catalyzed by Recombinant Integrase

Assays for the strand transfer activity of integrase were conducted in accordance with WO 02/30930 for recombinant integrase. Representative compounds of the present invention exhibit inhibition of strand transfer activity in this assay. For example, the compounds set forth in Examples 1-87 were tested in the integrase assay and all were found to have $IC_{50}$'s less than 10 micromolar.

Further description on conducting the assay using preassembled complexes is found in Wolfe, A. L. et al., *J. Virol.* 1996, 70: 1424-1432, Hazuda et al., *J. Virol.* 1997, 71: 7005-7011; Hazuda et al., *Drug Design and Discovery* 1997, 15: 17-24; and Hazuda et al., *Science* 2000, 287: 646-650.

EXAMPLE 90

Assay for Inhibition of HIV Replication

Assays for the inhibition of acute HIV infection of T-lymphoid cells were conducted in accordance with Vacca, J. P. et al., *Proc. Natl. Acad. Sci. USA* 1994, 91: 4096. Representative compounds of the present invention exhibit inhibition of HIV replication in this assay. For example, the compounds set forth in Examples 1-87 were found to have $IC_{95}$'s of less than 10 micromolar in the present assay.

While the foregoing specification teaches the principles of the present invention, with examples provided for the purpose of illustration, the practice of the invention encompasses all of the usual variations, adaptations and/or modifications that come within the scope of the following claims.

What is claimed is:

1. A compound of formula:

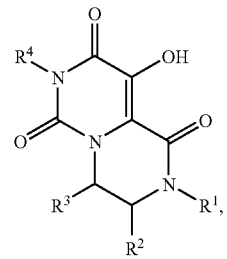

or a pharmaceutically acceptable salt thereof, wherein:

$R^1$ is $C_{1-6}$ alkyl substituted with T, wherein T is:
 (A) aryl which is:
  (i) optionally substituted with from 1 to 5 substituents each of which is independently:
   (1) —$C_{1-6}$ alkyl optionally substituted with —OH, —O—$C_{1-6}$ alkyl, —O—$C_{1-6}$ haloalkyl, —CN, —$NO_2$, —N($R^A$)$R^B$, —C(O)N($R^A$)$R^B$, —C(O)$R^A$, —$CO_2R^A$, —$SR^A$, —S(O)$R^A$, —$SO_2R^A$, —$SO_2$N($R^A$)$R^B$, —N($R^A$)C(O)$R^B$, —N($R^A$)$CO_2R^B$, —N($R^A$)$SO_2R^B$, —N($R^A$)$SO_2$N($R^A$)$R^B$, —OC(O)N($R^A$)$R^B$, or —N($R^A$)C(O)N($R^A$)$R^B$,
   (2) —O—$C_{1-6}$ alkyl,
   (3) —$C_{1-6}$ haloalkyl,
   (4) —O—$C_{1-6}$ haloalkyl,
   (5) —OH,
   (6) halo,
   (7) —CN,
   (8) —$NO_2$,
   (9) —N($R^A$)$R^B$,
   (10) —C(O)N($R^A$)$R^B$,
   (11) —C(O)$R^A$,
   (12) —$CO_2R^A$,
   (13) —$SR^A$,
   (14) —S(O)$R^A$,

(15) —SO$_2$R$^A$,
(16) —SO$_2$N(R$^A$)R$^B$,
(17) —N(R$^A$)SO$_2$R$^B$,
(18) —N(R$^A$)SO$_2$N(R$^A$)R$^B$,
(19) —N(R$^A$)C(O)R$^B$,
(20) —N(R$^A$)C(O)—C(O)N(R$^A$)R$^B$, or
(21) —N(R$^A$)CO$_2$R$^B$, and
(ii) optionally substituted with from 1 to 3 substituents each of which is independently:
(1) -HetA,
(2) -HetB,
(3) phenyl,
(4) benzyl, or
(5) —C(O)-HetA, or
(B) heteroaryl which is:
(i) optionally substituted with from 1 to 4 substituents each of which is independently halogen, —C$_{1-6}$ alkyl, —C$_{1-6}$ haloalkyl, —O—C$_{1-6}$ alkyl, —O—C$_{1-6}$ haloalkyl, or —OH; and
(ii) optionally substituted with 1 or 2 substituents each of which is independently aryl or —C$_{1-6}$ alkyl substituted with aryl;

R$^2$ is:
(1) H,
(2) C$_{1-6}$ alkyl, or
(3) C$_{1-6}$ alkyl substituted with —CO$_2$R$^A$ or —C(O)N(R$^C$)R$^D$;
or alternatively R$^1$ and R$^2$ together with the atom to which each is attached form a saturated 5- or 6-membered ring containing the nitrogen to which R$^1$ is attached, optionally a second nitrogen atom and a balance of carbon atoms; wherein the saturated 5- or 6-membered ring is substituted with T as defined above;

R$^3$ is:
(1) H,
(2) C$_{1-6}$ alkyl, or
(3) C$_{1-6}$ alkyl substituted with:
(a) —OH,
(b) —O—C$_{1-6}$ alkyl,
(c) —N(R$^E$)2,
(d) —N(R$^E$)R$^F$,
(e) aryl, which is optionally substituted with from 1 to 5 substituents each of which is independently halo, —C$_{1-6}$ alkyl, —O—C$_{1-6}$ alkyl, —C$_{1-6}$ haloalkyl, or —OH,
(f) —O—C$_{1-6}$ alkylene-aryl, in which the aryl is optionally substituted with from 1 to 5 substituents each of which is independently halo, —C$_{1-6}$ alkyl, —O—C$_{1-6}$ alkyl, —C$_{1-6}$ haloalkyl, or —OH,
(g) heteroaryl, which is optionally substituted with from 1 to 4 substituents each of which is independently halogen, —C$_{1-6}$ alkyl, —C$_{1-6}$ haloalkyl, —O—C$_{1-6}$ alkyl, —O—C$_{1-6}$ haloalkyl, or —OH, or
(h) heteromonocycle, which is optionally substituted with from 1 to 6 substituents each of which is independently halogen, —C$_{1-6}$ alkyl, C$_{1-6}$ haloalkyl, —O—C$_{1-6}$ alkyl, —O—C$_{1-6}$ haloalkyl, or oxo;

R$^4$ is:
(1) H,
(2) C$_{1-6}$ alkyl,
(3) C$_{1-6}$ alkyl substituted with 1 or 2 substituents each of which is independently:
(a) —OH,
(b) —O—C$_{1-6}$ alkyl,
(c) —C$_{1-6}$ haloalkyl,
(d) —CO$_2$R$^A$,
(e) —C(O)N(R$^C$)R$^D$,
(f) —C(O)C(O)N(R$^A$)R$^B$,
(g) —S—C$_{1-6}$ alkyl,
(h) —S-aryl,
(i) —S(O)—C$_{1-6}$ alkyl,
(j) —S(O)-aryl,
(k) —SO$_2$—C$_{1-6}$ alkyl,
(l) —SO$_2$-aryl,
(m) —N(R$^E$)$_2$,
(n) —N(R$^E$)R$^F$,
(o) —C$_{3-8}$ cycloalkyl, which is
(i) optionally substituted with from 1 to 6 substituents each of which is independently —C$_{1-6}$ alkyl, —OH, —O—C$_{1-6}$ alkyl, or —C$_{1-6}$ haloalkyl, and
(ii) optionally substituted with (a) aryl, (b) —C$_{1-6}$ alkylene-aryl, (c) heteroaryl optionally substituted with from 1 to 3 substituents each of which is independently a —C$_{1-6}$ alkyl, or (d) heteromonocycle optionally substituted with from 1 to 4 substituents each of which is independently —C$_{1-6}$ alkyl, —C$_{1-6}$ alkylene-aryl, or oxo,
(p) aryl, which is:
(i) optionally substituted with from 1 to 5 substituents each of which is independently halo, —C$_{1-6}$ alkyl, —O—C$_{1-6}$ alkyl, —C$_{1-6}$ haloalkyl, or —OH, and
(ii) optionally substituted with (a) heteroaryl optionally substituted with from 1 to 3 substituents each of which is independently a —C$_{1-6}$ alkyl, or (b) heteromonocycle optionally substituted with from 1 to 4 substituents each of which is independently —C$_{1-6}$ alkyl, —C$_{1-6}$ alkylene-aryl, or oxo,
(q) bicyclic or tricyclic carbocycle, which is optionally substituted with from 1 to 7 substituents each of which is independently halogen, —C$_{1-6}$ alkyl, —C$_{1-6}$ haloalkyl, OH, —O—C$_{1-6}$ alkyl, or —O—C$_{1-6}$ haloalkyl,
(r) heteroaryl, which is:
(i) optionally substituted with from 1 to 4 substituents each of which is independently halogen, —C$_{1-6}$ alkyl, —C$_{1-6}$ haloalkyl, —O—C$_{1-6}$ alkyl, —O—C$_{1-6}$ haloalkyl, or —OH, and
(ii) optionally substituted with (a) aryl, (b) —C$_{1-6}$ alkylene-aryl or (c) heteromonocycle optionally substituted with from 1 to 4 substituents each of which is independently —C$_{1-6}$ alkyl, —C$_{1-6}$ alkylene-aryl, or oxo,
(s) heteromonocycle, which is:
(i) optionally substituted with from 1 to 6 substituents each of which is independently halogen, —C$_{1-6}$ alkyl, —C$_{1-6}$ haloalkyl, —O—C$_{1-6}$ alkyl, —O—C$_{1-6}$ haloalkyl, —C(O)—C$_{1-6}$ alkyl, —C(O)C(O)N(R$^A$)R$^B$, or oxo, and
(ii) optionally substituted with:
(a) —C$_{1-6}$ alkylene-C$_{3-8}$ cycloalkyl,
(b) aryl,
(c) —C$_{1-6}$ alkylene-aryl,
(d) heteroaryl optionally substituted with from 1 to 3 substituents each of which is independently a —C$_{1-6}$ alkyl,
(e) heteromonocycle optionally substituted with from 1 to 4 substituents each of which is independently —C$_{1-6}$ alkyl, —C$_{1-6}$ alkylene-aryl, or oxo, or (f) —C(O)—$C_{1-6}$ alkylene-heteromonocycle wherein the heteromonocycle is optionally substituted with from 1 to 4 substituents each of which is independently —$C_{1-6}$ alkyl, —$C_{1-6}$ alkylene-aryl, or oxo, or (s) bicyclic or tricyclic heterocycle, which is optionally substituted with from 1 to 7 substituents each of which is independently halogen, —$C_{1-6}$ alkyl, —$C_{1-6}$ haloalkyl, —O—$C_{1-6}$ alkyl, —O—$C_{1-6}$ haloalkyl, —C(O)—$C_{1-6}$ alkyl, or oxo;

(4) $C_{2-6}$ alkenyl, (5) $C_{3-8}$ cycloalkyl which is:
(a) optionally substituted with from 1 to 6 substituents each of which is independently —$C_{1-6}$ alkyl, —OH, —O—$C_{1-6}$ alkyl, or —$C_{1-6}$ haloalkyl, and
(b) optionally substituted with:
  (i) aryl, which is optionally substituted with from 1 to 5 substituents each of which is independently halo, —$C_{1-6}$ alkyl, —O—$C_{1-6}$ alkyl, —$C_{1-6}$ haloalkyl, or —OH,
  (ii) heteroaryl, which is optionally substituted with from 1 to 4 substituents each of which is independently halogen, —$C_{1-6}$ alkyl, —$C_{1-6}$ haloalkyl, —O—$C_{1-6}$ alkyl, —O—$C_{1-6}$ haloalkyl, or —OH,
  (iii) heteromonocycle, which is
    (i) optionally substituted with from 1 to 6 substituents each of which is independently halogen, —$C_{1-6}$ alkyl, —$C_{1-6}$ haloalkyl, —O—$C_{1-6}$ alkyl, —O—$C_{1-6}$ haloalkyl, —C(O)—$C_{1-6}$ alkyl, or oxo, and
    (ii) optionally substituted with —$C_{1-6}$ alkylene-aryl, or
  (iv) N($R^A$)$R^B$, (6) aryl, which is:
(a) optionally substituted with from 1 to 5 substituents each of which is independently halo, —$C_{1-6}$ alkyl, —O—$C_{1-6}$ alkyl, —$C_{1-6}$ haloalkyl, or —OH, and
(b) optionally substituted with (i) heteroaryl optionally substituted with from 1 to 3 substituents each of which is independently a —$C_{1-6}$ alkyl, or (ii) heteromonocycle optionally substituted with from 1 to 4 substituents each of which is independently —$C_{1-6}$ alkyl, —$C_{1-6}$ alkylene-aryl, or oxo, (7) bicyclic or tricyclic carbocycle, which is optionally substituted with from 1 to 7 substituents each of which is independently halogen, —$C_{1-6}$ alkyl, —$C_{1-6}$ haloalkyl, OH, —O—$C_{1-6}$ alkyl, or —O—$C_{1-6}$ haloalkyl, (8) heteroaryl, which is
(a) optionally substituted with from 1 to 4 substituents each of which is independently halogen, —$C_{1-6}$ alkyl, —$C_{1-6}$ haloalkyl, —O—$C_{1-6}$ alkyl, —O—$C_{1-6}$ haloalkyl, or —OH, and
(b) optionally substituted with (i) aryl or (ii) heteromonocycle optionally substituted with from 1 to 4 substituents each of which is independently —$C_{1-6}$ alkyl, —$C_{1-6}$ alkylene-aryl, or oxo, (9) heteromonocycle, which is
(a) optionally substituted with from 1 to 6 substituents each of which is independently halogen, —$C_{1-6}$ alkyl, —$C_{1-6}$haloalkyl, —O—$C_{1-6}$ alkyl, —O—$C_{1-6}$ haloalkyl, —C(O)—$C_{1-6}$ alkyl, —C(O)C(O)N($R^A$)$R^B$, or oxo, and
(b) optionally substituted with:
  (i) —$C_{1-6}$ alkylene-$C_{3-8}$ cycloalkyl,
  (ii) aryl,
  (iii) —$C_{1-6}$ alkylene-aryl,
  (iv) heteroaryl optionally substituted with from 1 to 3 substituents each of which is independently a —$C_{1-6}$ alkyl,
  (v) heteromonocycle optionally substituted with from 1 to 4 substituents each of which is independently —$C_{1-6}$ alkyl, —$C_{1-6}$ alkylene-aryl, or oxo, or
  (vi) —C(O)—$C_{1-6}$ alkylene-heteromonocycle wherein the heteromonocycle is optionally substituted with from 1 to 4 substituents each of which is independently —$C_{1-6}$ alkyl, —$C_{1-6}$ alkylene-aryl, or oxo, or

(10) bicyclic or tricyclic heterocycle, which is optionally substituted with from 1 to 7 substituents each of which is independently halogen, —$C_{1-6}$ alkyl, —$C_{1-6}$ haloalkyl, —O—$C_{1-6}$ alkyl, —O—$C_{1-6}$ haloalkyl, —C(O)—$C_{1-6}$ alkyl, or oxo;

each HetA is independently a $C_{4-7}$ azacycloalkyl or a $C_{3-6}$ diazacycloalkyl, either of which is optionally substituted with from 1 to 4 substituents each of which is independently $C_{1-6}$ alkyl or oxo;

each HetB is independently a 5- or 6-membered heteroaromatic ring containing from 1 to 4 heteroatoms independently selected from N, O and S, wherein the heteroaromatic ring is optionally substituted with from 1 to 4 substituents each of which is independently halo, —$C_{1-6}$ alkyl, —$C_{1-6}$ haloalkyl, —O—$C_{1-6}$ alkyl, —O—$C_{1-6}$ haloalkyl, or —OH;

each aryl is independently phenyl, indenyl, indanyl, naphthyl, or tetrahydronaphthyl;

each bicyclic carbocycle is independently a bridged or fused two-ring system containing from 7 to 11 carbons, in which each ring is either saturated or unsaturated, but neither ring is aromatic;

each tricyclic carbocycle is independently a bridged or fused or bridged and fused three-ring system containing from 8 to 12 carbons, in which each ring is either saturated or unsaturated, but no ring is aromatic;

each heteroaryl is independently (i) a 5- or 6-membered heteroaromatic ring containing from 1 to 4 heteroatoms independently selected from N, O and S or (ii) a 8- or 12-membered bicyclic, fused ring system containing from 1 to 4 heteroatoms independently selected from N, O and S, wherein one or both of the rings in the ring system contain at least one heteroatom, at least one ring is aromatic, and any S atom in a ring which is not aromatic is optionally present in the form of a monoxide or dioxide;

each heteromonocycle is independently a 4- to 7-membered saturated or mono-unsaturated heterocyclic ring containing at least one carbon atom and from 1 to 4 heteroatoms independently selected from N, O and S;

each bicyclic heterocycle is independently a 7- to 11-membered bridged or fused two-ring system containing from 1 to 4 heteroatoms independently selected from N, O and S, in which each ring is either saturated or unsaturated, but neither ring is aromatic, and one or both rings in the ring system contain at least one heteroatom;

each tricyclic heterocycle is independently an 8- to 12-membered bridged or fused or bridged and fused three-ring system containing from 1 to 4 heteroatoms independently selected from N, O and S, in which each ring is either saturated or unsaturated, but no ring is an aromatic, and one or two or all three of the rings contain at least one heteroatom;

each $R^A$ is independently H or $C_{1-6}$ alkyl;
each $R^B$ is independently H or $C_{1-6}$ alkyl;
each $R^C$ is independently H, $C_{1-6}$ alkyl, or $C_{1-6}$ alkyl substituted with aryl or OH;
each $R^D$ is independently H, $C_{1-6}$ alkyl, or $C_{1-6}$ alkyl substituted with aryl or OH;
each $R^E$ is independently H, $C_{1-6}$ alkyl, or $C_{1-6}$ alkyl substituted with aryl; and
each $R^F$ is independently O—$C_{1-6}$ alkyl, $SO_2$—$C_{1-6}$ alkyl, $SO_2$-aryl, $SO_2$—$N(R^C)R^D$, $C(O)$—$C_{1-6}$ alkyl, $C(O)$-aryl, $C(O)$—$N(R^C)R^D$, $C(S)$—$C_{1-6}$ alkyl, $C(S)$-aryl, or $C(S)$—$N(R^C)R^D$.

2. The compound according to claim 1, or a pharmaceutically acceptable salt thereof, wherein $R^1$ is $CH_2$-T; wherein T is:
(1) phenyl, which is (i) optionally substituted with from 1 to 4 substituents each of which is independently halo, —$C_{1-4}$ alkyl, —O—$C_{1-4}$ alkyl, —$C_{1-4}$ fluoroalkyl, CN, —$SO_2$—$C_{1-4}$ alkyl, —C(=O)—NH(—$C_{1-4}$ alkyl), or —C(=O)—N(—$C_{1-4}$ alkyl)$_2$, and (ii) optionally substituted with from 1 to 3 HetB;
(3) naphthyl, which is optionally substituted with 1 to 4 substituents each of which is independently halo, —$C_{1-4}$ alkyl, —O—$C_{1-4}$ alkyl, or —$C_{1-4}$ fluoroalkyl,
(3) pyridyl, which is optionally substituted with from 1 to 3 substituents each of which is independently halogen, —$C_{1-4}$ alkyl, —$C_{1-4}$ haloalkyl, —O—$C_{1-4}$ alkyl, —O—$C_{1-4}$ haloalkyl, or —OH, or
(4) quinolinyl or isoquinolinyl, which is optionally substituted with from 1 to 3 substituents each of which is independently halogen, —$C_{1-4}$ alkyl, —$C_{1-4}$ haloalkyl, —O—$C_{1-4}$ alkyl, —O—$C_{1-4}$ haloalkyl, or —OH; and
each HetB is independently a 5- or 6-membered heteroaromatic ring containing from 1 to 4 heteroatoms independently selected from N, O and S, wherein the heteroaromatic ring is optionally substituted with from 1 to 4 substituents each of which is independently halo, —$C_{1-4}$ alkyl, —$C_{1-4}$ haloalkyl, —O—$C_{1-4}$ alkyl, —O—$C_{1-4}$ haloalkyl, or —OH.

3. The compound according to claim 2, or a pharmaceutically acceptable salt thereof, wherein T is 4-fluorophenyl.

4. The compound according to claim 1, or a pharmaceutically acceptable salt thereof, wherein $R^2$ is:
(1) H,
(2) $C_{1-5}$ alkyl, or
(3) $C_{1-3}$ alkyl substituted with —$CO_2R^A$ or —$C(O)N(R^C)R^D$.

5. The compound according to claim 4, or a pharmaceutically acceptable salt thereof, wherein $R^2$ is H.

6. The compound according to claim 1, or a pharmaceutically acceptable salt thereof, wherein $R^3$ is:
(1) H,
(2) $C_{1-5}$ alkyl, or
(3) $C_{1-3}$ alkyl substituted with:
(a) —OH,
(b) —O—$C_{1-4}$ alkyl,
(c) —$NH_2$,
(d) —NH($C_{1-4}$ alkyl),
(e) —N($C_{1-4}$ alkyl)$_2$,
(f) —N(O—$C_{1-4}$ alkyl)-$C_{1-4}$ alkyl,
(g) —NH—$CH_2$-phenyl,
(h) —N($C_{1-4}$ alkyl)-$CH_2$-phenyl,
(i) —NH—C(O)—$C_{1-4}$ alkyl,
(j) —N($C_{1-4}$ alkyl)-C(O)—$C_{1-4}$ alkyl,
(k) —NH—C(O)-phenyl,
(l) —N($C_{1-4}$ alkyl)-C(O)-phenyl,
(m) —NH—C(O)N($C_{1-4}$ alkyl)$_2$,
(n) —N($C_{1-4}$ alkyl)-C(O)NH($C_{1-4}$ alkyl),
(o) —N($C_{1-4}$ alkyl)-C(O)N($C_{1-4}$ alkyl)$_2$,
(p) —NH—C(S)N($C_{1-4}$ alkyl)$_2$,
(q) —N($C_{1-4}$ alkyl)-C(S)NH($C_{1-4}$ alkyl),
(r) —N($C_{1-4}$ alkyl)-C(S)N($C_{1-4}$ alkyl)$_2$,
(s) —NH—$SO_2$—$C_{1-4}$ alkyl,
(t) —N($C_{1-4}$ alkyl)-$SO_2$—$C_{1-4}$ alkyl,
(u) phenyl, which is optionally substituted with from 1 to 4 substituents each of which is independently halo, —$C_{1-4}$ alkyl, —O—$C_{1-4}$ alkyl, or —$C_{1-4}$ fluoroalkyl,
(v) —O—$C_{1-3}$ alkylene-phenyl, in which the phenyl is optionally substituted with from 1 to 4 substituents each of which is independently halo, —$C_{1-4}$ alkyl, —O—$C_{1-4}$ alkyl, or —$C_{1-4}$ fluoroalkyl,
(w) HetC, which is a 5- or 6-membered heteroaromatic ring containing from 1 to 4 heteroatoms independently selected from N, O and S, which is optionally substituted with from 1 to 4 substituents each of which is independently halogen, —$C_{1-4}$alkyl, —$C_{1-4}$ fluoroalkyl, —O—$C_{1-4}$alkyl, —O—$C_{1-4}$ fluoroalkyl, or —OH,
(x) HetD, which is a 4- to 7-membered saturated heterocyclic ring containing at least one carbon atom and from 1 to 4 heteroatoms independently selected from N, O and S, which is optionally substituted with from 1 to 6 substituents each of which is independently halogen, —$C_{1-4}$ alkyl, —$C_{1-4}$ fluoroalkyl, —O—$C_{1-4}$ alkyl, —O—$C_{1-6}$ fluoroalkyl, or oxo, or
(y) HetE, which is a 4- to 7-membered saturated heterocyclic ring fused to a benzene ring, wherein the saturated heterocyclic ring contains at least one carbon atom and from 1 to 3 heteroatoms independently selected from N, O and S, wherein the benzo heterocyclic ring system is optionally substituted with from 1 to 6 substituents each of which is independently halogen, —$C_{1-4}$ alkyl, —$C_{1-4}$ fluoroalkyl, —O—$C_{1-4}$ alkyl, —O—$C_{1-6}$ fluoroalkyl, or oxo.

7. The compound according to claim 6, or a pharmaceutically acceptable salt thereof, wherein $R^3$ is H.

8. The compound according to claim 1, or a pharmaceutically acceptable salt thereof, which is a compound of Formula I, wherein $R^4$ is:
(1) H,
(2) $C_{1-5}$ alkyl,
(3) $C_{1-5}$ alkyl substituted with 1 or 2 substituents each of which is independently:
(a) —OH,
(b) —O—$C_{1-4}$ alkyl,
(c) —$C_{1-4}$ fluoroalkyl containing at least one $CF_3$ group,
(d) —$CO_2$—$C_{1-4}$ alkyl,
(e) —$C(O)NH_2$,
(f) —C(O)NH($C_{1-4}$ alkyl),
(g) —C(O)N($C_{1-4}$ alkyl)$_2$,
(h) —C(O)C(O)N($C_{1-4}$ alkyl)$_2$,
(i) —S—$C_{1-4}$ alkyl,
(j) —S-phenyl,
(k) —S(O)—$C_{1-4}$ alkyl,
(l) —$SO_2$—$C_{1-4}$ alkyl,
(m) —$NH_2$,
(n) —NH($C_{1-4}$ alkyl),
(o) —N($C_{1-4}$ alkyl)$_2$,
(p) —NH($CH_2$-phenyl),
(q) —N($C_{1-4}$ alkyl)-$CH_2$-phenyl,
(r) —NH—C(O)—$C_{1-4}$ alkyl,
(s) —N($C_{1-4}$ alkyl)-C(O)—$C_{1-4}$ alkyl,
(t) —NH—C(O)N($C_{1-4}$ alkyl)$_2$,
(u) —N($C_{1-4}$ alkyl)-C(O)N($C_{1-4}$ alkyl)$_2$,
(v) —NH—$SO_2$—$C_{1-4}$ alkyl, (w) —N($C_{1-4}$ alkyl)-$SO_2$—$C_{1-4}$ alkyl,
(x) —$C_{3-6}$ cycloalkyl, which is:
  (i) optionally substituted with from 1 to 4 substituents each of which is independently —$C_{1-4}$ alkyl, —OH, —O—$C_{1-4}$ alkyl, or —$C_{1-4}$ fluoroalkyl containing at least one $CF_3$ group, and
  (ii) optionally substituted with phenyl, benzyl, HetF, or HetG,
(y) aryl selected from the group consisting of phenyl and napthyl, wherein the aryl is:
  (i) optionally substituted with from 1 to 4 substituents each of which is independently halo, —$C_{1-4}$ alkyl, —O—$C_{1-4}$ alkyl, —$C_{1-4}$ fluoroalkyl containing at least one $CF_3$, or —OH, and
  (ii) optionally substituted with HetF or HetG,
(z) a bridged carbocycle which is bicyclo[2.2.1]heptyl, bicyclo[2.2.2]octyl, or adamantyl, wherein the bridged carbocycle is optionally substituted with from 1 to 4 substituents each of which is independently a —$C_{1-4}$ alkyl or OH,
(aa) a 5- or 6-membered heteroaromatic ring containing from 1 to 4 heteroatoms independently selected from N, O and S, which is:
  (i) optionally substituted with from 1 to 3 substituents each of which is independently a halo, —$C_{1-4}$ alkyl, —O—$C_{1-4}$ alkyl, or —$CF_3$, and
  (ii) optionally substituted with phenyl, benzyl, or HetG,
(bb) a 9- or 10-membered fused heterobicyclic aromatic ring system containing from 1 to 4 nitrogen atoms in which one or both rings in the ring system contains at least one nitrogen atom and at least one ring is aromatic, wherein the ring system is optionally substituted with from 1 to 3 substituents each of which is independently a —$C_{1-4}$ alkyl group, or
(cc) a 4- to 7-membered saturated heterocyclic ring containing at least one carbon atom and from 1 to 4 heteroatoms independently selected from N, O and S, which is:
  (i) optionally substituted with from 1 to 4 substituents each of which is independently halogen, —$C_{1-4}$ alkyl, —$CF_3$, —C(O)—$C_{1-4}$ alkyl, —C(O)C(O)N($C_{1-4}$ alkyl)$_2$, or oxo, and
  (ii) optionally substituted with $CH_2$—$C_{3-6}$ cycloalkyl, phenyl, benzyl, HetF, HetG, or —C(O)$CH_2$-HetG, or
(dd) a fused or bridged heterocycle, which is 1-azabicyclo[2.2.2]octyl, 1-azabicyclo[2.2.1]heptyl, or 1-azabicyclo[4.4.0]decyl, where the fused or bridged heterocycle is optionally substituted with from 1 to 7 substituents each of which is independently a —$C_{1-4}$ alkyl,
(4) $C_{2-4}$ alkenyl,
(5) $C_{3-7}$ cycloalkyl which is:
  (a) optionally substituted with from 1 to 4 substituents each of which is independently —$C_{1-4}$ alkyl, —OH, —O—$C_{1-4}$ alkyl, or —$C_{1-4}$ fluoroalkyl containing at least one $CF_3$, and
  (b) optionally substituted with:
    (i) phenyl, which is optionally substituted with from 1 to 4 substituents each of which is independently halo, —$C_{1-4}$ alkyl, —O—$C_{1-4}$ alkyl, —$C_{1-4}$ fluoroalkyl, or —OH,
    (ii) a 5- or 6-membered heteroaromatic ring containing from 1 to 4 heteroatoms independently selected from N, O and S, which is optionally substituted with from 1 to 3 substituents each of which is independently a halo, —$C_{1-4}$ alkyl, —O—$C_{1-4}$ alkyl, or —$CF_3$, or
    (iii) a 4- to 7-membered saturated heterocyclic ring containing at least one carbon atom and from 1 to 4 heteroatoms independently selected from N, O and S, which is:
      (i) optionally substituted with from 1 to 4 substituents each of which is independently halogen, —$C_{1-4}$ alkyl, —$CF_3$, —C(O)—$C_{1-4}$ alkyl, or oxo, and
      (ii) optionally substituted with benzyl,
    (iv)) NH($C_{1-4}$ alkyl), or
    (v) N($C_{1-4}$ alkyl)$_2$,
(6) aryl selected from the group consisting of phenyl, naphthyl and indanyl, where the phenyl is (i) optionally substituted with from 1 to 4 substituents each of which is independently halo, —$C_{1-4}$ alkyl, —O—$C_{1-4}$ alkyl, —$C_{1-4}$ fluoroalkyl containing at least one $CF_3$ group, or —OH, and (ii) optionally substituted with HetF or HetG,
(7) a bridged carbocycle which is bicyclo[2.2.1]heptyl, bicyclo[2.2.2]octyl, or adamantyl, wherein the bridged carbocycle is optionally substituted with from 1 to 4 substituents each of which is independently a —$C_{1-4}$ alkyl or OH,
(8) heteroaryl which is
  (i) a 5- or 6-membered heteroaromatic ring containing from 1 to 4 heteroatoms independently selected from N, O and S, which is (a) optionally substituted with from 1 to 3 substituents each of which is independently a halo, —$C_{1-4}$ alkyl, —O—$C_{1-4}$ alkyl, —$C_{1-4}$ fluoroalkyl containing at least one $CF_3$ group and (b) optionally substituted with phenyl or HetG, or
  (ii) a 4- to 7-membered saturated heterocyclic ring fused to a benzene ring, wherein the heterocyclic ring contains at least one carbon atom and from 1 to 3 heteroatoms independently selected from N, O and S, wherein any S atom in the ring is optionally in the form of a monoxide or dioxide, and wherein the benzo-heterocyclic ring is optionally substituted with from 1 to 4 substituents each of which is independently halogen, —$C_{1-4}$ alkyl, —$CF_3$,
(9) heteromonocycle, which is a 4- to 7-membered saturated heterocyclic ring containing at least one carbon atom and from 1 to 4 heteroatoms independently selected from N, O and S, which is (i) optionally substituted with from 1 to 6 substituents each of which is independently halogen, —$C_{1-4}$ alkyl, —$CF_3$, —C(O)—$C_{1-4}$ alkyl, —C(O)C(O)N($C_{1-4}$ alkyl)$_2$, or oxo, and (b) optionally substituted with $CH_2$—$C_{3-6}$ cycloalkyl, phenyl, benzyl, HetF, HetG, or —C(O)$CH_2$-HetG, or
(10) a fused or bridged heterocycle, which is 1-azabicyclo[2.2.2]octyl, 1-azabicyclo[2.2.1]heptyl, or 1-azabicyclo[4.4.0]decyl, where the fused or bridged heterocycle is optionally substituted with from 1 to 7 substituents each of which is independently a —$C_{1-4}$ alkyl;
HetF is a 5- or 6-membered heteroaromatic ring containing from 1 to 4 heteroatoms independently selected from N, O and S, which is optionally substituted with from 1 to 3 substituents each of which is independently a —$C_{1-4}$ alkyl; and
HetG is a 4- to 7-membered saturated heterocyclic ring containing at least one carbon atom and from 1 to 4 heteroatoms independently selected from N, O and S, which is optionally substituted with from 1 to 4 substituents each of which is independently —$C_{1-4}$ alkyl, —$CH_2$-phenyl, or oxo.

9. A compound of formula:

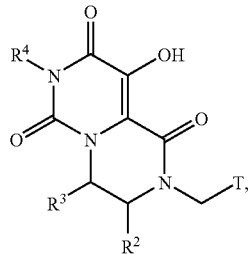

or a pharmaceutically acceptable salt thereof, wherein:
T is:
(1) phenyl which is optionally substituted with from 1 to 3 substituents each of which is independently fluoro, chloro, methyl, trifluoromethyl, methoxy, CN, —SO$_2$CH$_3$, —C(=O)NH(CH$_3$), or —C(=O)N(CH$_3$)$_2$,
(2) naphthyl,
(3) pyridyl,
(4) isoquinolinyl, or
(5) quinolinyl;
R$^2$ is:
(1) H,
(2) CH$_2$—C(O)NH(C$_{1-4}$ alkyl), or
(3) CH$_2$—C(O)N(C$_{1-4}$ alkyl)$_2$;
R$^3$ is:
(1) H,
(2) C$_{1-5}$ alkyl,
(3) (CH$_2$)$_{1-2}$—OH,
(4) (CH$_2$)$_{1-2}$—O—C$_{1-4}$ alkyl,
(5) (CH$_2$)$_{1-2}$—NH$_2$,
(6) (CH$_2$)$_{1-2}$—NH(C$_{1-4}$ alkyl),
(7) (CH$_2$)$_{1-2}$—N(C$_{1-4}$ alkyl)$_2$,
(8) (CH$_2$)$_{1-2}$—N(O—C$_{1-4}$ alkyl)-C$_{1-4}$ alkyl,
(9) (CH$_2$)$_{1-2}$—NH—CH$_2$-phenyl,
(10) (CH$_2$)$_{1-2}$—N(CH$_3$)—CH$_2$-phenyl,
(11) (CH$_2$)$_{1-2}$—NH—C(O)—C$_{1-4}$ alkyl,
(12) (CH$_2$)$_{1-2}$—N(CH$_3$)—C(O)—C$_{1-4}$ alkyl,
(13) (CH$_2$)$_{1-2}$—NH—C(O)-phenyl,
(14) (CH$_2$)$_{1-2}$—N(CH$_3$)—C(O)-phenyl,
(15) (CH$_2$)$_{1-2}$—NH—C(O)N(C$_{1-4}$ alkyl)$_2$,
(16) (CH$_2$)$_{1-2}$—N(CH$_3$)—C(O)NH(C$_{1-4}$ alkyl),
(17) (CH$_2$)$_{1-2}$—N(CH$_3$)—C(O)N(C$_{1-4}$ alkyl)$_2$,
(18) (CH$_2$)$_{1-2}$—NH—C(S)N(C$_{1-4}$ alkyl)$_2$,
(19) (CH$_2$)$_{1-2}$—N(CH$_3$)—C(S)NH(C$_{1-4}$ alkyl),
(20) (CH$_2$)$_{1-2}$—N(CH$_3$)—C(S)N(C$_{1-4}$ alkyl)$_2$,
(21) (CH$_2$)$_{1-2}$—NH—SO$_2$—C$_{1-4}$ alkyl,
(22) (CH$_2$)$_{1-2}$—N(CH$_3$)—SO$_2$—C$_{1-4}$ alkyl,
(23) (CH$_2$)$_{1-2}$-phenyl,
(24) (CH$_2$)$_{1-2}$—OCH$_2$-phenyl,
(25) (CH$_2$)$_{1-2}$-HetC, where HetC is a heteroaromatic ring selected from the group consisting of pyridyl, pyrrolyl, pyrazinyl, pyrimidinyl, pyridazinyl, triazinyl, thienyl, furanyl, imidazolyl, pyrazolyl, triazolyl, tetrazolyl, oxazolyl, isooxazolyl, oxadiazolyl, oxatriazolyl, thiazolyl, isothiazolyl, and thiadiazolyl, wherein the heteroaromatic ring is optionally substituted with 1 or 2 substituents each of which is independently halo or a C$_{1-4}$ alkyl, or
(26) (CH$_2$)$_{1-2}$-HetD, where HetD is a saturated heterocyclic ring selected from the group consisting of piperidinyl, morpholinyl, thiomorpholinyl, thiazolidinyl, isothiazolidinyl, oxazolidinyl, isoxazolidinyl, pyrrolidinyl, imidazolidinyl, piperazinyl, tetrahydrofuranyl, tetrahydrothienyl, pyrazolidinyl, hexahydropyrimidinyl, thiazinanyl, thiazepanyl, thiadiazepanyl, dithiazepanyl, azepanyl, diazepanyl, thiadiazinanyl, tetrahydropyranyl, tetrahydrothiopyranyl, and dioxanyl; wherein the saturated heterocyclic ring is optionally substituted with from 1 to 4 substituents each of which is independently oxo or a C$_{1-4}$ alkyl;
R$^4$ is
(1) H,
(2) C$_{1-4}$ alkyl,
(3) (CH$_2$)$_{1-3}$L$^1$ or CH(CH$_3$)-L$^1$, wherein L$^1$ is:
(a) —O—C$_{1-4}$ alkyl,
(b) —CF$_3$,
(c) —CO$_2$—C$_{1-4}$ alkyl,
(d) —NH(C$_{1-4}$ alkyl),
(e) —N(C$_{1-4}$ alkyl)$_2$,
(f) —S—C$_{1-4}$ alkyl,
(g) —C$_{3-6}$ cycloalkyl, which is optionally substituted with —C$_{1-4}$ alkyl, —OCH$_3$, —CF$_3$, —OH, phenyl, morpholinyl optionally substituted with CH$_3$, piperidinyl optionally substituted with CH$_3$, or piperazinyl optionally substituted with CH$_3$,
(i) aryl selected from the group consisting of phenyl and naphthyl, where the phenyl is optionally substituted with 1 or 2 substituents each of which is independently halo, —CH$_3$, —OCH$_3$, —CF$_3$, or —OH,
(j) a heteroaryl selected from the group consisting of pyridyl, pyrimidinyl, oxazolyl, isoxazolyl, thiazolyl, isothiazolyl, pyrrolyl, pyrazolyl, imidazolyl, thienyl, furanyl, quinolinyl, isoquinolinyl, cinnolinyl, quinazolinyl, and imidazo[1,2-a]pyridinyl,
(k) a saturated heterocyclic ring selected from the group consisting of piperidinyl, morpholinyl, thiomorpholinyl, piperazinyl, and dioxanyl, where the saturated heterocyclic ring is optionally substituted with methyl, —C(O)CH$_3$, —C(O)C(O)N(CH$_3$)$_2$, or oxo and optionally substituted with —CH$_2$-cyclopropyl, benzyl or a heteroaryl selected from the group consisting of pyridyl, pyrimidinyl, and pyrazinyl, or
(l) 1-azabicyclo[4.4.0]decyl,
(4) C$_{1-3}$ alkyl, either of which is substituted with:
(a) —CO$_2$—C$_{1-4}$ alkyl and with —SCH$_3$ or —SCH$_2$CH$_3$,
(b) a saturated heterocyclic ring and with either a C$_{3-6}$ cycloalkyl or a heteroaryl, wherein
(i) the saturated heterocyclic ring is selected from the group consisting of piperidinyl, morpholinyl, thiomorpholinyl, and piperazinyl, wherein the saturated ring is optionally substituted with 1 or 2 methyl groups, and
(ii) the heteroaryl is selected from the group consisting of pyridyl, pyrimidinyl, oxazolyl, isoxazolyl, thiazolyl, isothiazolyl, pyrrolyl, pyrazolyl, imidazolyl, thienyl, and furanyl,
(c) two C$_{3-6}$ cycloalkyl groups that are the same or different,
(5) (CH$_2$)$_{0-1}$C(CH$_3$)$_2$(CH$_2$)$_{0-1}$-L$^2$ wherein L$^2$ is —CO$_2$—C$_{1-4}$ alkyl or a saturated heterocyclic ring selected from the group consisting of piperidinyl, morpholinyl, thiomorpholinyl, and piperazinyl, wherein the saturated ring is optionally substituted with 1 or 2 methyl groups,
(6) CH(CH$_3$)CH$_2$—O—C$_{1-4}$ alkyl,
(7) (CH$_2$)$_{1-2}$CH=CH$_2$, (8) $C_{3-7}$ cycloalkyl optionally substituted with —$C_{1-4}$ alkyl, —OH, —OCH$_3$, —CF$_3$, phenyl, or a saturated heterocyclic ring selected from the group consisting of piperidinyl, piperazinyl, and morpholinyl, where the saturated heterocyclic ring is optionally substituted with 1 or 2 methyl groups, (9) aryl selected from the group consisting of phenyl, naphthyl and indanyl, where the phenyl is optionally substituted with —$C_{1-4}$ alkyl, —OCH$_3$, —CF$_3$, or a saturated heterocyclic ring selected from the group consisting of piperidinyl, piperazinyl, and morpholinyl, where the saturated heterocyclic ring is optionally substituted with 1 or 2 methyl groups,

(10) adamantyl which is optionally substituted with methyl or OH,

(11) heteroaryl selected from the group consisting of pyridyl, pyrimidinyl, pyrazinyl, and thiochromanyl in which the S atom is optionally in the form of a monoxide or dioxide, where the heteroaryl is optionally substituted with 1 or 2 substituents each of which is independently a —CH$_3$, —OCH$_3$, or a saturated heterocyclic ring selected from the group consisting of piperidinyl, piperazinyl, and morpholinyl, where the saturated heterocyclic ring is optionally substituted with 1 or 2 methyl groups,

(12) a saturated heterocyclic ring selected from the group consisting of piperidinyl, morpholinyl, thiomorpholinyl, thiazolidinyl, isothiazolidinyl, oxazolidinyl, isoxazolidinyl, pyrrolidinyl, imidazolidinyl, piperazinyl, tetrahydrofuranyl, tetrahydrothienyl, pyrazolidinyl, hexahydropyrimidinyl, thiazinanyl, thiazepanyl, thiadiazepanyl, dithiazepanyl, azepanyl, diazepanyl, thiadiazinanyl, tetrahydropyranyl, tetrahydrothiopyranyl, and dioxanyl, wherein the saturated heterocyclic ring is optionally substituted (i) with from 1 to 6 methyl groups, (ii) with 1 or 2 substituents each of which is independently —CF$_3$, —C(O)CH$_3$, —C(O)C(O)N(CH$_3$)$_2$, or oxo and (iii) with —CH$_2$-cyclopropyl, benzyl, —C(O)CH$_2$-morpholinyl, or —C(O)CH$_2$-piperidinyl, or

(13) 1-azabicyclo[2.2.2]octyl or 1-azabicyclo[4.4.0]decyl.

10. A compound, or a pharmaceutically acceptable salt thereof, selected from the group consisting of:

2-(4-fluorobenzyl)-9-hydroxy-7-[(1-morpholin-4-ylcyclopentyl)methyl]-3,4-dihydro-2H-pyrazino[1,2-c]pyrimidine-1,6,8(7H)-trione;

2-(4-Fluorobenzyl)-9-hydroxy-7-methyl-3,4-dihydro-2H-pyrazino[1,2-c]pyrimidine-1,6,8(7H)-trione;

9-hydroxy-7-isopropyl-2-(quinolin-2-ylmethyl)-3,4-dihydro-2H-pyrazino[1,2-c]pyrimidine-1,6,8(7H)-trione;

7-Cyclopentyl-3-(N,N-dimethylaminocarbonylmethyl)-2-(4-fluorobenzyl)-9-hydroxy-3,4-dihydro-2H-pyrazino[1,2-c]pyrimidine-1,6,8(7H)-trione;

2-(4-Fluorobenzyl)-9-hydroxy-7-isopropyl-4-[2-(N-methoxy-N-methylamino)ethyl]-3,4-dihydro-2H-pyrazino[1,2-c]pyrimidine-1,6,8(7H)-trione;

racemic-(7R,9aS)-4-hydroxy-2-isopropyl-7-phenyl-8,9,9a,10-tetrahydro-7H-pyrrolo[1',2':4,5]pyrazino[1,2-c]pyrimidine-1,3,5(2H)-trione;

2-(4-Fluorobenzyl)-9-hydroxy-7-[(1R,2S)-2-phenylcyclopropyl]-3,4-dihydro-2H-pyrazino[1,2-c]pyrimidine-1,6,8(7H)-trione;

7-(1-Adamantyl)-2-(4-fluorobenzyl)-9-hydroxy-3,4-dihydro-2H-pyrazino[1,2-c]pyrimidine-1,6,8(7H)-trione;

2-(4-Fluorobenzyl)-9-hydroxy-7-[1-(1-naphthyl)ethyl]-3,4-dihydro-2H-pyrazino[1,2-c]pyrimidine-1,6,8(7H)-trione;

2-(4-Fluorobenzyl)-9-hydroxy-7-(piperidin-4-yl)-3,4-dihydro-2H-pyrazino[1,2-c]pyrimidine-1,6,8(7H)-trione;

7-(1-Acetylpiperidin-4-yl)-2-(4-fluorobenzyl)-9-hydroxy-3,4-dihydro-2H-pyrazino[1,2-c]pyrimidine-1,6,8(7H)-trione;

7-[1-(Cyclopropylmethyl)piperidin-4-yl]-2-(4-fluorobenzyl)-9-hydroxy-3,4-dihydro-2H-pyrazino[1,2-c]pyrimidine-1,6,8(7H)-trione;

2-(4-Fluorobenzyl)-9-hydroxy-7-[1-(morpholin-4-ylacetyl)piperidin-4-yl]-3,4-dihydro-2H-pyrazino[1,2-c]pyrimidine-1,6,8(7H)-trione;

7-[(4-Benzylmorpholin-3-yl)methyl]-2-(4-fluorobenzyl)-9-hydroxy-3,4-dihydro-2H-pyrazino [1,2-c]pyrimidine-1,6,8(7H)-trione;

2-(4-Fluorobenzyl)-9-hydroxy-7-(3-morpholinylmethyl)-3,4-dihydro-2H-pyrazino[1,2-c]pyrimidine-1,6,8(7H)-trione;

2-(3-{[2-(4-Fluorobenzyl)-9-hydroxy-1,6,8-trioxo-1,3,4,8-tetrahydro-2H-pyrazino[1,2-c]pyrimidin-7(6H)-yl]methyl}morpholin-4-yl)-N,N-dimethyl-2-oxoacetamide;

7-cyclopentyl-2-(4-fluorobenzyl)-9-hydroxy-3,4-dihydro-2H-pyrazino[1,2-c]pyrimidine-1,6,8(7H)-trione;

2-(4-fluorobenzyl)-9-hydroxy-7-(trans-4-hydroxycyclohexyl)-3,4-dihydro-2H-pyrazino[1,2-c]pyrimidine-1,6,8(7H)-trione;

7-(2,3-dihydro-1H-inden-2-yl)-2-(4-fluorobenzyl)-9-hydroxy-3,4-dihydro-2H-pyrazino[1,2-c]pyrimidine-1,6,8(7H)-trione;

7-(4-tert-butylcyclohexyl)-2-(4-fluorobenzyl)-9-hydroxy-3,4-dihydro-2H-pyrazino[1,2-c]pyrimidine-1,6,8(7H)-trione;

7-(2,2-dimethyltetrahydro-2H-pyran-4-yl)-2-(4-fluorobenzyl)-9-hydroxy-3,4-dihydro-2H-pyrazino[1,2-c]pyrimidine-1,6,8(7H)-trione;

2-(4-fluorobenzyl)-9-hydroxy-7-(4-methoxyphenyl)-3,4-dihydro-2H-pyrazino[1,2-c]pyrimidine-1,6,8(7H)-trione;

2-(4-fluorobenzyl)-9-hydroxy-7-(6-methoxypyridin-3-yl)-3,4-dihydro-2H-pyrazino[1,2-c]pyrimidine-1,6,8(7H)-trione;

7-azepan-1-yl-2-(4-fluorobenzyl)-9-hydroxy-3,4-dihydro-2H-pyrazino[1,2-c]pyrimidine-1,6,8(7H)-trione;

7-(1,4-dioxan-2-ylmethyl)-2-(4-fluorobenzyl)-9-hydroxy-3,4-dihydro-2H-pyrazino[1,2-c]pyrimidine-1,6,8(7H)-trione;

2-(4-fluorobenzyl)-9-hydroxy-7-(isoquinolin-1-ylmethyl)-3,4-dihydro-2H-pyrazino[1,2-c]pyrimidine-1,6,8(7H)-trione;

2-(4-fluorobenzyl)-9-hydroxy-7-(1,3-thiazol-4-ylmethyl)-3,4-dihydro-2H-pyrazino[1,2-c]pyrimidine-1,6,8(7H)-trione;

2-(4-fluorobenzyl)-9-hydroxy-7-[2-(thien-2-yl)ethyl]-3,4-dihydro-2H-pyrazino[1,2-c]pyrimidine-1,6,8(7H)-trione;

2-(4-fluorobenzyl)-9-hydroxy-7-(2-imidazo[1,2-a]pyridin-2-ylethyl)-3,4-dihydro-2H-pyrazino[1,2-c]pyrimidine-1,6,8(7H)-trione;

2-(4-fluorobenzyl)-9-hydroxy-7-(2,2,2-trifluoroethyl)-3,4-dihydro-2H-pyrazino[1,2-c]pyrimidine-1,6,8(7H)-trione;

tert-butyl 2-[2-(4-fluorobenzyl)-9-hydroxy-1,6,8-trioxo-1,3,4,8-tetrahydro-2H-pyrazino[1,2-c]pyrimidin-7(6H)-yl]-2-methylpropanoate;

7-[2-(ethylthio)ethyl]-2-(4-fluorobenzyl)-9-hydroxy-3,4-dihydro-2H-pyrazino[1,2-c]pyrimidine-1,6,8(7H)-trione;

methyl 2-[2-(4-fluorobenzyl)-9-hydroxy-1,6,8-trioxo-1,3,4,8-tetrahydro-2H-pyrazino[1,2-c]pyrimidin-7(6H)-yl]-4-(methylthio)butanoate;

2-(4-fluorobenzyl)-9-hydroxy-7-(tetrahydro-2H-thiopyran-4-yl)-3,4-dihydro-2H-pyrazino[1,2-c]pyrimidine-1,6,8(7H)-trione;

7-(3,4-dihydro-2H-thiochromen-4-yl)-2-(4-fluorobenzyl)-9-hydroxy-3,4-dihydro-2H-pyrazino[1,2-c]pyrimidine-1,6,8(7H)-trione;

2-(4-fluorobenzyl)-9-hydroxy-7-(tetrahydro-2H-pyran-4-yl)-3,4-dihydro-2H-pyrazino[1,2-c]pyrimidine-1,6,8(7H)-trione;

7-dicyclopropylmethyl-2-(4-fluorobenzyl)-9-hydroxy-3,4-dihydro-2H-pyrazino[1,2-c]pyrimidine-1,6,8(7H)-trione;

2-(4-fluorobenzyl)-9-hydroxy-7-[4-(4-morpholinyl)phenyl]-3,4-dihydro-2H-pyrazino[1,2-c]pyrimidine-1,6,8(7H)-trione;

7-(1-benzyl-2-oxo-azacyclohept-3-yl)-2-(4-fluorobenzyl)-9-hydroxy-3,4-dihydro-2H-pyrazino[1,2-c]pyrimidine-1,6,8(7H)-trione;

7-cyclohexyl-2-(4-fluorobenzyl)-9-hydroxy-3,4-dihydro-2H-pyrazino[1,2-c]pyrimidine-1,6,8(7H)-trione;

2-(4-fluorobenzyl)-9-hydroxy-7-(trans-2-hydroxycyclohexyl)-3,4-dihydro-2H-pyrazino[1,2-c]pyrimidine-1,6,8(7H)-trione;

2-(4-fluorobenzyl)-9-hydroxy-7-(3-tetrahydrofuryl)-3,4-dihydro-2H-pyrazino[1,2-c]pyrimidine-1,6,8(7H)-trione;

7-cyclobutyl-2-(4-fluorobenzyl)-9-hydroxy-3,4-dihydro-2H-pyrazino[1,2-c]pyrimidine-1,6,8(7H)-trione;

2-(4-fluorobenzyl)-9-hydroxy-7-(3-hydroxyadamant-1-yl)-3,4-dihydro-2H-pyrazino[1,2-c]pyrimidine-1,6,8(7H)-trione;

7-[4-(1-piperidinyl)phenyl]-2-(4-fluorobenzyl)-9-hydroxy-3,4-dihydro-2H-pyrazino[1,2-c]pyrimidine-1,6,8(7H)-trione;

7-(1-azabicyclo[2.2.2]oct-3-yl)-2-(4-fluorobenzyl)-9-hydroxy-3,4-dihydro-2H-pyrazino[1,2-c]pyrimidine-1,6,8(7H)-trione;

2-(4-fluorobenzyl)-9-hydroxy-7-(1,2,2,6,6-pentamethyl-4-piperidinyl)-3,4-dihydro-2H-pyrazino[1,2-c]pyrimidine-1,6,8(7H)-trione;

2-(4-fluorobenzyl)-9-hydroxy-7-{1-[(2-pyrimidinyl)piperidine-3-yl]methyl}-3,4-dihydro-2H-pyrazino[1,2-c]pyrimidine-1,6,8(7H)-trione;

2-(4-fluorobenzyl)-9-hydroxy-7-[1-(2-pyridyl)ethyl]-3,4-dihydro-2H-pyrazino[1,2-c]pyrimidine-1,6,8(7H)-trione;

2-(4-fluorobenzyl)-9-hydroxy-7-[3-(1-imidazolyl)propyl]-3,4-dihydro-2H-pyrazino[1,2-c]pyrimidine-1,6,8(7H)-trione;

7-[3-(N,N-dibutyl)propyl]-2-(4-fluorobenzyl)-9-hydroxy-3,4-dihydro-2H-pyrazino[1,2-c]pyrimidine-1,6,8(7H)-trione;

2-(4-fluorobenzyl)-9-hydroxy-7-[2-(4-morpholinyl)-2-(4-pyridyl)ethyl]-3,4-dihydro-2H-pyrazino[1,2-c]pyrimidine-1,6,8(7H)-trione;

2-(4-fluorobenzyl)-9-hydroxy-7-{[1-(4-methylpiperazin-4-yl)cyclohexyl]methyl}-3,4-dihydro-2H-pyrazino[1,2-c]pyrimidine-1,6,8(7H)-trione;

2-(4-fluorobenzyl)-9-hydroxy-7-(2-methoxy-1-methylethyl)-3,4-dihydro-2H-pyrazino[1,2-c]pyrimidine-1,6,8(7H)-trione;

7-[2,2-dimethyl-3-(4-morpholinyl)propyl]-2-(4-fluorobenzyl)-9-hydroxy-3,4-dihydro-2H-pyrazino[1,2-c]pyrimidine-1,6,8(7H)-trione;

2-(4-fluorobenzyl)-9-hydroxy-7-[2-(4-morpholinyl)cyclohexyl]-3,4-dihydro-2H-pyrazino[1,2-c]pyrimidine-1,6,8(7H)-trione;

2-(4-fluorobenzyl)-9-hydroxy-7-[2-(4-morpholinyl)pyrid-5-yl]-3,4-dihydro-2H-pyrazino[1,2-c]pyrimidine-1,6,8(7H)-trione;

2-(4-fluorobenzyl)-9-hydroxy-7-(cis-2-hydroxycyclohexyl)-3,4-dihydro-2H-pyrazino[1,2-c]pyrimidine-1,6,8(7H)-trione;

7-(1-azabicyclo[4.4.0]dec-5-ylmethyl)-2-(4-fluorobenzyl)-9-hydroxy-3,4-dihydro-2H-pyrazino[1,2-c]pyrimidine-1,6,8(7H)-trione;

7-(1,1-dioxidotetrahydro-2H-thiopyran-4-yl)-2-(4-fluorobenzyl)-9-hydroxy-3,4-dihydro-2H-pyrazino[1,2-c]pyrimidine-1,6,8(7H)-trione;

7-(1,1-dioxido-3,4-dihydro-2H-thiochromen-4-yl)-2-(4-fluorobenzyl)-9-hydroxy-3,4-dihydro-2H-pyrazino[1,2-c]pyrimidine-1,6,8(7H)-trione;

2-(4-Fluorobenzyl)-9-hydroxy-7-isopropyl-4-[2-(methylamino)ethyl]-3,4-dihydro-2H-pyrazino[1,2-c]pyrimidine-1,6,8(7H)-trione;

N-{2-[2-(4-Fluorobenzyl)-9-hydroxy-7-isopropyl-1,6,8-trioxo-1,3,4,6,7,8-hexahydro-2H-pyrzino[1,2-c]pyrimidine-4-yl]ethyl}-N-methylacetamide;

4-{2-[Benzyl(methyl)amino]ethyl}-2-(4-fluorobenzyl)-9-hydroxy-7-isopropyl-3,4-dihydro-2H-pyrazino[1,2-c]pyrimidine-1,6,8(7H)-trione;

N-{2-[2-(4-Fluorobenzyl)-9-hydroxy-7-isopropyl-1,6,8-trioxo-1,3,4,6,7,8-hexahydro-2H-pyrazino[1,2-c]pyrimidine-4-yl]ethyl}-N'-isopropyl-N-methylthiourea;

N-{2-[2-(4-fluorobenzyl)-9-hydroxy-7-isopropyl-1,6,8-trioxo-1,3,4,6,7,8-hexahydro-2H-pyrazino[1,2-c]pyrimidin-4-yl]ethyl}-N'-isopropyl-N-methylurea;

N-{2-[2-(4-Fluorobenzyl)-9-hydroxy-7-isopropyl-1,6,8-trioxo-1,3,4,6,7,8-hexahydro-2H-pyrazino[1,2-c]pyrimidine-4-yl]ethyl}-N-methylbenzamide;

4-[(Benzyloxy)methyl]-2-(4-fluorobenzyl)-9-hydroxy-7-isopropyl-3,4-dihydro-2H-pyrazino[1,2-c]pyrimidine-1,6,8(7H)-trione;

4-[2-(Benzyloxy)ethyl]-2-(4-fluorobenzyl)-9-hydroxy-7-isopropyl-3,4-dihydro-2H-pyrazino[1,2-c]pyrimidine-1,6,8(7H)-trione;

4-[2-(3,4-Dihydroisoquinolin-2(1H)-yl)ethyl]-2-(4-fluorobenzyl)-9-hydroxy-7-isopropyl-3,4-dihydro-2H-pyrazino[1,2-c]pyrimidine-1,6,8(7H)-trione;

2-(4-fluorobenzyl)-9-hydroxy-4-[2-(1H-imidazol-1-yl)ethyl]-7-isopropyl-3,4-dihydro-2H-pyrazino[1,2-c]pyrimidine-1,6,8(7H)-trione;

2-(4-fluorobenzyl)-9-hydroxy-4-(2-hydroxyethyl)-7-isopropyl-3,4-dihydro-2H-pyrazino[1,2-c]pyrimidine-1,6,8(7H)-trione;

2-(4-fluorobenzyl)-9-hydroxy-7-isopropyl-4-(N-methyl-N-methylsulfonyl-2-aminoethyl)-3,4-dihydro-2H-pyrazino[1,2-c]pyrimidine-1,6,8(7H)-trione;

2-(4-fluorobenzyl)-9-hydroxy-7-isopropyl-4-[2-(4-morpholinyl)ethyl]-3,4-dihydro-2H-pyrazino[1,2-c]pyrimidine-1,6,8(7H)-trione;

7-(4-acetylmorpholin-3-ylmethyl)-2-(4-fluorobenzyl)-9-hydroxy-3,4-dihydro-2H-pyrazino[1,2-c]pyrimidine-1,6,8(7H)-trione;

2-(2-chloro-4-fluorobenzyl)-9-hydroxy-7-isopropyl-3,4-dihydro-2H-pyrazino[1,2-c]pyrimidine-1,6,8(7H)-trione;

2-(3-chloro-4-fluorobenzyl)-9-hydroxy-7-isopropyl-3,4-dihydro-2H-pyrazino[1,2-c]pyrimidine-1,6,8(7H)-trione;

9-hydroxy-7-isopropyl-2-(2-napthylmethyl)-3,4-dihydro-2H-pyrazino[1,2-c]pyrimidine-1,6,8(7H)-trione;

2-(2-cyanobenzyl)-9-hydroxy-7-isopropyl-3,4-dihydro-2H-pyrazino[1,2-c]pyrimidine-1,6,8(7H)-trione;

9-hydroxy-7-isopropyl-2-(1-naphthylmethyl)-3,4-dihydro-2H-pyrazino[1,2-c]pyrimidine-1,6,8(7H)-trione;

9-hydroxy-7-isopropyl-2-(2-pyridylmethyl)-3,4-dihydro-2H-pyrazino[1,2-c]pyrimidine-1,6,8(7H)-trione;

9-hydroxy-7-isopropyl-2-(3-isoquinolinylmethyl)-3,4-dihydro-2H-pyrazino[1,2-c]pyrimidine-1,6,8(7H)-trione 7-(1-Acetylpiperidin-3-yl)-2-(4-fluorobenzyl)-9-hydroxy-3,4-dihydro-2H-pyrazino[1,2-c]pyrimidine-1,6,8(7H)-trione; and 7-cycloheptyl-2-(4-fluorobenzyl)-9-hydroxy-3,4-dihydro-2H-pyrazino[1,2-c]pyrimidine-1,6,8(7H)-trione.

11. A pharmaceutical composition comprising an effective amount of a compound according to claim 1, or a pharmaceutically acceptable salt thereof, and a pharmaceutically acceptable carrier.

12. A method for treating infection by HIV in a subject in need thereof which comprises administering to the subject an effective amount of the compound according to claim 1, or a pharmaceutically acceptable salt thereof.

\* \* \* \* \*

UNITED STATES PATENT AND TRADEMARK OFFICE
CERTIFICATE OF CORRECTION

| | | |
|---|---|---|
| PATENT NO. | : 7,820,680 B2 | Page 1 of 1 |
| APPLICATION NO. | : 10/592222 | |
| DATED | : October 26, 2010 | |
| INVENTOR(S) | : Peter D. Williams et al. | |

It is certified that error appears in the above-identified patent and that said Letters Patent is hereby corrected as shown below:

On the cover page, at the listing of inventor information at item (75), and after the name and address of inventor Linghang Zhuang, please insert the name and address of inventor H. Marie Langford as follows:

--H. Marie Langford, Lansdale, PA (US)--

Signed and Sealed this
Third Day of May, 2011

David J. Kappos
*Director of the United States Patent and Trademark Office*